US006359434B1

(12) United States Patent
Winslow et al.

(10) Patent No.: US 6,359,434 B1
(45) Date of Patent: Mar. 19, 2002

(54) METHOD AND SYSTEM FOR DETERMINING PIPELINE CIRCUMFERENTIAL AND NON-CIRCUMFERENTIAL WALL LOSS DEFECTS IN A WATER PIPELINE

(75) Inventors: Jens Winslow; Rodney K. Ridley, both of Edmonton; Varagur S. V. Rajan, Sherwood Park; Yuwu Yu; Lawrence B. Staples, both of Edmonton, all of (CA)

(73) Assignee: Hydroscope Cananda Inc., Edmonton (CA)

( * ) Notice: Subject to any disclaimer, the term of this patent is extended or adjusted under 35 U.S.C. 154(b) by 0 days.

(21) Appl. No.: 09/164,437

(22) Filed: Sep. 30, 1998

(51) Int. Cl.$^7$ .......................... G01N 27/90; G01R 33/12
(52) U.S. Cl. .......................... 324/220; 324/240; 702/38
(58) Field of Search .............................. 324/220, 219, 324/221, 236, 237, 238, 239, 240, 242, 243; 702/38, 189, 190

(56) References Cited

U.S. PATENT DOCUMENTS

| 2,573,799 A | 11/1951 | MacLean |
| 2,992,390 A | 7/1961 | De Witte |
| 3,060,377 A | 10/1962 | Schmidt |
| 3,243,697 A | 3/1966 | Schmidt |
| 3,417,325 A | 12/1968 | McCullough et al. |
| 3,532,969 A | 10/1970 | McCullough et al. |
| 4,292,588 A | 9/1981 | Smith |
| 4,292,589 A | 9/1981 | Bonner |
| 4,372,161 A | 2/1983 | de Buda et al. |
| 4,546,314 A | 10/1985 | Minerbo et al. |
| 4,621,532 A | 11/1986 | Takagi et al. |
| 4,633,177 A | 12/1986 | David et al. |
| 4,644,272 A | 2/1987 | Janos |
| 4,751,461 A | 6/1988 | McWhirter et al. |
| 4,770,105 A | 9/1988 | Takagi et al. |
| 4,808,924 A | 2/1989 | Cecco et al. |
| 4,808,927 A | 2/1989 | Cecco et al. |
| 4,855,676 A | 8/1989 | Cecco et al. |
| 4,866,978 A | 9/1989 | Biggerstaff |
| 4,878,180 A | 10/1989 | McWhirter et al. |
| 4,909,091 A | 3/1990 | Ellmann et al. |
| 4,945,775 A | 8/1990 | Adams et al. |
| 5,049,817 A | 9/1991 | Cecco et al. |
| 5,204,622 A | 4/1993 | McCaslin et al. |
| 5,210,492 A | 5/1993 | Hosohara et al. |
| 5,214,379 A | 5/1993 | Chern |
| 5,313,838 A | 5/1994 | Gondard et al. |

(List continued on next page.)

OTHER PUBLICATIONS

David D. Mackintosh, David L. Atherton, and Sean P. Sullivan, "Remote–Field Eddy Current Signal Analysis in Small–Bore Ferromagnetic Tubes," *Materials Evaluation*, vol. 51, No. 4, Apr. 1993, pp. 492–495,500.

David Mackintosh, David Atherton, and Paul Puhach, "Through–Transmission Equations for Remote–Field Eddy Current Inspection of Small–Bore Ferromagnetic Tubes," *Materials Evaluation*, vol. 51, No. 6, Jun. 1993, pp. 744–748.

(List continued on next page.)

*Primary Examiner*—Walter Snow
(74) *Attorney, Agent, or Firm*—Christensen O'Conner Johnson Kindness PLLC

(57) ABSTRACT

In accordance with the teachings of the present invention, a method is provided for analyzing RFT data from a data file. The method includes parsing the data file into pipe lengths, calculating a phase profile for the data points within each pipe length, locating potential defects in the pipe length using the phase profiles, determining for each defect a total equivalent phase shift as a combination of a circumferential equivalent phase shift and a non-circumferential equivalent phase shift, and using the total equivalent phase shift to analyze the defect.

43 Claims, 39 Drawing Sheets

U.S. PATENT DOCUMENTS

| | | | |
|---|---|---|---|
| 5,329,824 | A | 7/1994 | Carapezza et al. |
| 5,365,169 | A | 11/1994 | Hosohara et al. |
| 5,365,331 | A | 11/1994 | Tamburrino et al. |
| 5,398,560 | A | 3/1995 | Zollingger et al. |
| 5,402,065 | A | 3/1995 | Tabari et al. |
| 5,453,688 | A | 9/1995 | Cecco et al. |
| 5,454,276 | A | 10/1995 | Wernicke |
| 5,461,312 | A | 10/1995 | Hosohara et al. |
| 5,461,313 | A | 10/1995 | Bohon et al. |
| 5,532,587 | A | 7/1996 | Downs et al. |
| 5,623,203 | A | 4/1997 | Hosohara et al. |
| 5,675,251 | A | 10/1997 | MacLean et al. |

OTHER PUBLICATIONS

David Atherton, David Mackintosh, Sean Sullivan, J.M.S. Dubois, and Thomas Schmidt, "Remote–Field Eddy Current Signal Representation," *Materials Evaluation*, vol. 51, No. 7, Jul. 1993, pp. 782–789.

David L. Atherton, Wojtek M. Czura, and David D. Mackintosh, "Remote–Field Eddy Current Defect Interactions: Effects on the External Field," *Materials Evaluation*, vol. 52, No. 11, Nov. 1994, pp. 1288–1291.

David D. Mackintosh, David L. Atherton, Thomas R. Schmidt, and David E. Russell, "Remote Field Eddy Current for Examination of Ferromagnetic Tubes," *Materials Evaluation*, vol. 54, No. 6, Jun. 1996, pp. 652–657.

David Mackintosh, Harold Smith, and Leo Rajter, "Remote Field Eddy Current Inspection of Ferromagnetic Tubes: Techniques for Signal Interpretation," Proceedings of the Fourth Conference on Fossil Plant Inspections, Jan. 18–20, 1994, San Antonio, Texas.

David Mackintosh, "Inspecting Ferromagnetic Tubes with Remote Field Eddy Current: Indentifying Metal Loss and Permeability Variations," Proceedings of the Third EPRI Balance–of–Plant Heat Exchanger NDE Workshop, Jun. 6–8, 19994, Myrtle Beach, South Carolina, USA.

David Mackintosh, "Remote Field Signal Interpretation in Small–Bore Ferromagnetic Tubes," Proceedings of the Third International Conference on the Remote Field Eddy Current Technique, Aug. 30 & 31 1994, Queen's University at Kingston, Ontario, Canada.

David Mackintosh, "Remote Field Eddy Current Inspection of Ferromagnetic Tubes," Proceedings of the ASNT 1994 Fall Conference and Quality Testing Show, Atlanta, GA, Sep. 19–23, 1994.

Harold Smith, David Mackintosh, "Remote Field Eddy Current Examination of Boiler Tubes," Proceedings of the EPRI Topical Workshop: Electromagnetic NDE Applications in the Electrical Power Industry, Charlotte, NC, USA, Aug. 21–23, 1995.

David Mackintosh, "Remote Field Eddy Current Examination of Heat Exchangers," Proceedings of the EPRI Feedwater Heater Technology Symposium, Sep. 25–29, 1995, Kansas City, MO, USA.

David Mackintosh, Adrian Banica, Jens Winslow, "Advanced software for RFEC defect signal analysis in boilers and heat exchangers," Proceedings of the NACE Canadian Region Western Conference, Anchorage, Alaska, Feb. 19–21, 1996.

David Mackintosh and David Atherton, "Evaluation of Superimposed Flaws Using the Remote Field Eddy Current Technique," Proceedings of the ASNT Spring Conference, Houston, Mar. 17–21, 1997.

David Mackintosh, "Field experience with the Remote Field Eddy Current Data Display," Proceedings of the Fourth International Conference on Remote Field Technique, Kingston, Ontario, Canada, Aug. 26 & 27 1997.

David Mackintosh, Jim Yukes, and Paul Ryhanen, "Remote Field Examination of Heat Exchanger Tubes," Proceedings of the ASNT Fall Conference, Pittsburgh, Pennsylvania, Oct. 20–24, 1997.

"CERF Conducts New Technology for the Public Works Community," *Cerf Currents*, vol. 97.3, Fall 1997.

Russell, D.E., and A.T. Davies, "Condition Evaluation Technology for Water Main Asset Management," AWWA Annual Conference, Atlanta, Georgia, Jun. 1997.

Staples, L.B., A New Tool for Condition Evaluation of Cast and Ductile Iron Pipe, The NACE Int'l Annual Conf. and Exposition, Paper No. 45, 1996.

Staples, L.B., "New Tools for the Condition Evaluation of Waterlines. Seminar on Trenchless Technology: Undergroud Infrastructures: the Sick Waiting to be Diagnosed," Centre d'expertise et de Recherché en Infrastructure Urbanes, Montréal, Québec, Dec. 1994.

Staples, L.B., "New Tools for the Condition Evaluation of Waterlines," Centre d'expertise et de Recherché en Infrastructure Urbanes, Montréal, Québec, Sep. 1995.

Winslow, J.C., and D.L. Atherton, "High Resolution Detectors for Remote Field Current Probes," *CSNDT Journal*, vol. 16, No. 5, Sep.–Oct. 1995, pp. 8, 10–13, 22–25.

"History of the Remote–Field Eddy Current Inspection Technique," by T.R. Schmidt, *Back to Basics, Material Evaluation/47*, Jan. 1989.

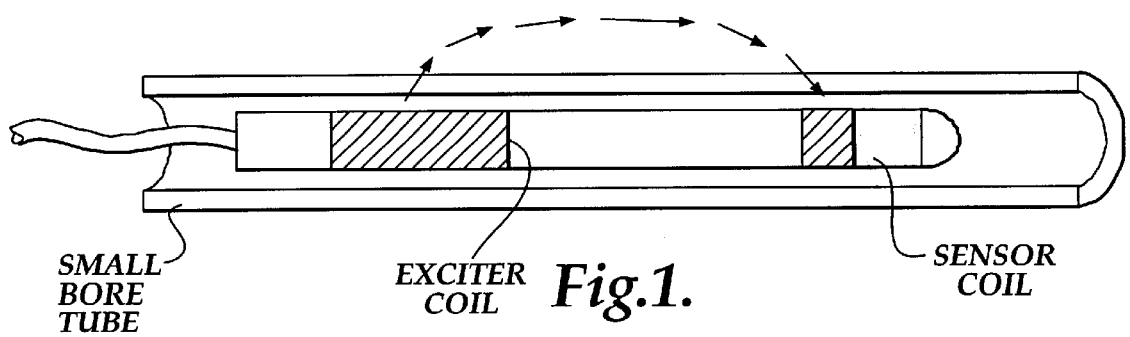
Fig.1.
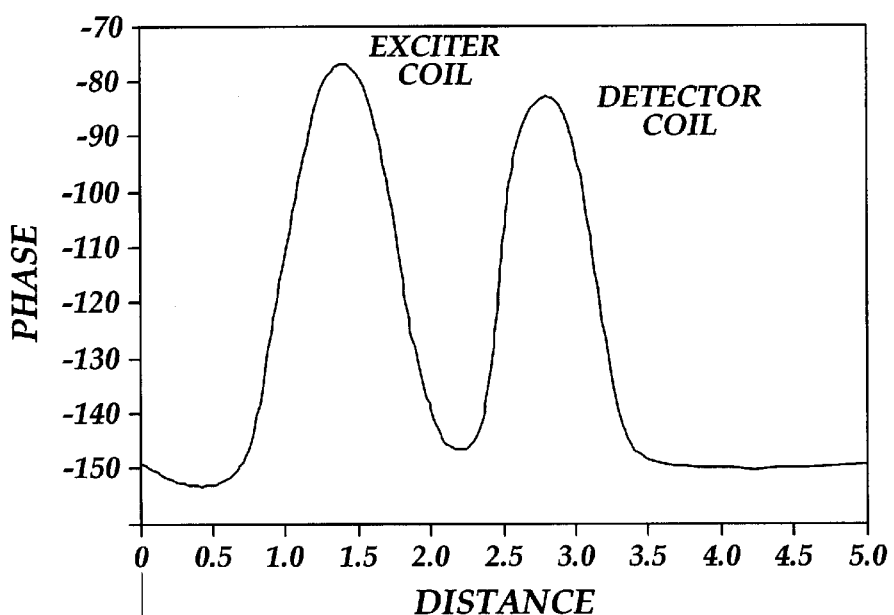
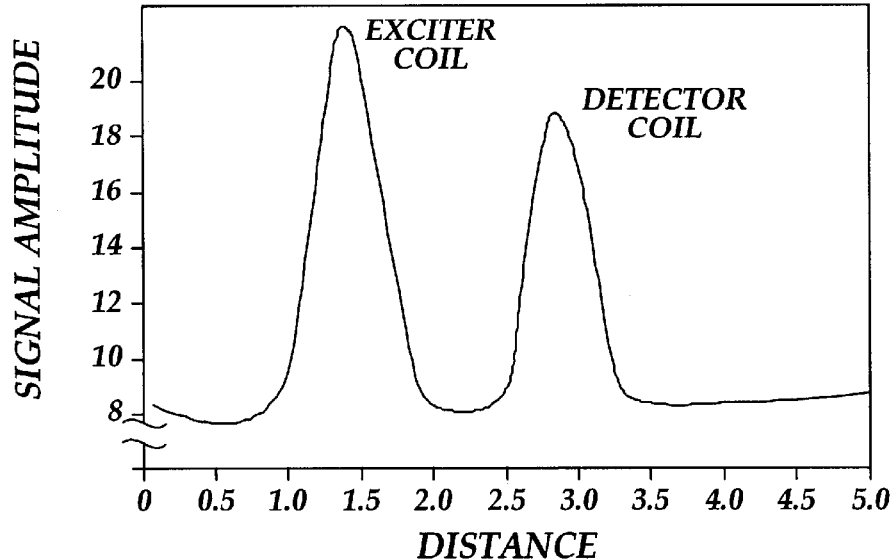
Fig.2.

*Fig.8.* MULTI-DIMENSIONAL FILTER

LOCATE NON-ANALYZABLE FEATURES

LOCATE SIMILIAR TRACES IN DATA

DETERMINE NOMINAL VALUE

DETERMINE PHASE PROFILE

LOCATE DEFECTS

CALCULATE TOTAL EQPS

DETERMINE CALIBRATION $EQPS_{CAL}$

ANALYZE DEFECTS IN PIPE LENGTHS

MAIN MENUBAR

TOOLS OPTIONS

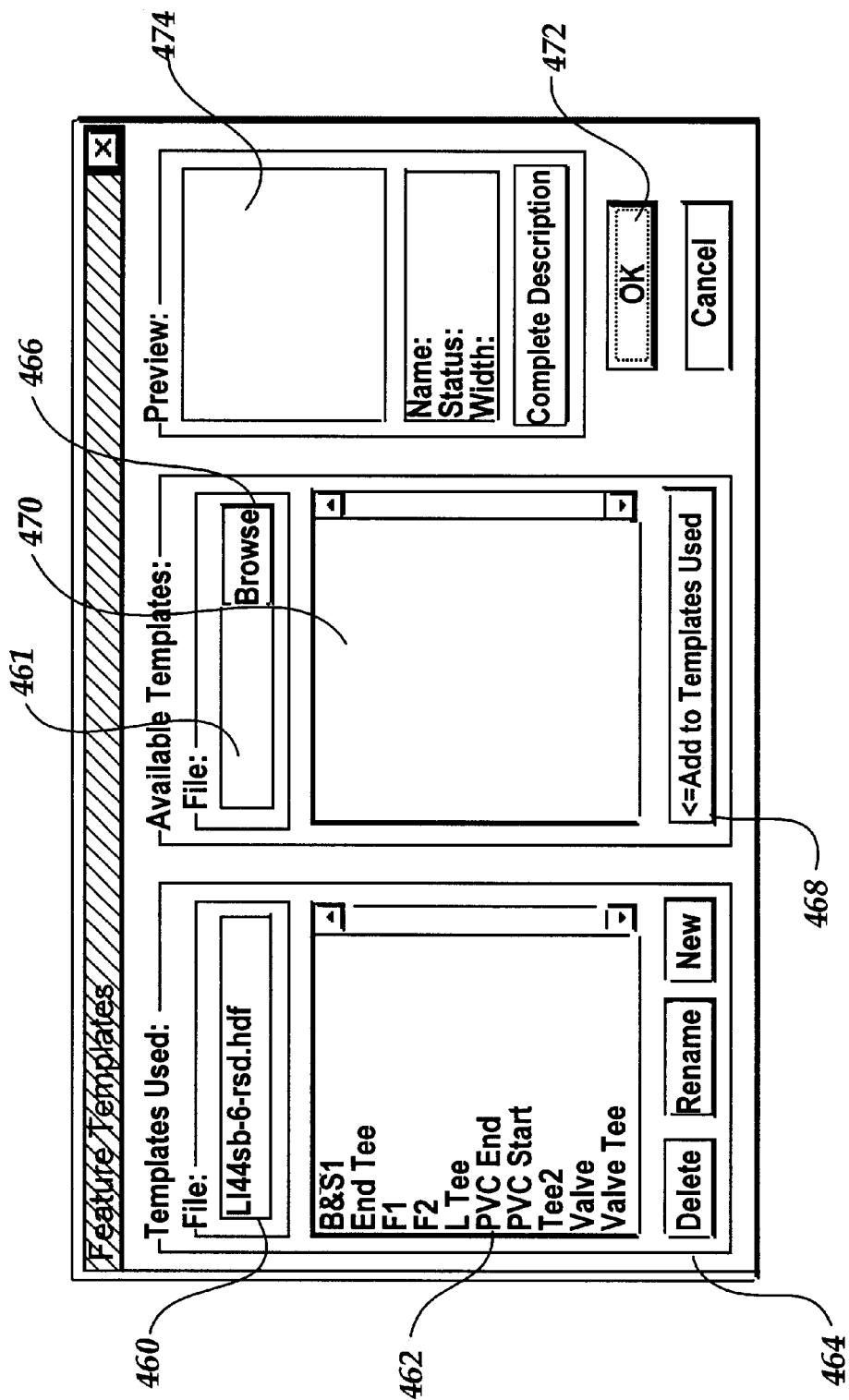
Fig.22. SELECT FEATURE TEMPLATES

*LOCATE FEATURES*

PREPARE JOINTS FOR ANALYSIS

PREPARE DEFECT AREAS FOR ANALYSIS

ANALYZE DATA

SORT/FILTER RESULTS                                    ☒

☐ SORT /FILTER FEATURES
SORT CRITERIA    ⦿ ASC    ☐ MAX. SHOWN    ☐ THRESH. VAL.
[LOCATION ▼]     ○ DES    [0      ▲▼]     [              ]
                 THRESHOLD RANGE: 0 TO 286.48

☑ SORT /FILTER JOINTS
SORT CRITERIA    ⦿ ASC    ☐ MAX. SHOWN    ☐ THRESH. VAL.
[LOCATION ▼]     ○ DES    [0      ▲▼]     [              ]
                 THRESHOLD RANGE: 0 TO 286.49

☑ SORT/FILTER DEFECTS WITHIN EACH JOINT
SORT CRITERIA    ⦿ ASC    ☑ MAX. SHOWN    ☐ THRESH. VAL.
[DARW    ▼]      ○ DES    [5      ▲▼]     [              ]
                 THRESHOLD RANGE: 48.760 TO 122.475

☐ LOCATION FILTERING CRITERIA
[BY LOCATION ALONE ▼]  MOST SIGNIFICANT   [0]   [INDEX ▼]
                       DEFECT IN RANGE

[ DEFAULT ]    [ OK ]    [ CANCEL ]

*Fig.37.*

COIL RESPONSE, G (N)    THEORETICAL DEFECT SIGNAL, F(N)    F(N) AND G(N) CONVOLUTES TO C(N), OUR ACTUAL SIGNAL

METHOD AND SYSTEM FOR DETERMINING PIPELINE CIRCUMFERENTIAL AND NON-CIRCUMFERENTIAL WALL LOSS DEFECTS IN A WATER PIPELINE

FIELD OF THE INVENTION

The present invention relates to ferrous pipelines, and more particularly, to systems for determining the location of defects in ferrous pipelines, such as water pipelines or sewage lines, based on inputs of non-destructive evaluation (NDE) remote field technique (RFT) data. (also known as remote field eddy current, RFEC, data).

BACKGROUND OF THE INVENTION

Pipelines, such as water mains and sewers, are vital to the quality of life of individual citizens and to the economic productivity of society. Over time, water pipelines will deteriorate, and eventually, they will fail entirely. Keeping these lines operable is a challenge faced by every community, both in terms of maintenance and repair costs and in terms of engineered capacity. In meeting these challenges, it is essential to have accurate information on the condition of the pipeline. Traditionally, communities have relied on indirect methods of deterioration detection, e.g., visible leaks, soil corrosion potential, statistical pipe break frequencies, pressure drops, soil settlement, etc., or by manually exhuming a portion of the pipeline in order to extrapolate the condition of the entire pipeline.

More recently, a technology has emerged that measures the condition of water pipelines in a more accurate and non-destructive manner. This technology borrows aspects of knowledge available from current small-bore ferromagnetic tube analysis. In particular, a remote field technique (RFT) measurement device is used to evaluate the wall thickness of the larger ferromagnetic water pipes, Such as those used in municipal water systems, using remote field technique.
Small-Bore Ferromagnetic Tube Analysis As background information and referring to FIG. 1, a typical small-bore RFT measurement device includes an exciter coil and a sensor coil, separated by a distance of ~2 or more pipe diameters. A probe is inserted into and pulled through a ferrous tube. The exciter coil is energized with a low frequency (100–300 HZ typical) alternating current that creates an alternating magnetic field, a portion of which travels within the tube and a portion of which travels outwardly through the tube walls. The alternating magnetic field traveling within the tube is rapidly attenuated due to eddy currents induced in the tube wall. The portion that passes outward through the tube walls propagates along the tube exterior and is attenuated less rapidly. At some point, the inside field is weaker than the outside field (usually past ~2 or more pipe diameters), and part of the outside field propagates back into the pipe, and can be measured by the detector coil.

Thus, the measured electromagnetic field has passed through the tube wall twice, once propagating outward at the exciter coil, and once propagating inward at the detector coil. With each passage through the tube walls, the signal is reduced in strength and delayed (i.e., signal transit time is increased.) Changes in wall thickness will affect the amount of transit time taken for the signal to go from the exciter coil to the detector coil, which can be measured as a phase shift in the returning electromagnetic field. In addition, the strength of the field will also be altered, which is measured as a signal amplitude change. As the measurement device travels along a body of tube, the detector signal's phase and amplitude are determined by the RFT instrument and are digitally recorded and/or displayed in strip chart form. FIG. 2 is an example of such strip chart data. The information of FIG. 2 is from the article Remote Field Eddy Current Analysis in Small-Bore Ferromagnetic Tubes, by David D. Mackintosh, David L. Atherton, and Sean P. Sullivan, in Materials Evaluation, Vol. 51, No. 4, April 1993, pp. 492–495, 500.

In small-bore ferromagnetic data analysis, an analyst will first obtain signal calibration information from a sample tube, preferably identical in size and material to the tube in question. By machining various known defects in the sample tube, pulling an RFT measurement tool through the sample tube, and then measuring the resulting RFT data signals, the analyst will develop a baseline or library of data values for known defects.

After obtaining calibration data, the analyst passes the measurement device through the tube of interest. The measurement data is visually displayed and/or printed in strip chart form. The analyst determines nominal signal values for phase and amplitude by inspection of the strip chart data. Any recurring, relatively flat, data segments are likely tube segments without defects, and therefore representative of nominal signal values.

The analyst next identifies potential defect signals that will require further analysis. At each potential defect signal location, evaluation of its type is made, including a determination of whether the defect is circumferential or one-sided pitting and a determination of the defect length (long or short) relative to the spacing between the exciter and the detector which affects the method as calculation in RFT analysis. Often this evaluation is made using a polar type plot of the values of phase and amplitude for a select portion of the measurement data. The polar plot of FIG. 3 illustrates one type of polar plot in a voltage plane. In the voltage plane, the data is displayed in polar form, with the axis scaled and rotated so that the Cartesian coordinate (1,0), or $1\angle 0°$ in polar form, represents the nominal data signal. The positive X-axis represents the 0° degree change of signal phase from nominal signal and counter-clockwise rotation direction indicates an increase in phase, such as would occur with a decrease in wall thickness. Because there are phase and amplitude values for each total circumferential wall thickness, there exists a theoretical Reference Curve, labeled "Reference Curve" in FIG. 3 that defines the theoretical signal values for decreasing uniform circumferential wall thickness.

Based on the change in the phase and amplitude at the defect with respect to the nominal signals, it is possible to determine the metal loss and circumferential defect extent using the calibration information, the skin-depth equations, and the mathematical theory of RFT analysis. The amount of metal loss can then be correlated to actual physical dimensional changes in the tube wall thickness.

To ease the task of plotting RFT measurement data for small bore tubes, a software tool (termed ADEPT) was invented in the early 1990's. The ADEPT tool is capable of displaying the small-bore ferromagnetic tube RFT data on a computer monitor in various forms. The ADEPT tool requires the analyst to select a particular portion of the data stream, to enter a calibration amount, and to supply a nominal signal value. Using this information, the ADEPT tool plots the defect trace in voltage plane polar form. The defect trace of the polar plot in FIG. 3 is shown in FIG. 4 as it would appear in ADEPT on the voltage plane. The voltage plane data in the ADEPT display has been rotated and normalized so that the nominal signal occurs at a position (1, 0) Cartesian or 1∠0° polar in the voltage plane polar plot. The Reference Curve is displayed to indicate the theoretical trace a uniform change in wall thickness would cause, which aids in defect pitting evaluation.

The analyst plots a select portion of the signal data using ADEPT and then visually searches for shapes that are similar to known defect shapes. Various characteristic shapes represent certain types of defects or other anomalies. For examples of specific shapes, see the article Remote Field Eddy Current for Examination of Ferromagnetic Tubes, by David D. Mackintosh, David L. Atherton, Thomas R. Schmidt, and David E. Russell, in Materials Evaluation, Vol. 54, No. 6, June 1996, pp. 652–657. In FIG. 4, the plot of the phase and amplitude values of FIG. 3 results in an elongated loop shape representing one-sided pitting.

At each selection data portion, the analyst can request ADEPT to calculate the remaining wall thickness based on information about the defect. The information about the defect must be supplied to the ADEPT program. Example types of information include the calibration information, nominal signal values, defect signal values, etc. Depending on the defect length, and particularly whether the length is shorter or longer than the sensor/exciter separation distance, two results are possible.

The analyst must choose the correct result by identifying the length of the defect from the strip chart. Finally, the analyst uses his or her previous experience to judge tile accuracy of the results. If necessary, the analyst will re-evaluate the data, particularly tile selection of the nominal value, calibration signal values, and exact location of defect, as these greatly affect the resulting, wall loss amounts. The ADEPT software thus helps a user to manipulate large amounts of RFT raw data into various visual forms and to quantify potential wall thickness loss.

Even though ADEPT is a significant tool for use with RFT analysis, it does not include programming that provides structured analysis or advisory information regarding the data. Thus, ADEPT has the disadvantage of still requiring an experienced analyst to select the potential defect location, select the calibration and nominal values, to interpret the ADEPT output information, and ultimately, to verify the validity of the results.

Manual Water Pipeline RFT Analysis

Recently, a RFT measurement device has been developed for use with large water lines. See U.S. Pat. No. 5,675,251. However, the methodology of analyzing the small-bore ferromagnetic tube is not directly applicable to the larger water lines. In particular, water pipelines are invariably located underground and are frequently inaccessible (such as those beneath buildings or under roadways). This makes it difficult or impossible to obtain calibration data and to determine nominal signal values using small bore RFT. The problem is exacerbated by the fact that many of the underground water pipelines in use today were made using casting techniques that are no longer used and for which sample pipe pieces are no longer available. In the absence of calibration and nominal signal data, analysts have to assume known defects from the inspection data. An example would be the distinct signal from a section of PVC pipe in the line that could be assumed to be a 100% circumferential loss (sinice PVC is not ferrous pipe). If a PVC reading is not available, the analyst may use data from a different pipeline pull of a similar material. Analysts have also borrowed calibration data from pulls of pipelines in the same geographic vicinity. These techniques have resulted in variable and sometimes inaccurate results.

A second problem with attempting to apply small-bore ferromagnetic tube analysis to larger water pipelines is the sheer volume of data that is to be analyzed. Typical runs of small-bore tubes are in the range of about 3 meters to about 15 meters. In contrast, a municipal water pipeline system may be several kilometers long. For one embodiment of an RFT inspection tool, the data log produced is recorded at approximately 1.5 mm intervals (roughly 200 data points per foot). This results in copious amounts of signal data available for use in evaluating the condition of cast and ductile iron pipe. The task of manually interpreting and processing this data is therefore tedious and labor intensive, Locating and analyzing each potential defect, even if done with the aid of ADEPT, requires an enormous amount of time. In addition, the manual method of interpretation is somewhat subjective, being greatly dependent on the analyst's prior education and experience.

Thus, a need exists for an automated analysis system for converting RFT raw data into information that is immediately useable by systems engineers who are less experienced and for manipulating the data in a manner that produces more consistent conclusions. The system should not only convert RFT raw data into polar plot form, but should also locate, identify, and quantify defects revealed by the raw data. The system should decrease the potential for error by using a structured approach to selecting calibration and nominal signal values. This approach should be based on objective criteria reflecting the most current theoretical and practical understandings of PFT data analyses in order to provide all users with accurate and reliable processed data information. The present invention is directed to fulfilling these needs.

SUMMARY OF THE INVENTION

In accordance with the teachings of the present invention, a method is provided for analyzing RFT data from a data file. The method includes parsing the data file into pipe length is, calculating a phase profile for the data points within each pipe length, locating potential defects in the pipe length using the Phase Profiles, determining for each defect a total equivalent phase shift as a combination of a circumferential equivalent phase shift and a non-circumferential equivalent phase shift, and using the total equivalent phase shift to analyze the defect.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein FIG. 1 is an illustration of the flow of electromagnetic energy in a remote field technique (RFT) inspection device for small bore tubes;

FIG. 2 is an example strip chart plot of RFT phase and amplitude data collected from an example water pipeline pull;

FIGS. 18–47 are computer display illustrations showing various aspects of one embodiment of a computer program formed in accordance with the present invention, FIG. 18 is an illustration of a computer display having a selectable Main Menubar;

FIG. 19 is an illustration of a computer display having a strip chart that shows example data;

FIG. 20 is an illustration of a computer display with a drop-down menu provided under a "Tools" heading;

FIG. 21 is an illustration of an interactive computer display window regarding data filtering, smoothing and decimating;

FIG. 22 is an illustration of an interactive computer display window regarding templates;

FIG. 23 is an illustration of an interactive computer display window for use in selecting templates;

FIG. 24 is an illustration of an interactive computer display window for use in locating templates matches in file;

FIG. 25 is an illustration of a computer display showing a template matching report;

FIG. 26 is an illustration of an interactive computer display window for use in preparing joint data for analysis;

FIG. 27 is an illustration of a computer display window showing a histogram of phase values and a nominal phase amount;

FIG. 28 is an illustration of an interactive computer display window for use in preparing defect areas of analysis;

FIG. 29 is an illustration of an interactive computer display window regarding calibration data;

FIG. 30 is an illustration of a computer display window showing a histogram of defect EQPS values and a suggested phase calibration amount;

FIG. 31 is an illustration of a computer display with a drop-down menu provided under a "Display" heading;

FIG. 32 is an illustration of an interactive computer display window regarding stripchart preferences;

FIG. 33 is a second illustration of an interactive computer display window regarding stripchart preferences;

FIG. 34 is an illustration of a computer display window showing portions of a strip chart and a template match location;

FIG. 35 is another illustration of a computer display window showing portions of a strip chart and defect analysis results;

FIG. 36 is an illustration of a computer display window of a defect summary display;

FIG. 37 is an illustration of an interactive computer display window regarding sort and filter results;

FIG. 38 is an illustration of a computer display with a drop-down menu provided under a "View" heading;

FIG. 39 is an illustration of an interactive computer display window of a strip chart display, a voltage plane plot, a defect data spreadsheet, and a display that shows analysis results;

FIG. 40 is a logic diagram regarding voltage plane display changes;

FIG. 41 is an illustration of an interactive computer display window showing joint display options;

FIGS. 42 and 43 are logic diagrams regarding calculation and display of GIS data;

FIGS. 44 and 45 are illustrations regarding deconvolution information;

FIG. 46 is an illustration of a computer display showing a layout of pipe data; and FIG. 47 is an illustration of calculated and defined GIS points.

DETAILED DESCRIPTION OF THE PREFERRED EMBODIMENT

Figure 5:
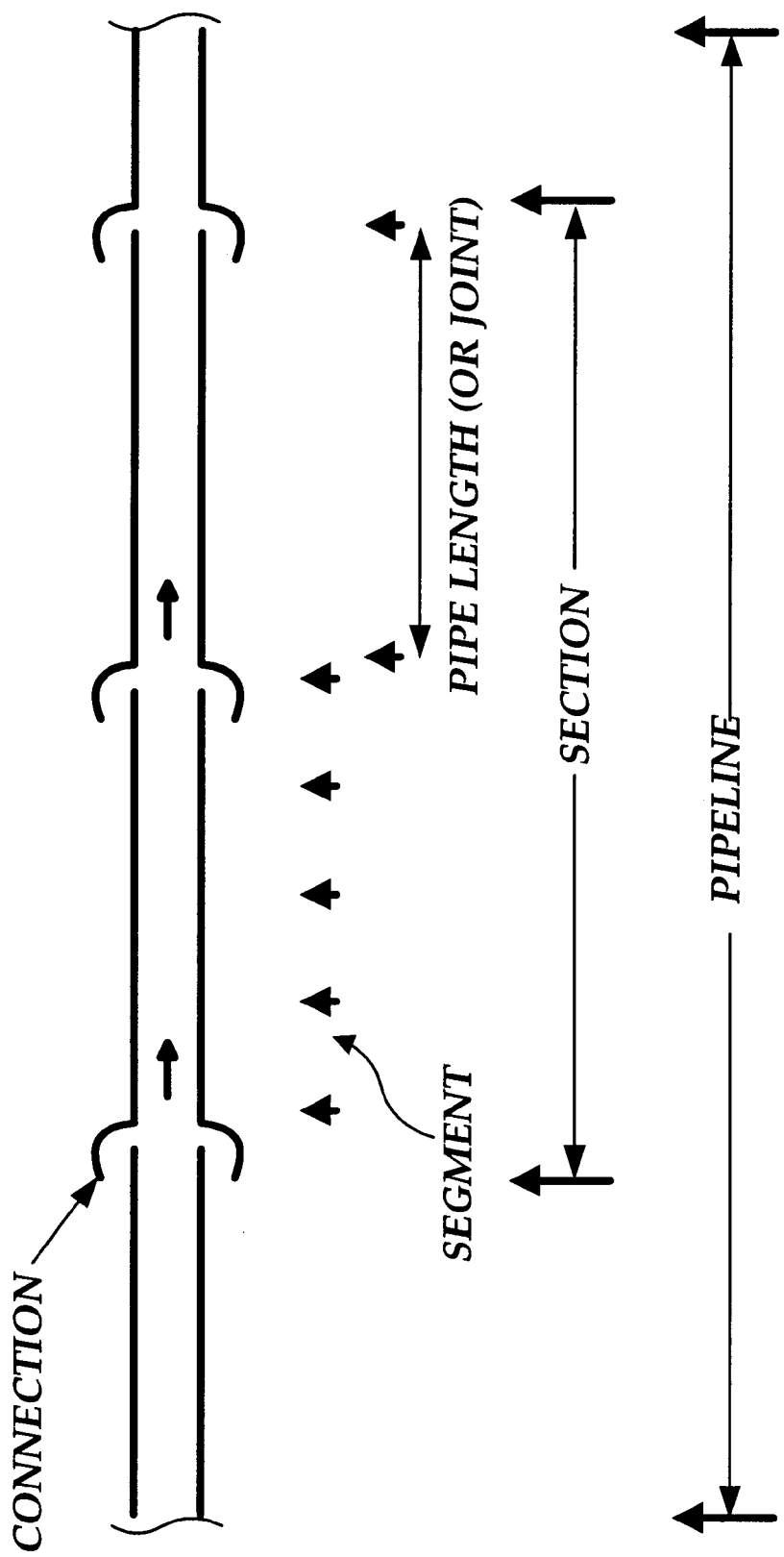
FIG. 5 is an illustration of terminology used herein.

The paragraphs below include a first section describing a unique method of RFT analysis formed in accordance with the present invention. Following, is a description of one embodiment of this method as provided in a novel computer program. Referring to FIG. 5, various words are defined and used herein as follows. "Pipeline" refers to the entire length of a pipe. "Pipe length" or "joint" is a single portion of pipe, from a bell at one pipe end to a spigot at the other pipe end. "Segments" or "sub-segments" are lengths of pipe that are less than the pipe length. "Section" is a specific length of pipeline having a number of pipe lengths. "Connection" is the combination of one pipe's spigot with another pipe's bell.

Method of Analysis

Figure 6:
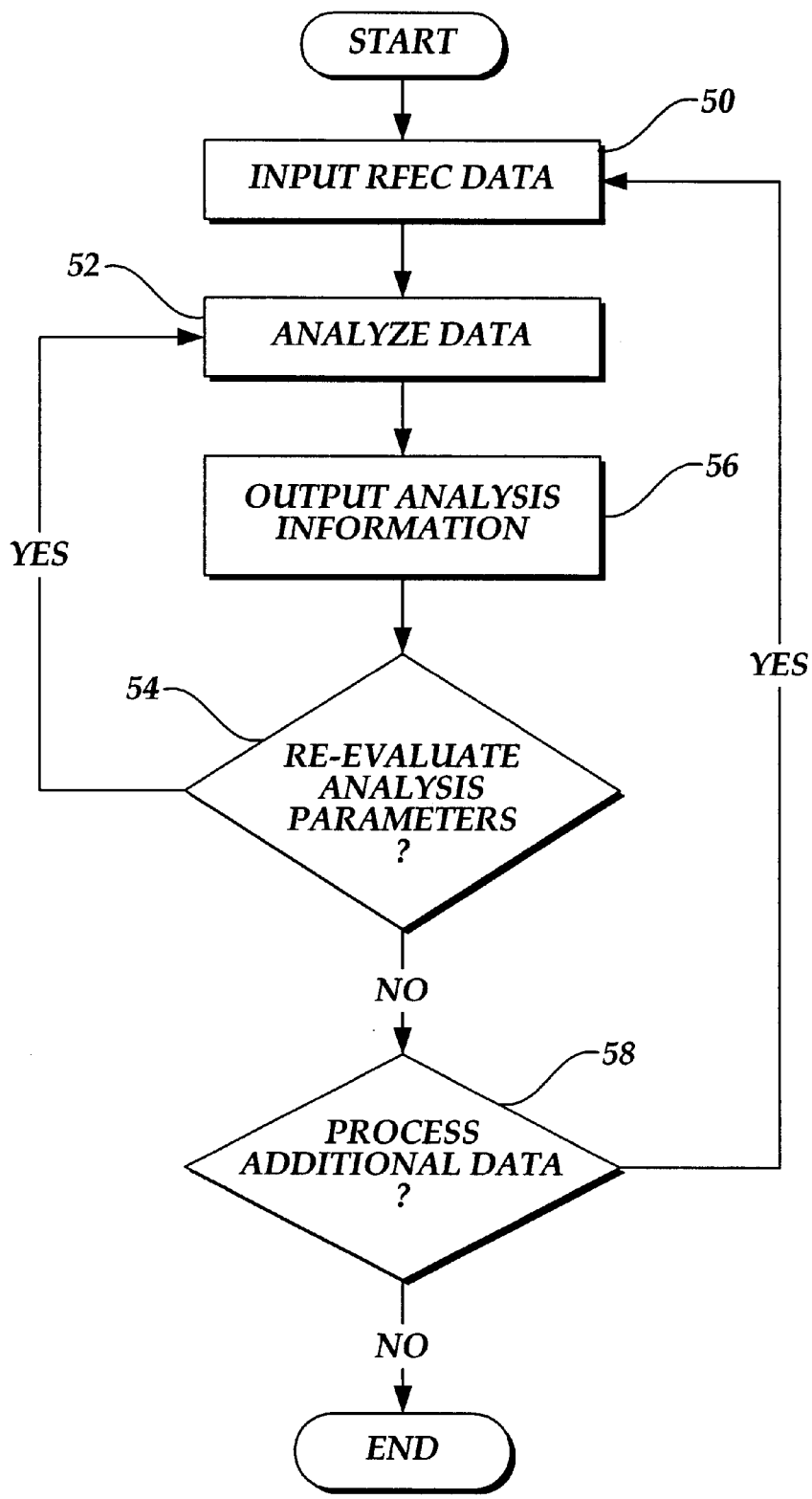
FIG. 6 is a flow chart of a method of RFT analysis formed in accordance with the present invention.

Referring to FIG. 6, RFT signal data is obtained from an RFT pipeline measurement inspection device and is provided as an input to the present invention method at a block 50. (RFT data is also known as remote field eddy current, or RFEC, data.). The data is analyzed at a block 52 to determine the location of likely defects and to determine the amount of remaining pipeline wall thickness left at each defect. The analysis results are saved and are provided to the operator in various report forms at a block 56, e.g., on a display screen, on an electronic data storage medium, on a paper printout, etc. Various decision blocks (e.g., 54 and 58) are provided for the user to re-evaluate analysis parameters and/or process additional data.

Figure 7:
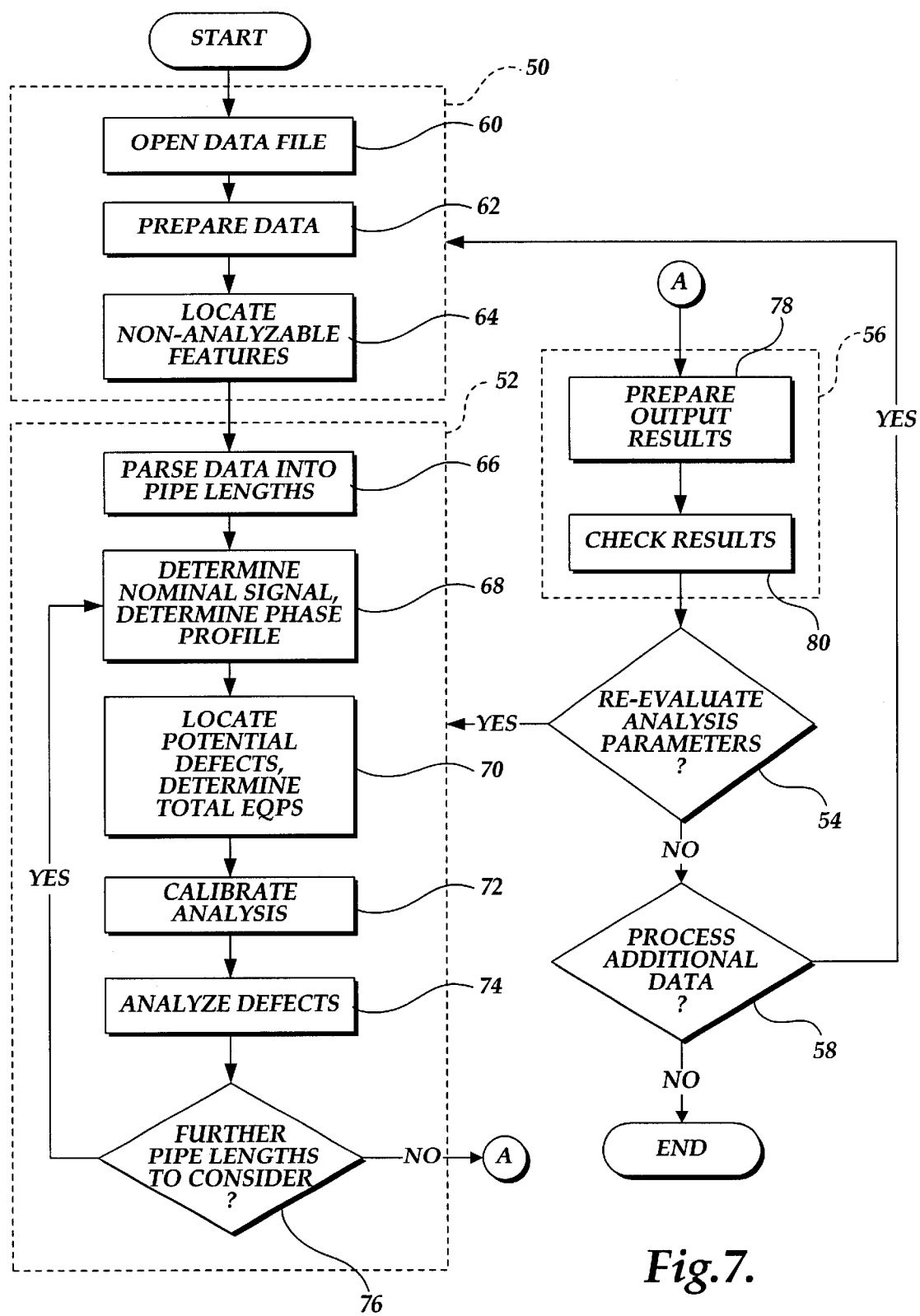
FIG. 7 is a more detailed illustration of one embodiment of the method of FIG. 6.

FIG. 7 illustrates in more detail one embodiment of the method of RFT analysis performed in accordance with FIG. 6. Many of the features described with reference to FIG. 7 are from the perspective of having been implemented in a computer program. This is meant to be illustrative and not limiting, since the main features of the present invention method can be accomplished manually.

Within block 50, an RFT signal data file is opened at a block 60 and is prepared for use in later manipulations at a block 62, The location of various non-analyzable features in the data are determined and are parsed out at a block 64. The data is then analyzed within block 52, where the logic proceeds to a block 66 where a determination of the location of discrete pipe lengths is made for the entire data file.

For a subject pipe length, a nominal signal and a Phase Profile are determined at a block 68. A Phase Profile is a set of phase values determined for the analyzable area of each joint, selected to represent theoretical phase value at a given location, if no one-sided, non-circumferential, pitting loss was present (i.e., the expected signal phase if only circumferential wall thickness variation is considered). Tile logic then proceeds to a block 70 where potential defects within the pipe length are identified at a block 70. A Total EQPS signal is also determined for each potential defect in the pipe length at block 70. Eddy current equations show that for circumferential metal loss the change in signal phase is linearly related to loss (as long as material properties and frequency remain constant). RFT analysis allows one to determine the theoretical phase shift caused by a circumferential defect of equivalent depth of a one-sided non circumferential pitting defect. The equivalent phase shift (EQPS) of a pitting defect with a given nominal phase and amplitude signal, and a given phase and amplitude shift, would be the same phase shift as that of a fully circumferential defect of equal depth, which the eddy current equations show is linearly related to detect depth/metal loss. Calibration amounts for the pipe length are determined at a block 72, and defects of interest are analyzed at a block 74. The logic advances to the next pipe length at a decision block 76. In an alternative arrangement of block 52, each of tile tasks in blocks 68, 70, 72, and 74 may be accomplished on all pipe lengths before proceeding to the next task Continuing, the analysis information is output within block 56, starting with preparing the output results from the analysis at a block 78. The results are made available for inspection and/or verification by the operator at a block 80. The output information preferably includes the location and type of potential defects, and the average and minimum wall thickness remaining at each defect. In addition, the operator is provided with opportunities (such as is provided at decision block 54) to redo the data analysis based on altered analysis parameters.

Prepare RFT Data For Analysis

The amount of initial data manipulation required will depend oil the type of raw data being used. For the purposes of discussion below, it is assumed that the raw data is in the form of a computerized list of in-phase and quadrature values created by an RFT measurement device based on its detector coil recordings. In-phase and quadrature values are the rectangular coordinates of a polar point. For example, a polar signal of $5\angle 53°$ can be represented in Cartesian coordinates as (4, 3). The in-phase component would be 4 and the quadrature component would be 3. The in-phase component indicates how much of the received signal is the same as the exciter signal, and the quadrature component indicates how different the received signal is from the exciter signal. The in-phase and quadrature data could also be represented in polar form as a phase and amplitude, defined by X=amplitude * cos(phase), and Y=amplitude * sin (phase). The in-phase and quadrature forms are preferred for ease of filtering and are the simplest output form available from the tool's digital signal processing function.

It is preferable for an operator to first visually inspect a list or plot of the raw RFT data to verify data quality and to determine whether the run was successful. The recorded traces should have a number of similar recurring shapes (as would be recognizable to experts as representing bell-and-spigot connections). The traces should have minimal (or no) large noise spikes, that appear as sharp, short, erratic jumps in data value. Further, the data values should include relatively smooth transitions.

If the raw data has distracting shifts of approximately 360 degrees in the phase, phase wrapping may be the cause. Phase wrapping happens when the phase passes from +180 degrees to −180 degrees, or vice versa, and can prevent accurate analysis. For example, when phase is at 179° and a relative defect phase change of 3° occurs, a positive 182° phase should result. However, only a range of ±180° can be easily represented, thus causing a result of −178°. Since calculations are based oil relative changes in the phase and amplitude, phase wrapping should preferably be corrected.

Correction of phase wrapping is accomplished by rotating the zero degree reference of the phase so that the relative changes no longer cross the ±180 degree point. A rotation of 180 degrees will usually overcome the problem if present. It is further preferable that all wrapping be corrected automatically either by the RFT measurement device or during preparation of the input data, without the need for operator prompting. One method to remove and/or minimize phase flipping is to use the average in-phase and quadrature values to determine if rotation of −90, 0, +90, or +180 would place the average phase as close to 0° as possible, and then proceed to rotate the data that amount, if appropriate.

Once the data is verified, it is filtered, smoothed, and decimated prior to analysis at block 62 in FIG. 7. Filtering reduces the amount of extraneous noise in the data. Smoothing further reduces erratic movement of the data values. Decimating is a method of representing the raw data using fewer data points, thus reducing the total volume of data being manipulated, the resolution of known water pipeline RFT measurement devices being of much higher resolution than is needed for analysis. Decimation is a means of reducing the volume of data by reducing the spatial sample resolution from X samples per foot to X/D samples per foot where D is the decimation factor. By initially performing these steps, the data quality is improved and the subsequent analysis can be accomplished at a faster rate.

In one embodiment, filtering is accomplished using a median filter to remove noise spikes from the data. One simple example median filter uses an odd-sized fixed data range within which to select a median value. The fixed data range is applied through the entire raw data set to produce a filtered data set having only the median values of each applied fixed data range.

By way of example, for a fixed data range of 3 and a fictitious raw data set of 7 values [1, 14, 3, 4, 5, 8, 9] results III the following applied data ranges and median values shown in TABLE 1. Duplicate data elements are used at each end to result in a number of median values equivalent to the number of elements in the raw data set.

TABLE 1

| Applied Data Range | Median Value |
|---|---|
| (1, 1, 14) | 1 |
| (1, 14, 3) | 3 |
| (14, 3, 4) | 4 |
| (3, 4, 5) | 4 |
| (4, 5, 8) | 5 |
| (5, 8, 9) | 8 |
| (8, 9, 9) | 9 |

Thus, the set of median values becomes the filtered data set. Any spikes (or legitimate defect readings) composed of less than half as many data points as the data range are completely removed. Noise spike signals, which are typically shorter than the data range, are attenuated. Too large of a data range should not be used, since real defect data may be inadvertently removed or distorted. Since this filter is computationally intensive, the smallest filter level (fixed data range) that is effective for the particular application should be used.

Depending on the type of raw data provided, it may be desirable to filter multi-dimensional data points. The example above is a "one-dimensional" example since each element is a single number. To accomplish multi-dimensional filtering, a unique multi-dimensional median filter method is presented herein. In general, this filter uses a fixed data set to step through the raw data. At each step, the smallest total distance between each element relative to all other elements in the applied fixed data set is determined. The element having the least total distance selected as the median element for that applied fixed data set, and is the element most central to the cluster of elements in the set.

Figure 8:
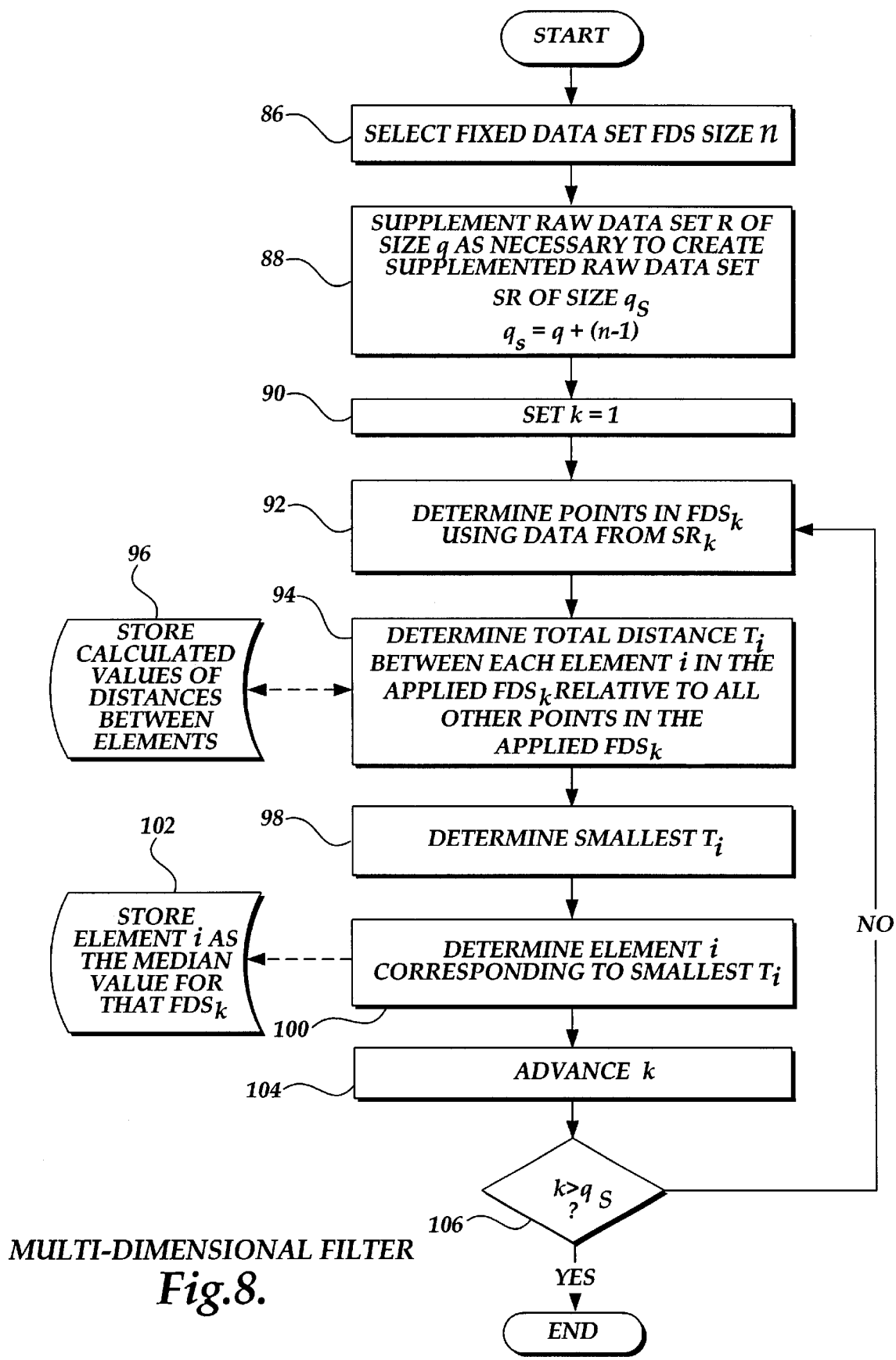
FIG. 8 is a logic diagram of one embodiment of a multi-dimensional median filter.

FIG. 8 illustrates an embodiment of a unique multi-dimensional filtering method. An integer size it is determined for a fixed data set, FDS, at a block 86. A raw data set, R, of size q is supplemented to create a supplemented raw data set, SR, of size $q_s$, where $q_s=q+(n-1)$ at a block 88. A counter k is set to an initial value (e.g., 1 as shown in FIG. 8) at a block 90. Starting at one end of the supplemented raw data set SR, the elements of an applied $FDS_k$ are determined at a block 92. For each element i in the applied $FDS_k$, the total distance $T_i$ between element i and all other points in the applied $FDS_k$ are determined at a step 94.

The individual distances between a particular element i and another element are preferable saved to memory in a block 96 so that later calculations can use them, thereby reducing redundant distance calculations. The smallest value of $T_i$ is determined at a block 98, and the element i corresponding to the smallest $T_i$ is determined in a block 100 and then stored in memory in a block 102 as the median value for that applied fixed data set $FDS_k$. The counter k is advanced at a block 104 and if counter k is determined to be less than the supplemented raw data set SR size at a decision block 106, the calculations for the next $FDS_k$ are determined. This cycle continues through the entire supplemented raw data set SR.

By way of example, for a fixed data range FDS of size n=3 and a fictitious two-dimensional raw data set R of size q=7 having elements [(4,7) (4,5) (5,6) (5,5) (6,4) (10,7) (6,6)], a supplemented raw data set SR of size $q_s=9$ is formed having the elements [(4,7) (4,7) (4,5) (5,6) (5,5) (6,4) (10,7) (6,6) (6,6)]. TABLE 2 list the resulting applied data ranges and median values. Supplemental duplicate data elements are used at each end to result in a number of median values equivalent to the number of elements in the raw data set. For this two-dimensional data set example, the Pythagorean Theorem is used to determine individual distances in which:

$$(x_i-x_j)^2+(y_i-y_j)^2=D_{ij}^2 \quad (1)$$

where $(x_i,y_i)$ is the data point of interest, $(x_j,y_j)$ is another data point in the fixed data set, and $D_{ij}$ is the distance between the two points. Solving for $D_{ij}$ and summing the distances yields the total Distance $T_i$ of one data point relative each of the data points in the fixed data set $FDS_k$.

TABLE 2

$$T_i = \sum_{j=1}^{n} D_{ij} \quad (2)$$

| Applied $FDS_k$ | Applied Data Range | | | $T_i$ For Each Element | Median Data Point (one with smallest $T_i$)* |
|---|---|---|---|---|---|
| $FDS_1 =$ | (4,7) | (4,7) | (4,5) | 2.00, 2.00, 4.00 | (4,7) |
| $FDS_2 =$ | (4,7) | (4,5) | (5,6) | 3.41, 3.41, 2.82 | (5,6) |
| $FDS_3 =$ | (4,5) | (5,6) | (5,5) | 2.41, 2.41, 2.00 | (5,5) |
| $FDS_4 =$ | (5,6) | (5,5) | (6,4) | 3.24, 2.41, 3.65 | (5,5) |
| $FDS_5 =$ | (5,5) | (6,4) | (10,7) | 6.80, 6.41,10.39 | (6,4) |
| $FDS_6 =$ | (6,4) | (10,7) | (6,6) | 7.00, 9.12, 6.12 | (6,6) |
| $FDS_7 =$ | (10,7) | (6,6) | (6,6) | 8.24, 4.12, 4.12 | (6,6) |

*For elements having the same smallest $T_i$, logic must be included to select only one element as the median value. Bold numbers in the third column are the elements selected as having the median data point.

In one embodiment, smoothing is accomplished by averaging the data using a moving block average filter of a size that is at least as big as the multi-dimensional median filter size, and about half as big as the decimation factor, described below. The moving block average filter attenuates defect signals shorter than the filter size. If the raw data is not filtered to remove noise spikes prior to smoothing, a large noise spike may appear as a defect signal once the moving block average filter is performed. Other types of known smoothing techniques may alternatively be used, such as Fourier transforms, weighted averaging, etc.

In one embodiment, decimating is accomplished by first selecting the factor by which the decimation will occur. As used herein, the term "decimating" and "decimation" refer to a reduction in set size by a pre-defined process of elimination where the reduction may occur on the basis of other than every tenth item. Decimating the raw data will reduce the amount of analysis required and quicken its operation.

Several other methods for data decimation exist and may be used, such as Average Value Decimation and Max/Min Value Decimation. According to Average Value Decimation with a size factor of d, an entire data set is parsed into a consecutive string of data sets each of size d. Each set is replaced by its average value. For example, a string of data (1,3,5,1,0,2,7,3, . . . ) with d=4 becomes ([1,3,5,1], [0,2,7,3], . . . ) which then becomes (2.5, 3.0, . . . ). According to Max/Min Value Decimation with a factor of e, an entire data set is parsed into a consecutive string of data sets each twice the size e. Each set is replaced by two values, the maximum value in the set and the minimum value in the set in the order that they occurred. For example, a string of data (1,3,5,1,0, 2,7,3,2,6,5,4,2,2,1,4, . . . ) with d=4 becomes [1,3,5,1,0,2, 7,3], [2,6,5,4,2,2,1,4] which becomes [0,7], [6,1] and finally 0,7,6,1.

When the above steps of verifying, filtering, smoothing, and decimating are completed, the resulting prepared data issued for the remaining method steps.

Locate Non-Analyzable Features

Referring back to FIG. 7, prepared data that appears to reflect non-analyzable elements, e.g., bell-and-spigot connections, tees, elbow, valves, etc., is identified at block 64. Identification of these components will serve to eliminate them from later defect analysis. In preferred embodiments, tile operator first locates and eliminates the bell-and-spigot connections (or other recurring features). Bell-and-spigots mark the length and location of each pipe length, which is important information used in the subsequent defect analysis.

Figure 9:
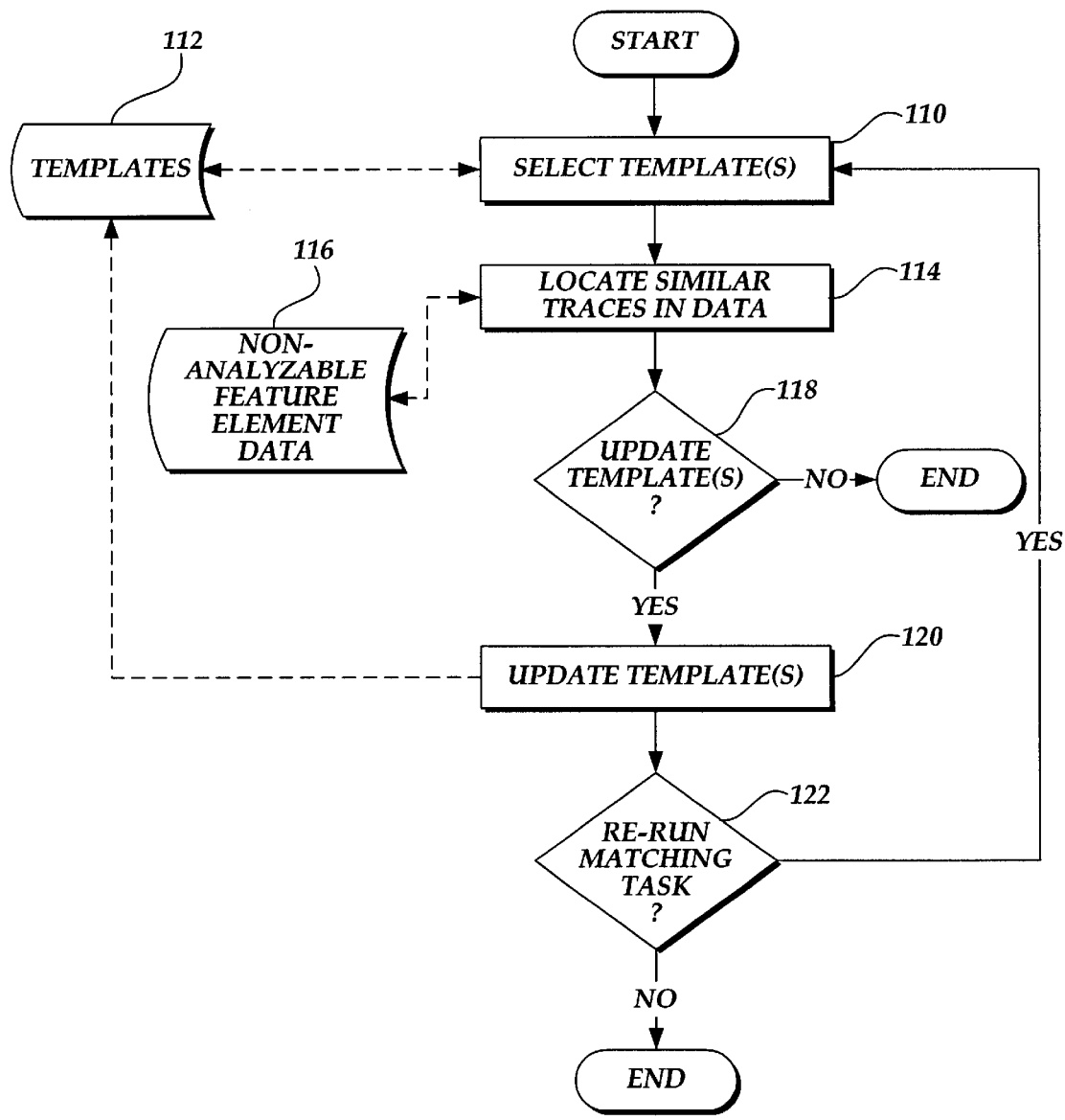
FIG. 9 is a logic diagram of one embodiment of a method used to locate non-analyzable features in a particular pipeline data set.

Referring to FIG. 9 at a block 110, the operator selects one or more stored non-analyzable element templates stored in memory 112 or creates new ones as necessary. The templates can be obtained from various sources, such as by allowing an expert operator to define a segment of the subject data as representing a particular feature. For example, a data length between two points may be set by the operator to be characteristic of an elbow. This method of template forming ensures that characteristics peculiar to that pipeline body are considered. It also allows the more experienced operator to impart knowledge into the analysis.

Since expert analysts are not always available, an alternative preferred method formed in accordance with the present invention is for the operator to select templates from memory 112 that were obtained from previous data files used with regard to that particular pipeline, or similar pipes. This method has the advantage of using pre-defined templates that include characteristics peculiar to that pipeline, its generic type, or similar pipe. The templates selected should correspond to the pipeline diameter being analyzed and the tool diameter used in order to provide an accurate representation of a possible defect. (A template having 200 data points representing a bell and spigot fixture of length 0.5 meters would be unusable for pipe having a diameter of 0.6 meters itself and a potential bell-and-spigot length of 1.5 meters.)

Still referring to FIG. 9, each template is compared with the prepared data to locate similar traces at a block 114. Those comparisons that are closely matched, i.e., a "hit", are flagged and stored in memory for future use at a block 116. The operator is then queried at decision block 118 as to whether lie or she waits to update the stored templates based on the results of the comparisons. If so, the operator updates the templates at a block 120. In preferred embodiments, the operator may define a particular prepared data set as being a new template and add that new template to the stored templates.

Because pipelines differ greatly from one to the other, it is preferred to iterate the template matching step, so that "normal" characteristics of the pipeline itself are used to define what may be a common non-analyzable feature in the specific pipeline. At block 120, new templates are created from the data at locations where a successful, but poor, match with a present template was made (i.e., locations almost missed in matching). In this way, the updated template set is more reflective of the individual template shapes for a particular pipe segment. The user may then request an immediate re-comparison of the prepared data with the updated templates at a decision block 122. Alternatively, a computer program implementation may be arranged to allow the user to pre-select various parameters, such as the type of templates to use initially, the number of templates to add and subtract after each iteration, and the number of iterations to perform.

Figure 10:
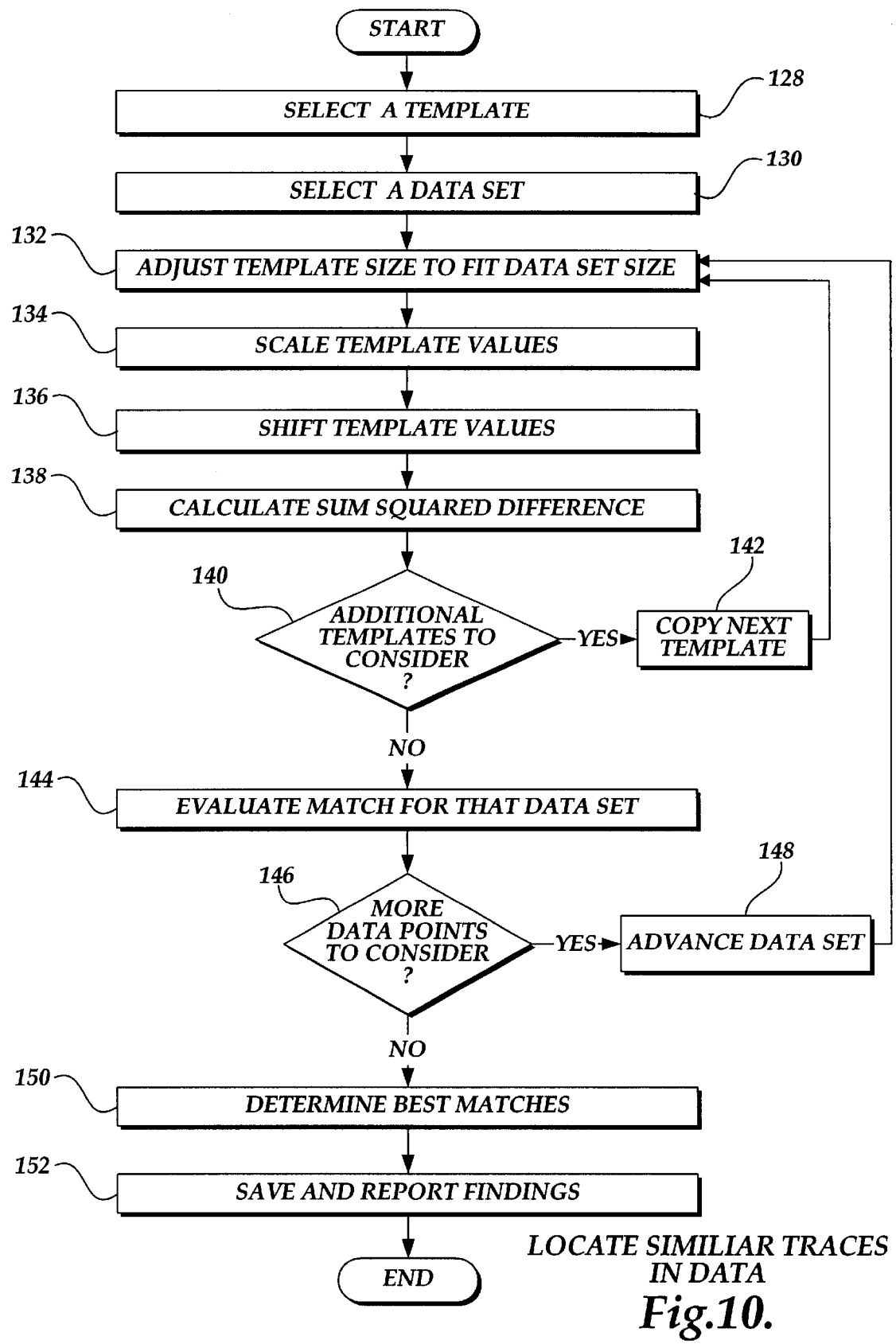
FIG. 10 is a logic diagram of one embodiment of a method used to locate similar traces in data for use with the method of FIG. 9.

The task of locating similar traces in block 114 of FIG. 9 is accomplished in one embodiment using a Match_Difference_Factor illustrated in FIG. 10 based on the summation of differences squared between corresponding data points in the template and the prepared data. Other methods may be used. In more detail and referring to FIG. 10, a selection is made at a block 128 of a single template of interest. A copy of the template is made, including information on its size and shape. Starting at the beginning of the prepared data set, an equivalent amount of data is selected at a block 130.

A size adjustment is made at a block 132 to the template copy to ensure that the number of data points in the template corresponds to the particular number of data points in the prepared data that represents the same length L as represented by the template. For example, a template may have a size of y data points, with each data point $y_m$ having a corresponding phase value $p_m$. A size of y data points corresponds to a physical dimension of length, L. If the number of data points in the RFT data representing a distance L is not y, the number of points representing the template must be changed. For example, if a template has an excess of data points for a given physical distance, logic must be included to cull data points within the template. If the template is found lacking in data points, logic is included to add data points to expand the template to the appropriate size. In one embodiment, this expansion is accomplished by inserting additional data points evenly throughout the template and using a linear interpolation to determine the intermediate phase values.

At a block 134, the template values are scaled. In more detail, a selection of prepared data is made having tile same number of data points as the adjusted template, therefore representing the same physical distance. Tile difference between the maximum and minimum phase values is calculated from the selected prepared data. The difference between tile maximum and minimum phase values of the adjusted template is calculated. The adjusted template phase values are then reduced or enlarged (scaled) so that the adjusted template maximum and minimum phase values are the same as the selected prepared data maximum and minimum phase values. This step preferably includes limits as to the amount of scaling permitted to avoid over-zealous template matching. The adjusted and scaled template is shifted at block 136 so that its overall average phase value and the prepared data's average phase value coincide (both, in represented physical location and in range of values).

For each adjusted, scaled, and shifted template value, the sum of the difference squared between the template data and the actual data at each data point is calculated at a block 138. This value is referred to herein as a Match_Difference_Factor. The smaller the Match_Difference_Factor, the better the match, with zero indicating an RFT match.

At a decision block 140, query is made as to whether there are additional templates to consider at that data location. If so, a copy of the next template is obtained at a block 142 and the logic returns to block 132 to accomplish application of the next template to the particular data location. If all templates have been considered at decision block 140, evaluation is made of the template matches for that data location at a block 144. In one embodiment, all Match_Difference_Factors for a specific data location are compared, with the minimum Match_Difference_Factor being saved as the best match.

If additional data points are yet available for template analysis at a decision block 146, the data set is advanced at a block 148 and the process of applying all selected templates to that next data set is performed.

Once the selected templates have been applied to all data points, the various Match_Difference_Factors are scanned to locate the smallest values at a block 150. In one embodiment, those matches having a Match_Difference_Factor less than a given amount (termed the Threshold_Amount) are kept so long as: no better template match value exists within the range of data covered by that template corresponding to that match difference factor, and the template does not overlap any other matched templates. The Threshold_Amount should be small enough that a minimum (or no) false "hits" are made (indicating a feature where none exists), and large enough that a limited number of templates will match the features in the file. In a preferred embodiment of the present invention, a default threshold value is provided, however, the operator can change the threshold value through a suitable user interface.

Other methods of template matching may be used, depending on the type of data available, the accuracy desired, and the amount of time and computational space that is available for performing this step. One alternative method is to use a vector difference or magnitude comparison rather than phase signal matching, or matching the amplitude rather than the phase.

Still referring to FIG. 10, once the template matching is completed, a report is made available for use by the operator at a block 152. There are numerous pieces of helpful data that may be reported, including the shortest, longest, and average pipe length dimensions. An Overall_Average_Match_Difference_Factor is provided, indicating how well a particular template matched with the entire file. A specific Average Match_Difference_Factor for each match location is also provided that reflects how well a template matched at the places where a successful match was determined. Further helpful information includes a listing of the number of matches found, the minimum and maximum distance between two matches, the distance from the start of file to the first match, the distance from the last match to the end of file, the average match value at matches, and the average match value throughout the file.

The report further indicates whether certain elements did not occur and the average distance between matches. This data allows the operator additional insight into where additional templates should be selected, whether some poorly chosen ones should be removed, or whether the Threshold_Amount changed. In general, the Threshold_Amount should be less than the Overall_Average_Match_Difference_Factor, otherwise a high number of false hits will occur. If the data does not produce some good matches, the operator should reverify that the data is usable.

Once the none-analyzable elements have been located in the prepared data, it is preferred that a visual plot (e.g., a strip chart plot) is made available to the operator showing the bounds of all such features. This makes it relatively easy for the operator to verify what elements have been located, whether any items were missing, and whether a false indication has occurred. Should features have been missed and/or false hits have occurred, the system provides the operator with the opportunity to remove match locations that are incorrect or to force a match of a selected template at a given location.

Referring back to FIG. 7, the general analysis task 52 includes separating the data at block 66 into smaller units, such as pipe lengths. This makes it easier for the program to take advantage of repeated steps and permits the operator to force the analysis of only a particular location, if so desired. At block 68, within each pipe length, a nominal value is defined reflecting the hypothetical signal that would be received for a particular pipe length with no defects, i.e., the signal for a "perfect" pipe length. Using the nominal signal, a Phase Profile is calculated for each data point in the pipe length. The Phase Profile value is the theoretical phase value the specific data point would have if only circumferential metal loss had occurred in the pipe (i.e., if there had been no pitting component in the RFT signal.)

The phase signal is used to locate potential defect locations that are significant enough to be analyzed at block 70. A total EQPS signal (defined and described in detail below) is also determined at block 70 for each of the potential defects. By obtaining various calibration settings at block 72, it is then possible to use the calibration values and the total EQPS signal to determine the defect type, percentage remaining wall thickness, and the actual wall thickness at block 74.

Parse Data Into Pipe Lengths

Referring to block 66 of FIG. 7, the prepared data is initially separated into pipe lengths using the information obtained in block 64, particularly the identification of bell-and-spigot locations from a template matching algorithm. The parsing of prepared data may be accomplished in a number of different ways. In one embodiment, markers are placed within the prepared data set pointing to the beginning and end of each non-analyzable element. The prepared data between a particular pipe length ending marker and the next pipe length beginning marker thereby defines a single analyzable subgroup of data points. Likewise, markers indicative of other located elements may be used so that these data points are not treated as defects. In this manner, the portions which should not be analyzed are effectively ignored.

Determine Nominal Valnies

Figure 11:
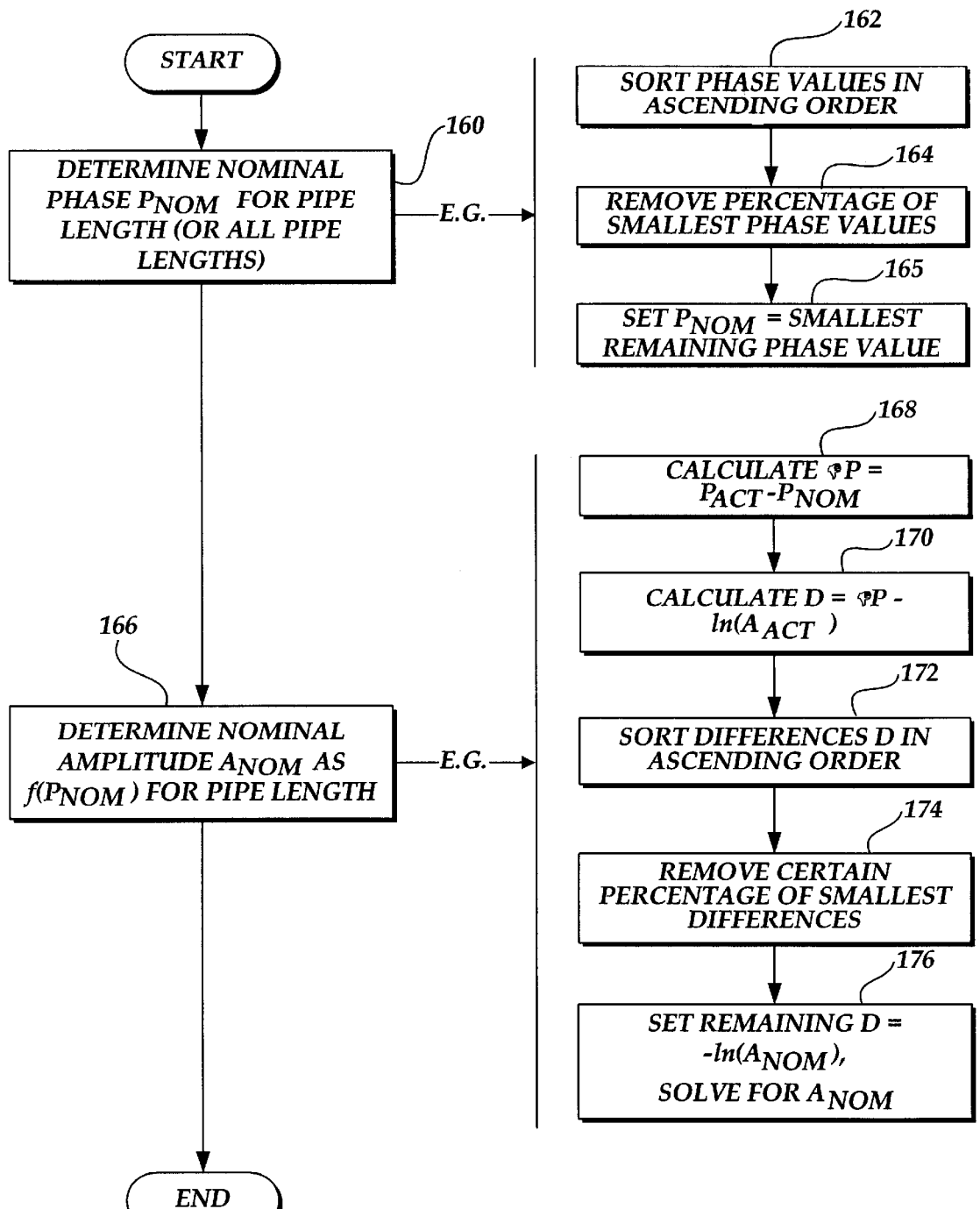
FIG. 11 is a logic diagram of one embodiment of a method used to determine nominal data values.

The subsequent pipeline analysis relies on relative changes in phase and amplitude values to indicate a change in the pipeline wall thickness. Therefore, it is necessary to establish a nominal phase and amplitude signal representative of a "perfect" pipe so that any relative change in these values can be determined. The accuracy of the analysis is greatly dependent on the appropriate selection of these nominal values. Referring to FIG. 11, nominal values include a nominal phase $P_{NON}$ and a nominal amplitude $A_{NOM}$ determined at blocks 160 and 166, respectively.

One method of determining nominal phase $P_{NOM}$ is to create a sorted list of all pipe length phase values and select a percentage of pipe deemed to be thicker than nominal. Referring to FIG. 11, the analyzable phase values of a particular pipe length are sorted into ascending order at a block 162. A certain percentage of phase values are removed from the bottom of tie list at a block 164. The selection of the percentage will depend on the type of pipe and its method of formation. The smallest phase value remaining after the removal is selected at a block 165 as the nominal phase $P_{NOM}$. For example, if the lowest 10% of the phase values are eliminated, the value of $P_{NOM}$ is then set to the smallest remaining phase value. It is also possible to determine $P_{NOM}$ in this manner for an individual pipe length rather than a set of pipe lengths. One way to determine $A_{NOM}$ is to scale all actual amplitudes by a factor selected to ensure that a significant portion of the amplitude data becomes located on, near, or inside the circumferential loss Reference Curve as viewed on tile voltage plane.

A nominal amplitude $A_{NOM}$ may be statistically determined as well. As background information, for circumferential loss, RFT equations imply that a change in phase is equal to a change in the natural log amplitude, $\Delta P = \Delta(\ln A)$. RFT equations also imply that the change in phase $\Delta P$ will actually be greater than the change in A (lnA) for a pitting defect. If $\Delta P < \Delta(\ln A)$, that is, the data point is positioned outside the Reference Curve, one would expect a change in material properties, such as permeability and/or conductivity, to have occurred based on the assumption that $\Delta P < \Delta \ln(A)$. Which is characteristic of such situations.

Using the above phase and amplitude relationships and referring to a block 168 in FIG. 11, a change in phase $\Delta P$ is calculated at each data point as the difference between the data point's actual phase $P_{ACT}$ and the nominal phase $P_{NOM}$. At a block 170 the difference D is calculated by subtracting $\Delta(\ln A)$ from $\Delta P$. After the differences D for all data points have been determined, they are sorted in ascending order at a block 172. A certain percentage of the smallest differences are eliminated at a block 174 and the remaining difference D is equated to $-\Delta(\ln A_{NOM})$, from which $A_{NOM}$ for the pipe length may be calculated at a block 176.

In the computer embodiment described below, the operator is provided with various ways by which nominal values can be defined and redefined. For example, the operator can force a particular nominal value. The operator can select a value from a specific location in the data set (defined by index, meter, or footage location). Or, the operator can request the program itself to suggest a nominal value. After the selection of nominal values, the operator is provided with the opportunity to visually review the data and the opportunity to make adjustments as desired.

Determine Phase Profile

Before locating and analyzing the severity of each defect, the present invention method first uses the voltage plane polar plot to attempt to qualify the type of defect represented. Theoretically, any data point that is not equal to the nominal value is indicative of a defect. However analyzing a data point using the RFT analysis technique (see FIG. 15B, described below), which uses the change in phase and amplitude from nominal tends to give incorrect results if the defect is composed of both circumferential and one-sided pitting loss. This is uncommon in small bore tubes since manufacturing tolerances are high, but in waterlines it is common to have fairly large circumferential variations. Therefore, a novel two-step approach is taken to correctly analyze the defect. The two-step analysis is a method of analyzing defects having of both circumferential and one-sided non-circumferential metal losses. This method is particularly useful for analyzing water main RFT data. In order to do a two-step analysis, the defect signal must be broken into the component caused by circumferential wall variation, and the component caused by one-sided non-circumferential pitting. The phase prefile is the theoretical phase of the circumferential part of the signal.

In order to perform this two-part analysis, there must be some type of indicator to permit the analysis to distinguish between the two types of metal loss (that is, between pitting and circumferential metal loss components in the defect trace). In addition, because of noise and other non-defect data anomalies, it is useful to generalize the data, within reasonable bounds.

The Phase Profile is the phase value of the data point representing only circumferential metal loss at that particular location. The value assigned to a Phase Profile is based on a number of assumptions. One assumption is that almost all metal loss defects include phase changes, and conversely, that most phase change data is indicative of a metal loss defect. It is also assumed that where there is actual metal loss, the arcuate circumferential extent of a defect will be either circumferential or less-than circumferential (e.g., one-sided pitting). Since automated or manual analysis may be done for at any point, all data points in a pipe length have a Phase Profile determined.

In RFT technology, a simple exponential relationship exists between amplitude and phase for circumferential defects. A circumferential local reduction in wall thickness of $\phi$ skin depths will cause the phase of the field at an adjacent point inside the tube bore to increase by $\phi$ radians and the amplitude of the field to increase by a factor of $e\phi$ (1 radians $\approx 57.3°$ and $e \approx 2.72$). Upon passing circumferential wall metal loss, an RFT detector coil output signal will therefore show an amplitude change which is directly proportional to the phase shift in radians.

This results in a circumferential data trace following the Reference Curve plotting of $e^{\Phi} \angle \Phi°$. If a defect is less-than completely circumferential, the defect will have an amplitude change that is proportionally less than the exponential of its corresponding phase shift in radians. For less-than-circumferential metal losses, the data traces thus appear to leave and travel inside of the Reference Curve. See FIG. 12.

Figure 13A:
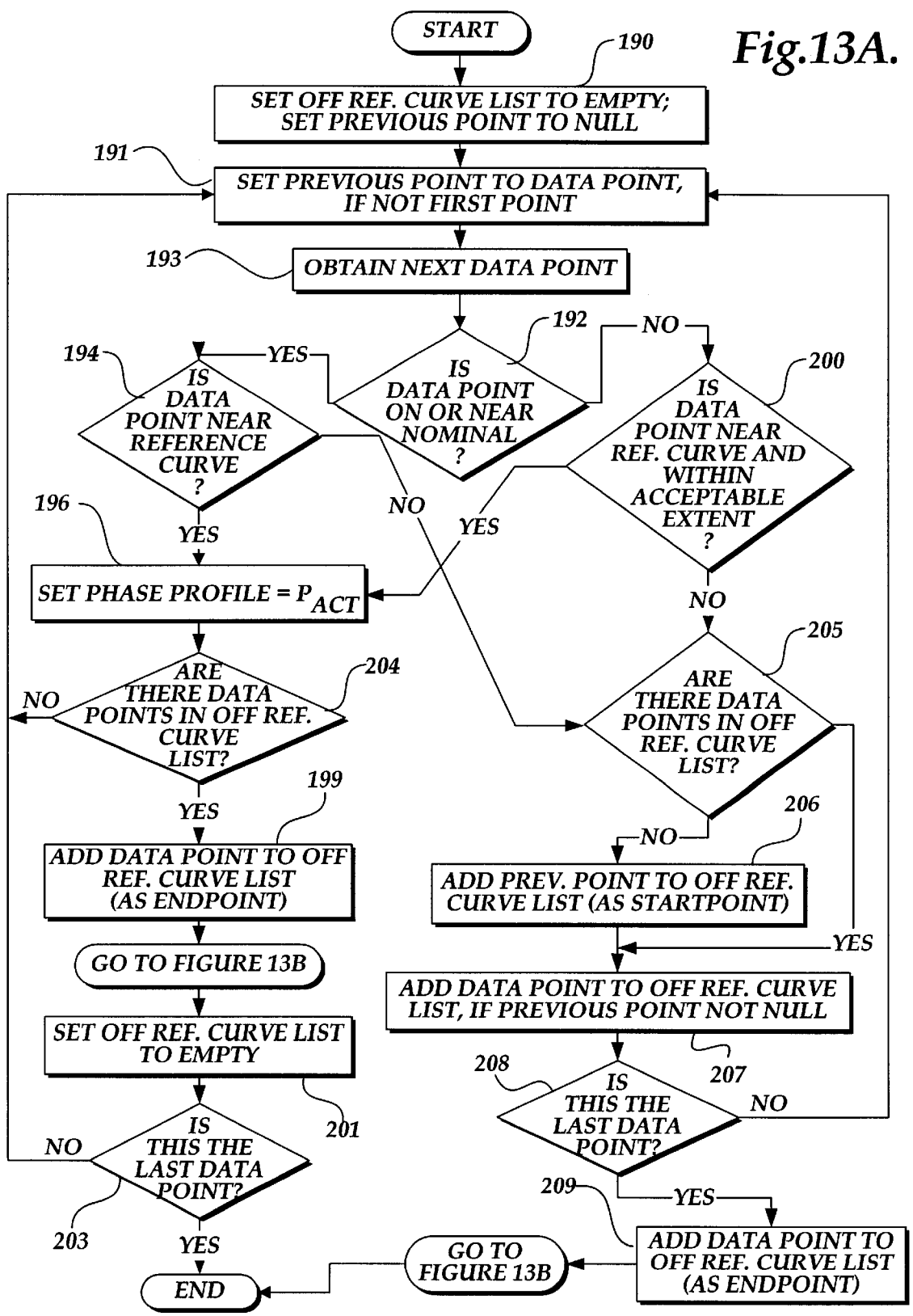
FIGS. 13A and 13B are logic diagrams of one embodiment of a method to determine a Phase Profile for the subject data points.
Figure 13B:
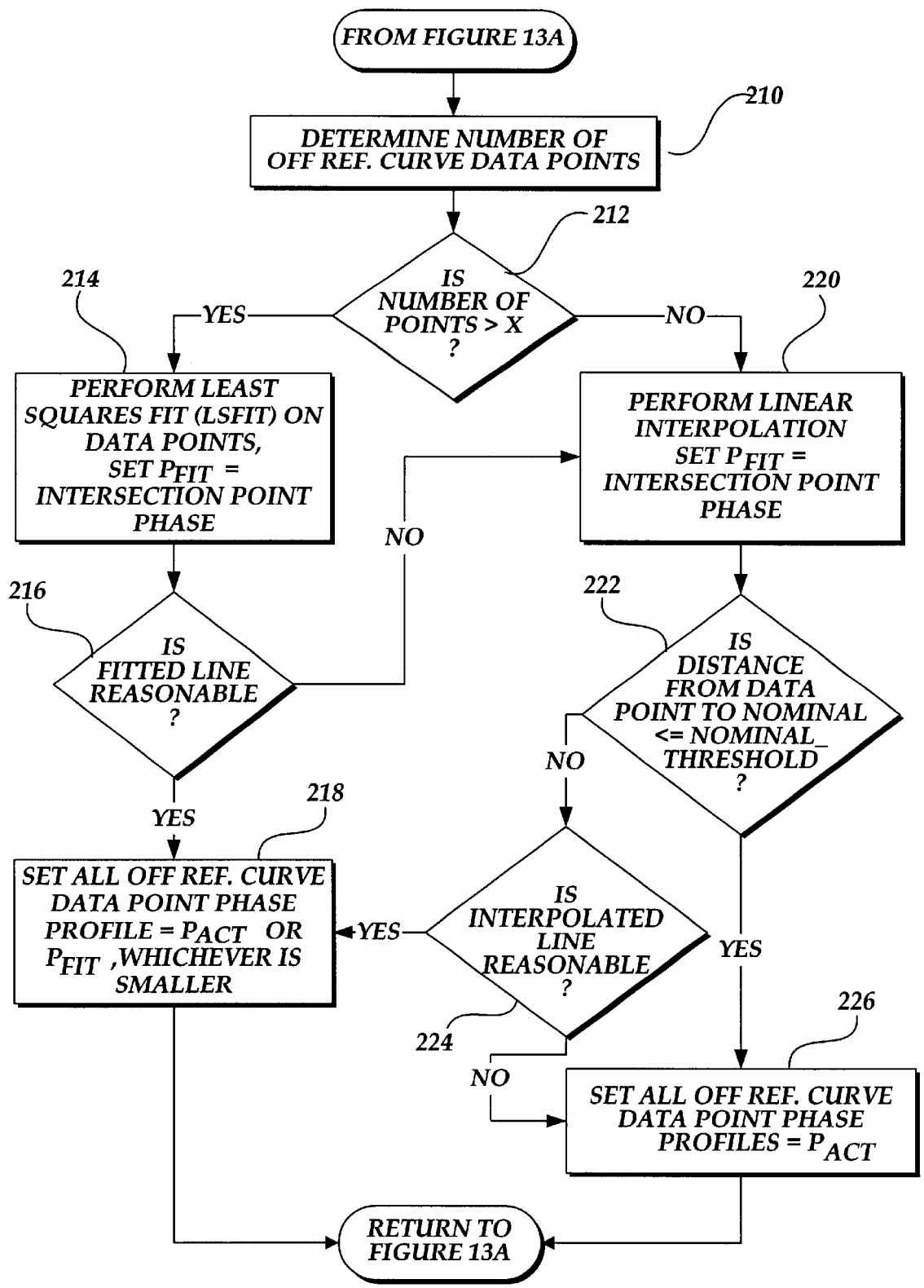

FIGS. 13A and 13B illustrate one embodiment of logic for accomplishing the determination of Phase Profile for each data point. In general, if a data point is located near the nominal signal value, it is treated as if it were actually on the nominal signal. If a data point is positioned outside the Reference Curve, it is assumed to represent a material variation in the pipe for which an accurate wall-thinning evaluation would be difficult to make. Data points outside the Reference Curve are thus treated as if they were on the Reference Curve. If a data point is on or slightly inside of the Reference Curve, the data point is also assumed to have no pitting component requiring analysis and is thus treated as if it were solely a circumferential metal loss.

In more detail and referring to FIG. 13A, the logic sequences through each data point, assigning it an appropriate Phase Profile. Prior to processing of the data points, initialization occurs in a block 190. The initialization includes setting an Off Reference Curve list to empty and setting a previous point to null. If this is not the first data point, the previous point is set equal to the data point in a block 191. The next data point is then obtained in a block 193. Then, at a decision block 192 a determination is made as to whether the data point is on or near the nominal signal. If so, the data point Phase Profile is set equal to the actual phase value $P_{ACT}$. (In later analysis, if the actual amplitude $A_{ACT}$ for that data point is greater than the nominal amplitude $A_{NOM}$, the nominal amplitude $A_{NOM}$ is used, thus effectively treating the data point is if it were at nominal.) In one embodiment, a NOMINAL_THRESHOLD margin is used to determine whether the data point is close enough to the nominal signal to be considered nominal. The value of such a NOMINAL_THRESHOLD percentage will vary depending on the application.

Even if the data point is near nominal, it may yet represent a defect signal. Determination is made at a decision block 194 as to whether the data point is near the Reference Curve. If so, the data point Phase Profile is set equal to the actual phase value $P_{ACT}$ in a block 196. At a decision block 204 a test is made to determine whether there are any points in the Off Reference Curve list. If there are not any points in the Off Reference Curve list, the logic returns to block 193, and the logic is repeated for the next data point. If there are data points in the Off Reference Curve list, the logic proceeds to a block 199 where the data point is added to the Off Reference Curve list as the endpoint. The logic then proceeds to FIG. 13B (described below) where an analysis of the Off Reference Curve points is conducted. After conducting the Off Reference Curve point analysis of FIG. 13B, the logic proceeds to a block 201 where the Off Reference Curve list is set to empty. Next, at a decision block 203, inquiry is made as to whether the data point is the last data point. If this is the last data point, the logic ends. If there are more data points, the logic returns to block 190 and continues for the remaining data points.

If a data point is not on or near the nominal signal at decision block 192, inquiry is made at a decision block 200 as to whether the data point is acceptably placed relative to the Reference Curve. One useful test is to determine whether the shortest distance from the data point to the Reference Curve and nominal signal is within a REFERENCE_CURVE_THRESHOLD margin. See FIG. 12. In one embodiment, the REFERENCE_CURVE_THRESHOLD margin is in the range of about 0.03 to about 0.05 (relative to a normalized plot on the voltage plane where the nominal phase and amplitude is located at coordinate (1,0).) These values will vary depending on the application.

In determining whether the data point is within an acceptable extent, the data point is compared to a pre-defined EXTENT_THRESHOLD percentage. For example, using an EXTENT_THRESHOLD of 75%, the ratio of a line 1 to line $L_0$ would be equal to or greater than 0.75, where line 1 is a straight line drawn from the nominal signal to the data point, and line $L_0$ is a straight line drawn from the nominal signal through the data point and to the Reference Curve. If the data point does not have an extent within such a percentage, it is assumed that the data point should be analyzed as a defect and should not have a Phase Profile equal to the corresponding Reference Curve phase value.

Referring to FIG. 13A, if the data point is within an acceptable extent of the Reference Curve, inquiry is made as to whether there are points in the Off Reference Curve list in a decision block 205. If there are not any points in the Off Reference Curve list, the logic proceeds to a block 206 where the previous point is added to the Off Reference Curve list if the previous point is not null. Regardless of whether there are points in the Off Reference Curve list, as determined in decision block 205, the logic proceeds to a block 207 where the data point is added to the Off Reference Curve list. Next, inquiry is made as to whether this is the last data point. If this is the last data point, the data point is added to the Off Reference Curve list as the endpoint, and the Off Reference Curve point analysis of FIG. 13B is conducted. If it is determined in decision block 208 that this is not the last data point, the logic returns to block 190.

Referring to FIG. 13B, a determination of how many data points are consecutively off the Reference Curve is made at a block 210. If it is determined in decision block 212 that the number is greater than a given size X, the logic performs a least squares fit (LSFit) algorithm to the set of data points at block 214. For example, the least square fit of the known program "$G^2CHI$" may be used. Other types of line fitting logic are available. A temporary variable $P_{FIT}$ is set equal to the intersection point between the Reference Curve and the line $L_{LSFIT}$ at block 214 as well. If the resulting line $L_{LSfFIT}$ (see FIG. 12) is oriented at a reasonable angle relative to the Reference Curve at a decision block 216, then at a block 218 all off Reference Curve data point Phase Profiles are set equal to the phase value $P_{FIT}$ that corresponds to the intersection phase value or set equal to their actual phase $P_{ACT}$, whichever is smaller.

Various types of reasonableness checks may be performed at block 216 to determine whether the line-fitting was well-behaved, and thus successful. The important issue is whether the line produced a "good and reasonable fit". For example, are the beginning and end points A and B relatively close together? Is the angle from point A to the innermost tip back to point B a relatively small angle? Is the intersection point near points A and to? Is the angle between a line extending from, the origin B, the intersection point, and the fitted line within a reasonable range?

Figure 12:
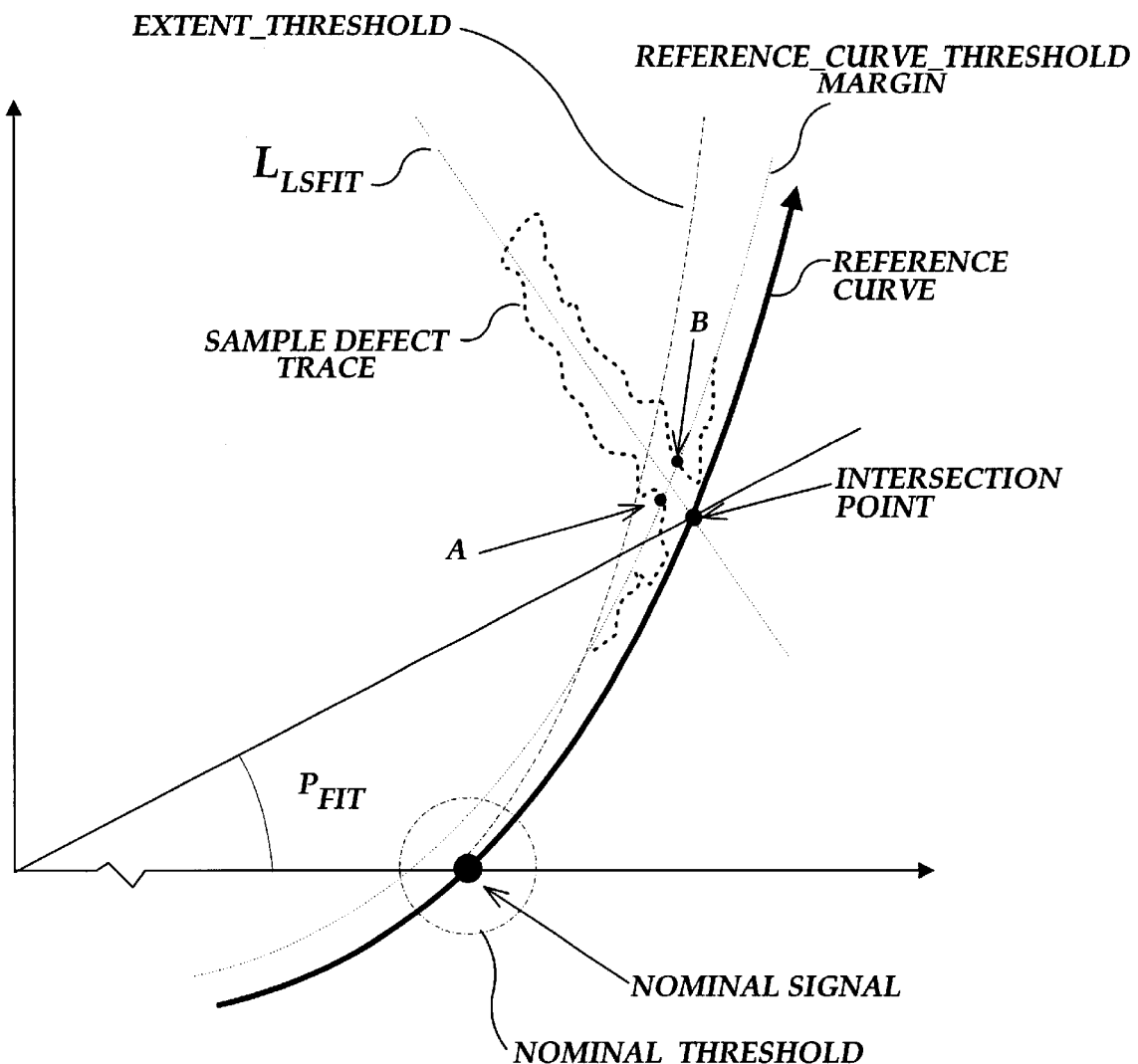
FIG. 12 is an illustration of a voltage plane depicting aspects of the method shown in FIG. 11.

Still referring to FIG. 13B, if the number of off Reference Curve data points is less than or equal to the given size X, tile logic performs a linear interpolation at a block 220 between the phase values at points A and B (see FIG. 12.) The logic also performs this linear interpolation if the angular orientation of $L_{LSFIT}$ is unreasonable as determined at decision block 216. After interpolation, the temporary variable $P_{FIT}$ is set equal to the intersection point between the interpolated line and tile Reference Curve.

A separate check is performed at a decision block 222 to determine the distance from a particular data point to the nominal signal is less than or equal to the NOMINAL_THRESHOLD margin. If so, the Phase Profile of that data point is set equal to the actual phase value $P_{ACT}$ at a block 226. If not, inquiry is made as to whether the angular orientation of the interpolated line is reasonable at a decision block 224. If so, at block 218 the data points are set equal to the smaller of the actual phase values $P_{ACT}$ or the temporary variable $P_{FIT}$, whichever is smaller. Other methods for determining Phase Profile may be used.

Locate Potential Defects

Practicably, it is very difficult to analyze each data point as a defect. Therefore, the present invention method identifies likely defect locations and then analyzes each location—first to determine the severity of circumferential metal loss (i.e., general corrosion) and second to determine the severity of less-than-circumferential metal loss (i.e., pitting.). This helps to identify those data points that have a high probability of actually being a defect.

Figure 14:
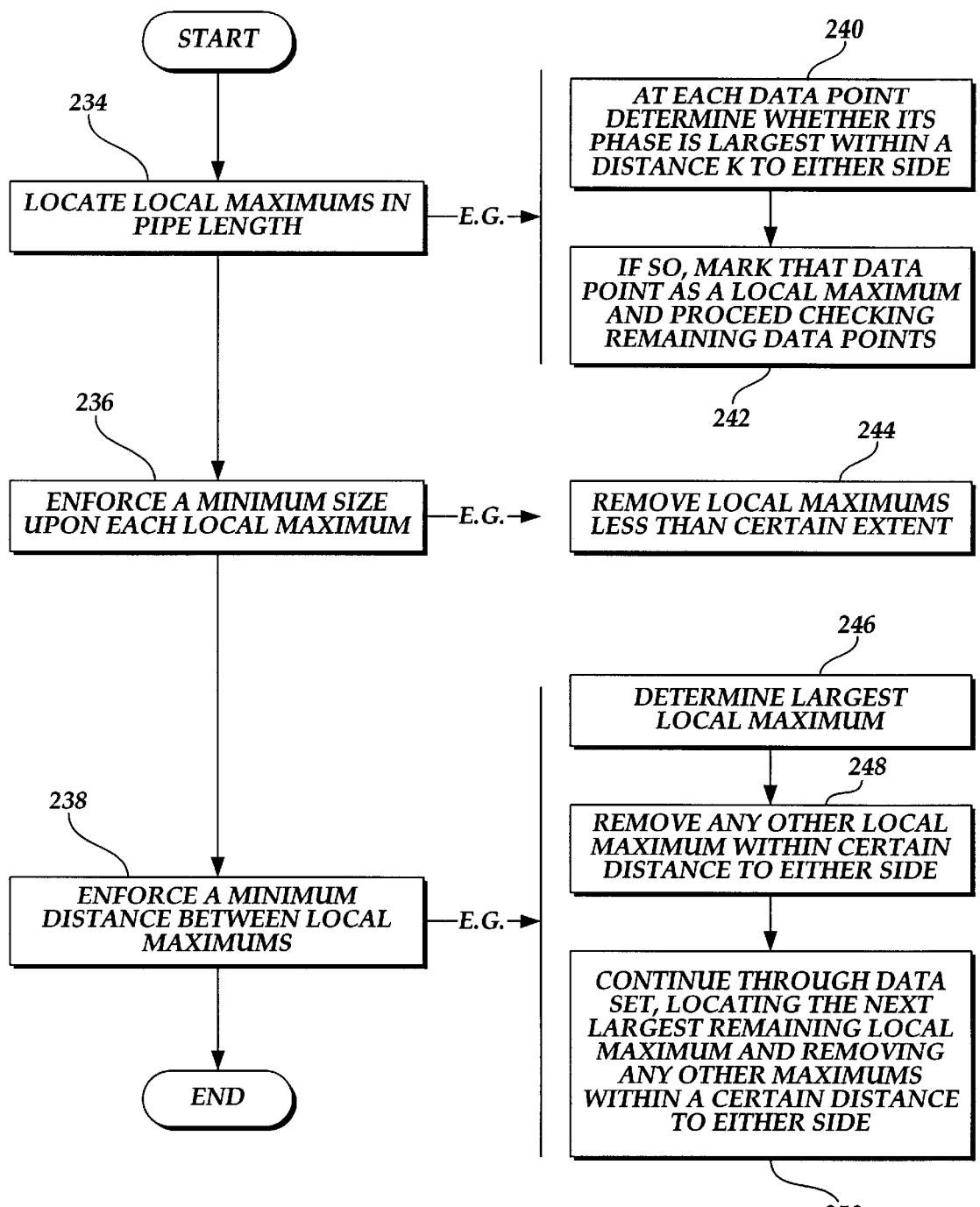
FIG. 14 is a logic diagram of one embodiment of a method to locate defects using Phase Profile values.

Referring back to FIG. 7, the logic locates potential defects at block 70. FIG. 14 illustrates one embodiment of a method that may be used to accomplish this task. At a block 234, local maximums are found within the pipe length, for example, by comparing the phase of each data point with the phase of the adjoining data points within a pipe distance K to either side as indicated at a block 240. The distance K in one embodiment was in the range of about 2 cm to about 10 cm, with an amount of 5 cm being determined optimal. These values will depend on the size of pipe being analyzed. If the data point phase is the maximum phase amount in the range –K to +K, then at a block 242 the data point is flagged or marked in some manner as a local maximum and the logic proceeds checking the remaining data points.

To reduce the number of false defect identifications, additional factors may be considered and weighed in selecting candidate defects. Using additional factors greatly reduces the number of incorrect defect identifications, thus increasing overall accuracy and speed of the system. Two such checks are illustrated in FIG. 14 at blocks 236 and 238.

At block 236, a minimum size limit is enforced upon each local maximum, for example, by removing marking of local maximums less than a certain extent as shown in block 244. This is particularly useful in eliminating small signal noise variations that appear as very severe defects, but in fact are not. In one embodiment, local maximums with an extent of less than about 0.04 are unmarked.

At block 238 a minimum pipe distance is enforced between local maximums. For example, if the pipe distance between local maximums is less than or equal to a certain pipe distance, then only one defect is kept and the others are unmarked. At a block 246, the logic accomplishes this by determining the largest local maximum in the pipe length. Any other local maximum within a certain pipe distance to either side is unmarked at a block 248. At block 250, the logic continues through the pipe length data set, locating the next largest remaining local maximum and unmarking any other maximums within a certain pipe distance to either side.

Other checks to ensure the reasonableness of the identification of a defect may be performed as determined necessary or desirable.

Calculate Total EQPS

Figure 15A:
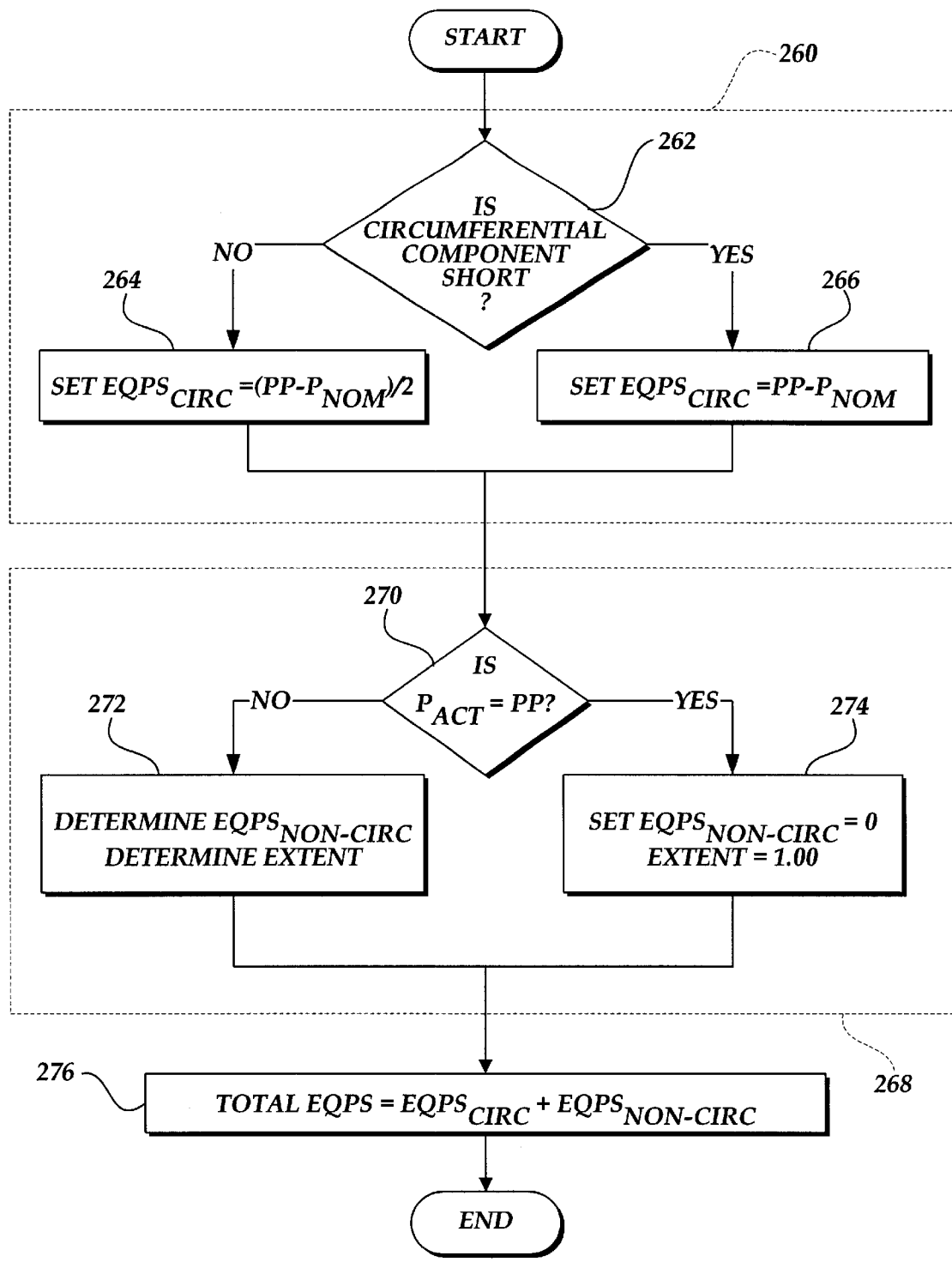
FIG. 15A is a logic diagram of one embodiment of a method to calculate a Total EQPS value for a given defect.
Figure 15B:
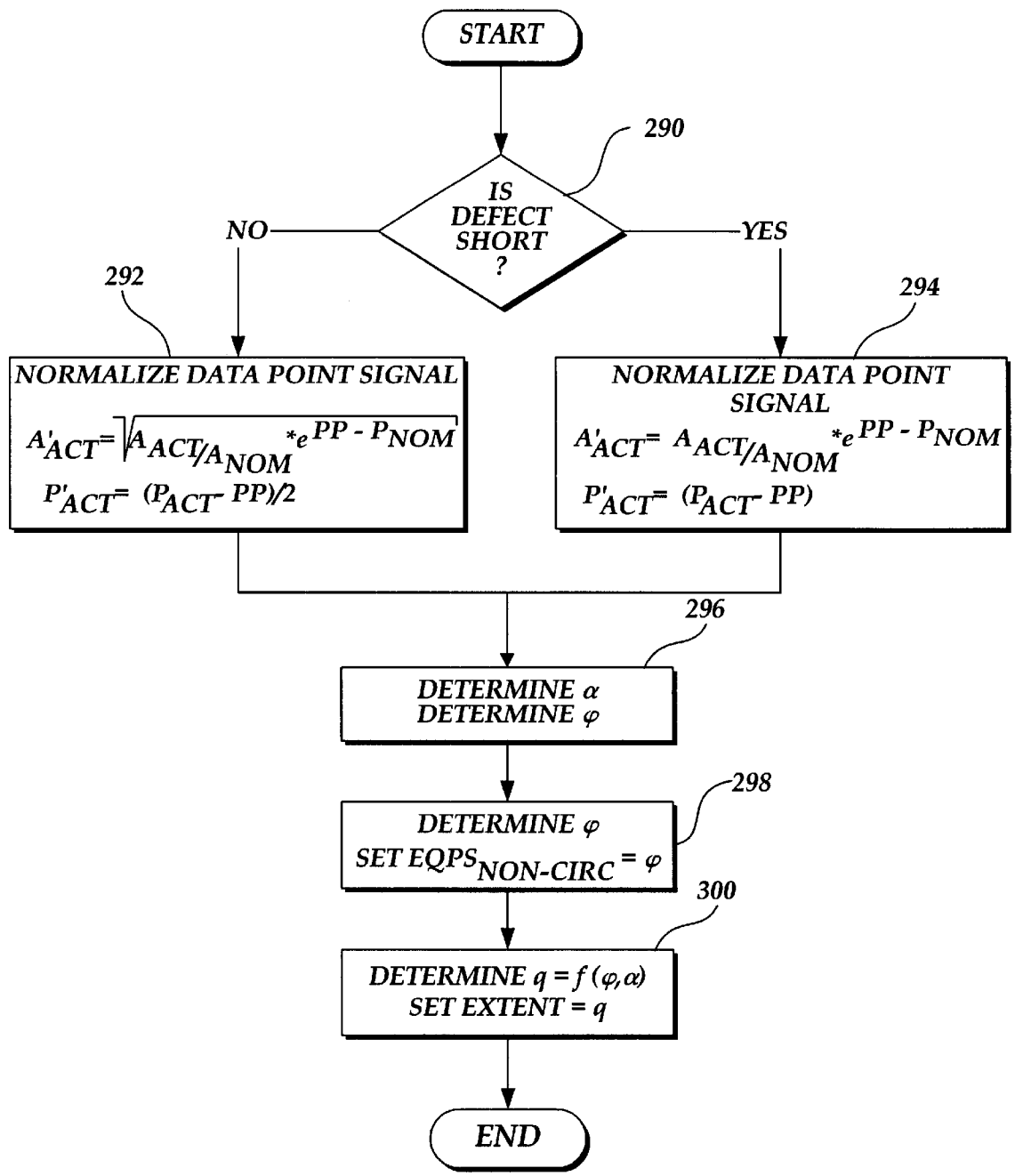
FIG. 15B is a logic diagram of one embodiment of a method to determine an $EQPS_{NON-CIRC}$ value for a given defect.

Sufficient information regarding whether a defect is a circumferential or non-circumferential defect is available from the data point Phase Profile values. To determine the percentage wall thickness remaining (and to relate that information to actual defect depth), it is necessary to calculate a Total EQPS at each defect location. This step is accomplished in FIG. 7 at block 70. Referring to FIGS. 15A and 15B, the logic calculates Total EQPS for a select defect at step 276 as the sum of both a circumferential EQPS ($EQPS_{CIRC}$) and a non-circumferential or pitting ($EQPS_{NON-CIRC}$). The $EQPS_{NON-CIRC}$ is an estimate of the phase change a non-circumferential wall loss would have caused if it had been fully circumferential.

Both the $EQPS_{CIRC}$ and $EQPS_{NON-CIRC}$ are adjusted to account for the defect being a long or short defect. Because every defect appears twice in the recorded data—once as the exciter passes by the defect and once more as the sensor moves by the defect—if a defect is longer than the sense-exciter coil separation, the two occurrences in the recorded data will overlap by some amount. These are termed long defects. If the data does not overlap, the defect is a short defect. Two defects can also result in a single larger peak when one defect is under the exciter coil while the other is under the sensor coil. Care should be taken to ensure that only a single signal value is analyzed and not a combination from a long defect. Because circumferential defects tend to be long defects, it is useful to assume this in determining the Total EQPS, but to continue to check the data to determine if the defect is short as appropriate. Similarly, it is useful to assume that non-circumferential or pitting defects are short defects, and verify as appropriate.

Figure 44:
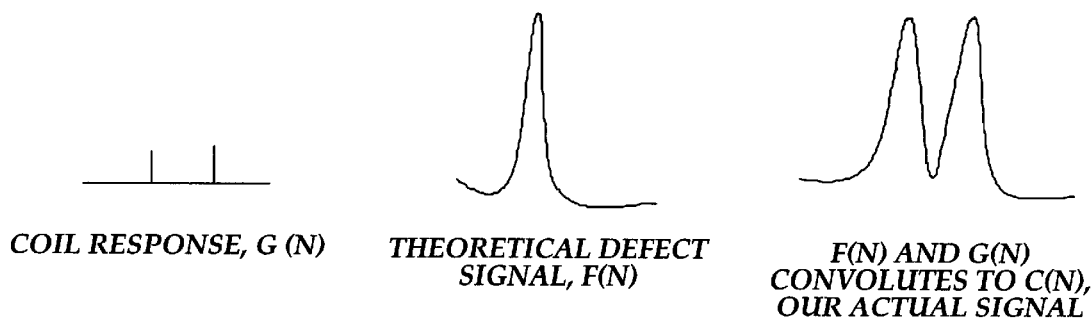
Figure 45:
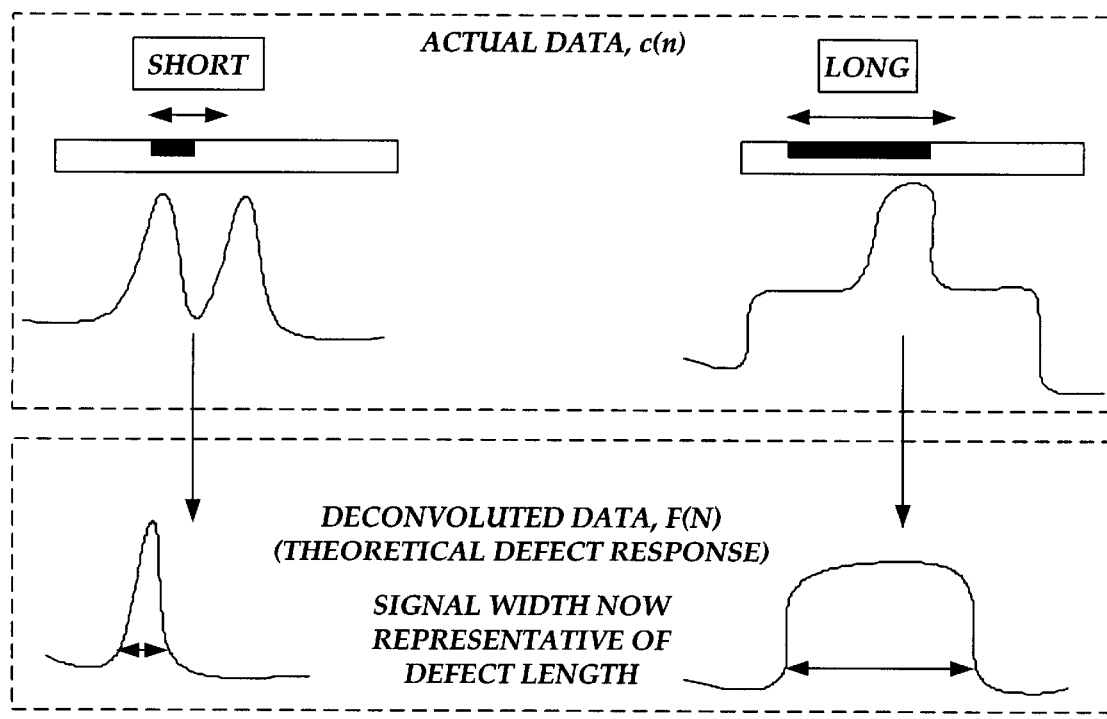

One possible way to improve this assumption is to attempt to deconvolute the data. Referring to FIG. 44 and 45 convolution can be visually described as sliding two functions past each other while multiplying the overlapping data points and determining the area under the resultant curve. The reverse operation is deconvolution, i.e., c(n) deconvoluted with coil response g(n) equal theoretical defect signal f(n). For discrete values such as our data samples, if c(n) equals convolution of f(n) with g(n) then $$c(n) = \sum_{p=-\infty}^{p+\omega} f(n) * g(n-p)$$

If we consider a theoretical defect signature data trace f(n), and model our sensor-exciter coil response g(n) as two impulse functions separated by the sensor-exciter coil separation, the convolution of the two, c(n) would look like the data of the present invention.

Hence, if actual data is deconvoluted by the coil response, theoretical defect response is obtained, and by its width it can be determined whether the defect is long or short.

Deconvoluting data by a model of the coil response is not a trivial task, particularly since the summation in the convolution/deconvolution makes the process extremely sensitive to noise which becomes cumulative and tends to make the solution unstable (i.e., result are noisy and are not similar to the theoretical response). In an embodiment of the present invention, a theoretical defect response, f(n) is achieved by repeatedly guessing at a solution for f(n), and then shifting the tool length T and adding it to itself creating h(n)=f(n)+f(n+T). If h(n) is similar to our actual data, c(n), then f(n) is a reasonable theoretical defect response of c(n) and a good estimate of the signal deconvolution. If h(n) is not similar to c(n), the f(n) was a poor guess, and a small change should be made as a new guess, until a good guess is made. In this manner a pseudo deconvolution of the signal data can be achieved.

Due to the cumulative additive effect of noise, and the difficulty in correctly guessing at a pseudo deconvolution f(n) for kilometers of data, the process must be simplified. One solution is to solve for f(n) for individual pipe lengths. The process can further be simplified by only guessing at the first few data points in f(n), until a tool length, T, is covered. Now, if f(n) is defined for n=0 to T−1, and h(0)=f(0)=f(T) and h(n) should be equal to c(n), therefore f(T)=c(0)−f(0) which defines f(T). Similarly, f(T+1)=c(1)−f(1). Applying this equation, f(m+t)=f(m)−c(m) for m=0 to end of joint creates a f(n) defined for the entire joint based on a guess of f(n) for n=0 to T. Now a determination is made whether f(n) is a good guess at the theoretical defect response and deconvoluted signal. One approach is to determine the variance or noise in f(n), and then change the initial guess a f(n) for n=0 to T−1 until the noise is minimized.

Referring to FIG. 15A, $EQPS_{CIRC}$ is determined at a block 260, and $EQPS_{NON-CIRC}$ is determined at a block 268. The two amounts are combined at block 276. Referring to a decision block 262, if the circumferential component of the defect is short then $EQPS_{CIRC}$ is set equal to the difference between the data point's Phase Profile and the nominal phase $P_{NOM}$ at a block 266. If the circumferential component is not short, $EQPS_{CIRC}$ is set equal to half the same difference at a block 264. (For those defect maximum data points representing only a pitting component, i.e., without a circumferential component, the difference between Phase Profile and $P_{NOM}$ will be zero resulting in $EQPS_{CIRC}$ being set equal to zero as well.

The logic moves from blocks 264 and 266 to block 268 where $EQPS_{NON-CIRC}$ is calculated. Referring to a decision block 270, if the data point phase value $P_{ACT}$ is equal to the data point Phase Profile value (i.e., no pitting), then $EQPS_{NON-CIRC}$ is set to zero and the extent of the defect is set equal to 1.00 or 100%. If there is no equality at block 270, then $EQPS_{NON-CIRC}$ and extent are determined at a block 272. The logic continues from blocks 272 and 274 to the calculation of Total EQPS at block 276.

FIG. 15B illustrates one embodiment of a method of calculating $EQPS_{NON-CIRC}$ and extent (block 272 in FIG. 15A). If the value of the defect's $EQPS_{CIRC}$ is non-zero (meaning there is circumferential metal loss combined with pitting), the calculation of the pitting EQPS is performed by essentially ignoring the circumferential portion of the defect. This may be thought of conceptually as the equivalent of rotating the voltage plane orientation such that the Phase Profile value used for the off Reference Curve data point becomes a new nominal signal (i.e., becomes located at the intersection of the x-axis and the Reference Curve.) Therefore, the value of the defect's Phase Profile is used to define the new nominal phase. In FIG. 15B this is referred to as PP, now the nominal point of (1,0) The normalized data point is referenced as point $P'_{ACT}$ and $A'_{ACT}$.

In addition to ignoring the circumferential part of the signal, the signal must also be adjusted to account for whether the defect causing it is long or short. The change in phase from the Phase Profile, and the change in ln(Amplitude) from the amplitude at the Phase Profile must be halved. One way to accomplish this signal rotation and scaling is to normalize the data for pittinig-only analysis is as described in FIG. 15B.

Computationally, if the defect is a short defect at a decision block 290, then the various data points are normalized at a block 294 so that the phase profile is at the rectangular coordinates of (1,0). The data point amplitude is normalized by dividing by $A_{NOM}$. The data point phase is normalized by subtracting $P_{NOM}$. If the defect is not a short defect at decision block 290, then corresponding normalized data point amplitude and phase values are determined at a block 292. The logic proceeds from blocks 292 and 294 to a block 296. At block 296 the conventional RFT angle α is determined (equal to the new nominal phase), and the conventional RFT orientation angle θ is determined by converting the normalized data point signal into rectangular coordinates and measuring the angle θ directly. The orientation angle θ is defined in RFT terminology to be the angular orientation of the defect trace.

At a block 298, the conventional RFT Phase Lag φ angle is determined using bisection to solve for φ from a conventional mathematical RFT relationship of θ=f(φ) such as:

$$\theta = \tan^{-1}(\sin\varphi / (\cos\varphi - e^{-\varphi})) = f(\varphi) \quad (3)$$

It will be appreciated that several geometric solutions are possible. The $EQPS_{NON\text{-}CIRC}$ is set equal to the Phase Lag φ angle in block 298 as well. At block 300, the conventional RFT defect trace fractional circumferential extent q is calculated as a function of φ and α. One such mathematical relationship is:

$$q = (e^{\varphi}(\sin\varphi \cdot \cot\alpha - \cos\varphi) + 1)^{-1} \quad (4)$$

The extent is set equal to q in block 300 as well. For additional information regarding RFT theory and mathematical equations relating these variables, see *Remote-Field Eddy Current Signal Analysis in Small-Bore Ferromagnetic Tubes*, by David D. Mackintosh, David L. Atherton, and Sean P. Sullivan, Materials Evaluation, April 1993.

Calibrate Analysis

Referring back to FIG. 7, the analysis continues to block 72 where one or more calibration factors are determined. Although there is a direct relationship between phase shift and percentage metal loss, calibration is needed 1) to relate the calculated nominal signal to an actual nominal pipe thickness and 2) to relate phase change to an actual pipe metal loss thickness (i.e., to understand the signal change caused by a known defect). By measuring the phase change caused by a known circumferential defect in a calibration pipe of the same material and dimensions as the investigated pipe, the depth of unknown defect areas can be determined in the investigated pipe. The accuracy of the remaining analysis step at block 80 is thus dependent on the appropriate selection of calibration values. In preferred embodiment, a combination of the methods below are used, compared, and combined in order to improve the calibration estimates overall.

If possible, calibration information is determined from a sample portion of new pipe with a known manufactured circumferential defect, where the calibration pipe is of similar dimensions and material properties as the inspected pipe. If such a pipe is not available (which is often the case for waterlines), calibration can be made from an exhumed portion of the actual pipeline that includes a defect. In either case, an RFT measurement device is pulled through the sample pipe. The pipe nominal signal values $P_{PIPE\text{-}NOM}$, $A_{PIPE\text{-}NOM}$ are noted, as well as the change in phase and amplitude for a defect of known size.

Similarly, as a second alternative, a portion of unexhumed (though partially exposed) actual pipeline may be used for calibration. A first measurement is taken with the RFT device fully within the pipe. Instead of calculating the phase shift obtained from a known defect, however, a data measurement is taken with the measurement device halfway outside the pipe. The signal change between the two readings is approximately equivalent to a 100% circumferential short defect. This signal change can then be used as a calibration value together with the wall thickness measured at the test location. In cases where a length of PVC pipe section from a previous repair is positioned at a location in the pipe, the above measurements may be made without requiring a dig, except the measurement regarding actual wall thickness measure is not available. Another possibility is to take a reading with the tool completely in free air and use the signal as a long 100% circumferential defect for calibration.

If calibration cannot be made using the above methods, it is possible to get adequate calibration information from the RFT measurement data itself, assuming that the material properties (i.e., conductivity and permeability) of the inspected pipe are in fact fairly homogeneous throughout the pipe, and by making assumptions about one or more defects.

Figure 16:
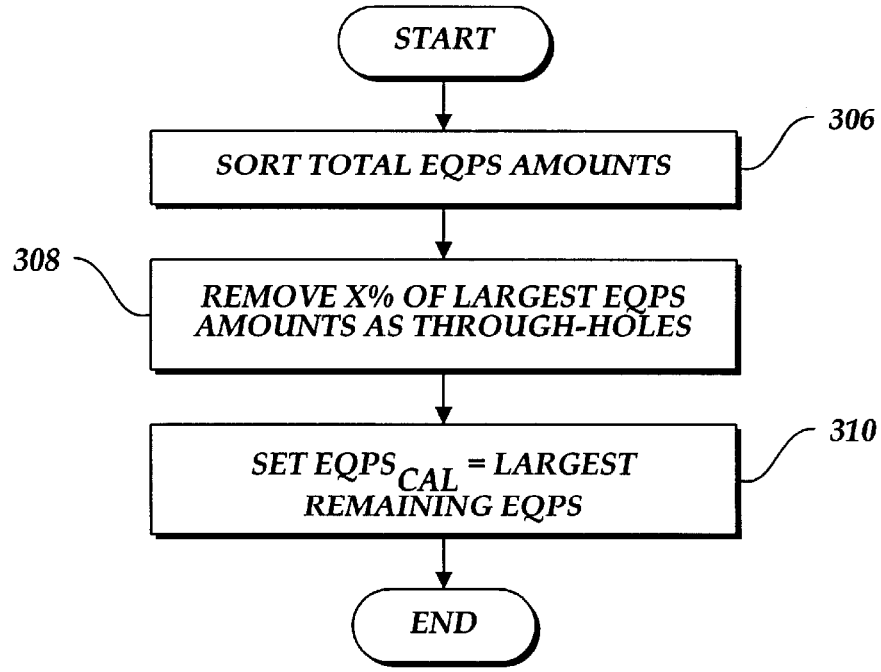
FIG. 16 is a logic diagram of one embodiment of a method to determine a calibration $EQPS_{CAL}$ value.

This is accomplished in one embodiment by assuming that a certain percentage of the most severe pipe defects are 100% through-holes. Referring to FIG. 16, at a block 306 a sort is made of the Total EQPS amounts within the pipe length. At a block 308 a certain percentage of the largest EQPS amounts are removed from consideration as representing 100% through-holes. At a block 310, an EQPS calibration amount, $EQPS_{CAL}$, is set equal to the largest remaining Total EQPS value.

As yet another alternative, a theoretical calibration value and a theoretical nominal value may be calculated using the standard eddy current equations and assumed conductivity and permeability values. This system is best used only when a small portion of a pipeline has significantly different material properties or size than the rest of the pipeline and insufficient information is available to use any of the other methods. This technique may be used further to verify the results of the other methods since permeability varies greatly between different pipelines.

Analyze Defects

Figure 17:
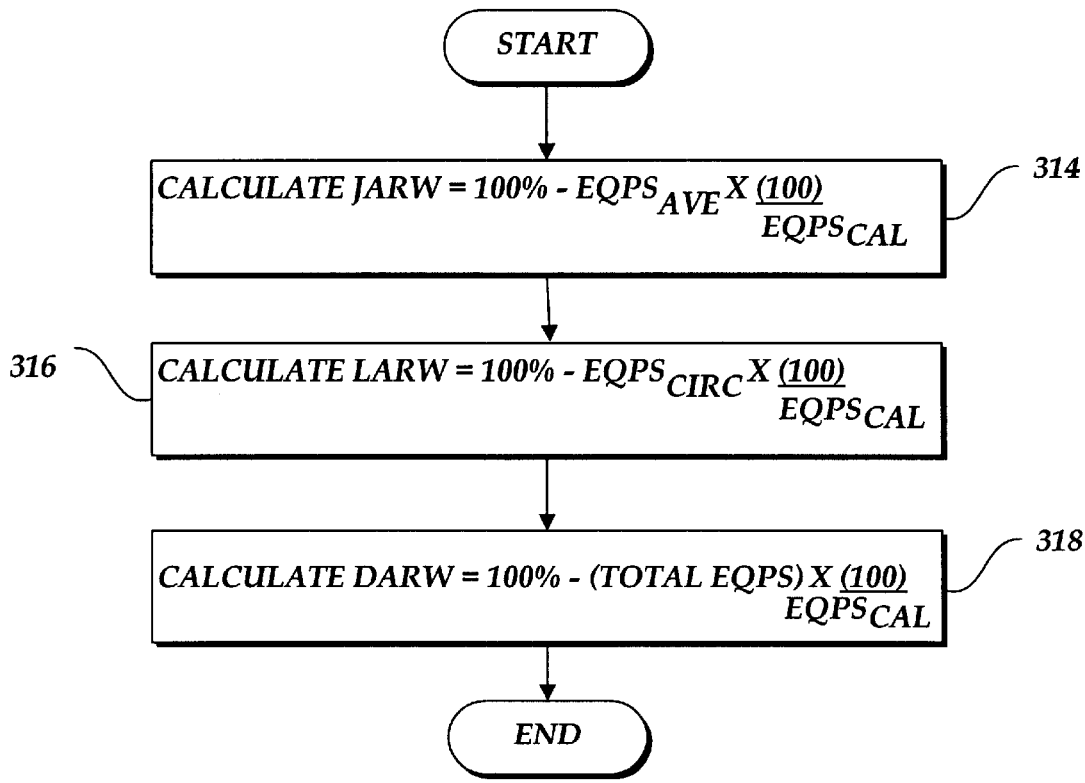
FIG. 17 is a logic diagram of one embodiment of a method of calculating select analysis terms.

Upon defining calibration amounts, assessments of wall thickness may now be made at any point along the pipe length. There are numerous values that may be calculated and displayed. In addition to the basic calculation of remaining wall thickness at a particular defect location, three other terms are useful: the Joint Average Remaining Wall (JARW), the Local Average Remaining Wall (LARW), and the Defect Area Remaining Wall (DARW). The term JARW is reflective of the average percentage remaining wall thickness for a particular pipe length (joint). FIG. 17 illustrates one way in which this average value may be defined at a block 314. As shown:

$$JARW = 100\% - EQPS_{AVE} \cdot \frac{(100)}{EQPS_{CAL}} \quad (5)$$

where $$EQPS_{AVE} = \frac{P_{AVE} - P_{NOM}}{2}$$

and $P_{AVE}$ is the average phase value of the pipe length based on a summation of all phases divided by the total number of phase values in the pipe length. The term EQPS$_{AVE}$ is an indication of the average pipe length condition.

The term LARW is reflective of the percentage amount of circumferential wall loss (usually indicative of corrosion or manufacturing variation) at a defect location. FIG. 17 illustrates one way in which this average value may be defined at block 316. As shown:

$$LARW = 100\% - EQPS_{CIRC} \cdot \frac{(100)}{EQPS_{CAL}} \quad (6)$$

Term DARW is reflective of the percentage amount of total wall loss at a defect location. FIG. 17 illustrates one way in which this average value may be defined at block 318. As shown:

$$DARW = 100\% - (EQPS_{CIRC} + EQPS_{NON-CIRC}) \cdot \frac{(100)}{EQPS_{CAL}} \quad (7)$$

Referring back to FIG. 7, the analysis results are provided to the analyst for review at block 78. This information may be shown in a myriad of ways, including a voltage plane display, a strip chart printout, a text listing, etc. In addition, the results of the analysis can be saved as a text file, a drawing file using GIS information (i.e., a DXF file), or a common separated values (CSV) file. Virtually all of the terms used or calculated in the method are available for output.

Referring back to FIG. 7, it is desirable to include a block 80 in which the output results are checked or verified in some manner. One method of checking is to perform a "result variance estimate". By assuming a measurement error in amplitude and phase are negligible for pipe lengths without corrosion and those at the tip of the defect trace are given by Δa and Δα, respectively. It is further assumed that both αa and Δα are small quantities so that first order approximation is valid. To the first-order approximation, the errors in defect depth and circumferential extent may be given, respectively, by $$\Delta\varphi = \frac{\sin^2\varphi}{a^2 \sin^2\alpha} \cdot \frac{a(a - \cos\alpha)\Delta\alpha - \sin\alpha\Delta a}{1 - \sqrt{2}\sin(\varphi + \pi/4)e^{-\varphi}} \quad (8)$$

and $$\Delta q = (q-1)\frac{\Delta a}{a} + a\cos(\alpha - \varphi)\csc\varphi\Delta\alpha - a\csc^2\varphi\sin\alpha\Delta\varphi \quad (9)$$

Computer Program

Referring to FIGS. 18–47, an embodiment of a computer program formed in accordance with the present invention is provided, in which aspects of the above-described method is implemented. The program is presented herein as a stand-alone system stored in a personal computer, though it may be arranged to be accessed from a server or within a local area network (LAN) configuration. The essential system arrangement requires a computer having input/output capability, memory, and a central processing unit. A user loads a computer application program formed in accordance with the present invention into the computer memory where it is available for execution. The user additionally provides one or more input files of RFT raw data.

Upon activating the program, the user is provided with a graphical user interface (GUI) display screen through which the user can manipulate the RFT raw data into meaningful information regarding pipeline defects, particularly regarding the location and size of defects and their respective remaining wall thicknesses. The user can view the results of the data manipulations through various display means, e.g., monitor, printer, plotter, etc. While Visual C++™ is the preferred GUI programming language of the present invention, it will be appreciated that other event-driven GUI programming languages may be used.

In a preferred embodiment, the computer application program is provided to the user on a floppy disk or other data storage device. The user then installs the program software in a PC having a Windows 95 operating system by conventional key selections such as via the Start Menu—Run command or by double-clicking a Setup file via Windows Explorer. Once the program is installed, it can be launched by double-clicking its associated icon or using other conventional means. It will be appreciated that other operating systems, and methods of installing and invoking the software may be used.

Figure 18:
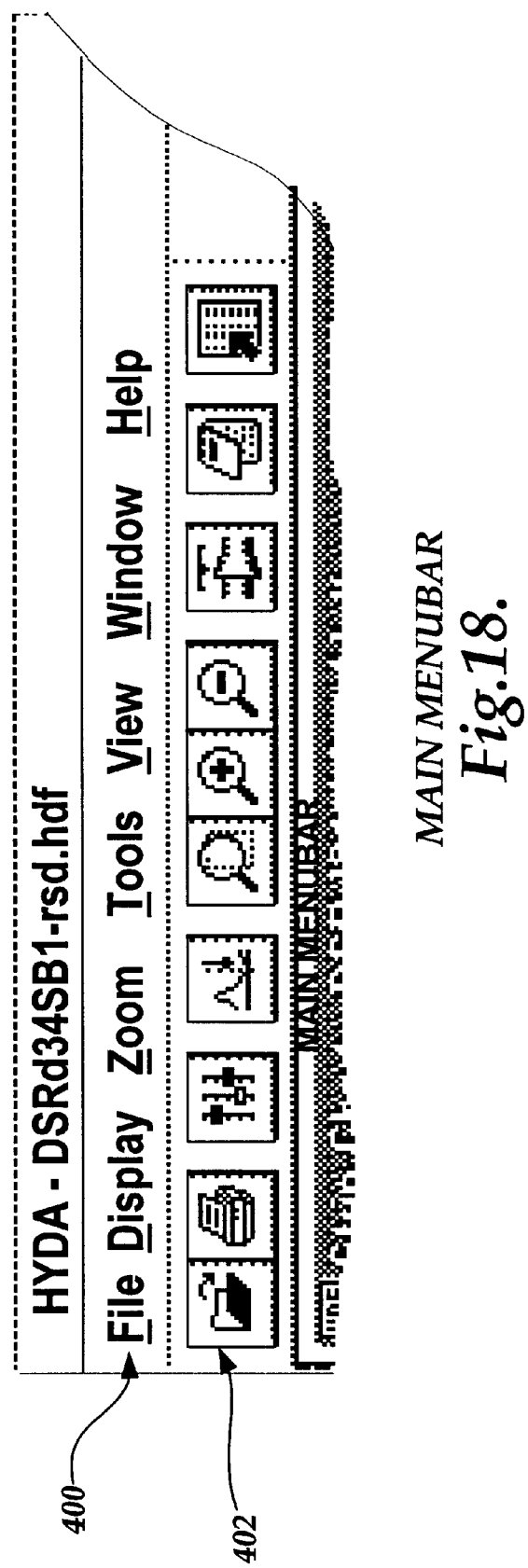

Referring to FIG. 18, upon launching the program, a display window appears having a Main Menubar 400 and a Button Bar 402. These bars provide a number of options to the operator for analyzing and displaying RFT pipeline data. By clicking on a menu item or by using the keyboard to highlight an item, a drop-down menu appears within which the user may scroll to choose from further selections. In the illustration of FIG. 18, the Main Menubar 400 includes items of "File", "Display", "Zoom", "Tools", "View", "Window", and "Help". Prior to having opened a file for analysis, the Main Menubar choices are preferably limited to "File" and "Help" only. The Button Bar 402 includes selectable buttons for accessing those features used frequently.

When "File" is highlighted, a drop-down menu is presented with a list of generic file manipulation selections: Open, to open a data file; Print Setup, to alter printing options; and Exit, to close all files and exit the program.

Figure 19:
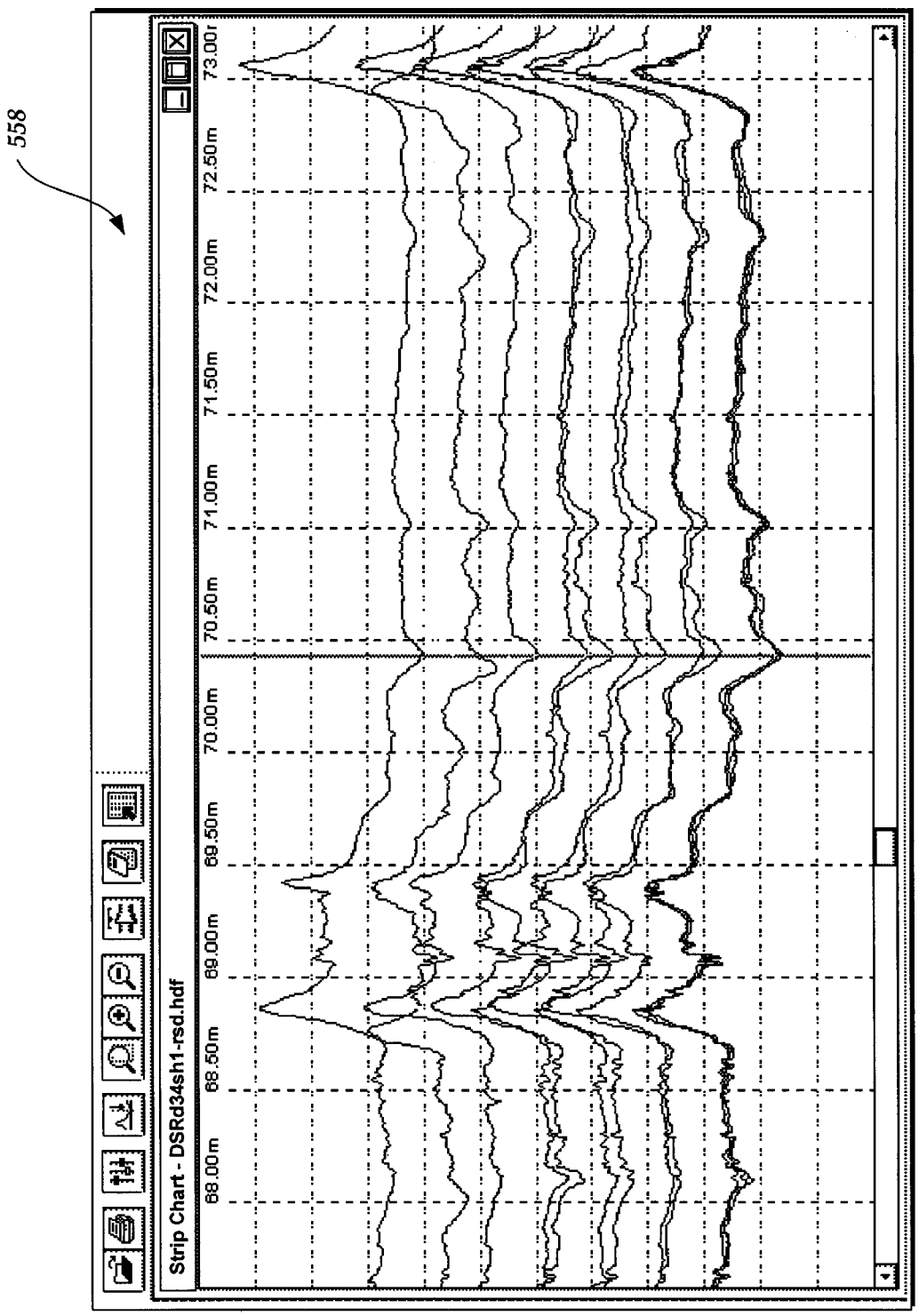

To begin working with a file, the user selects File-Open. A display is provided showing the data files currently accessible to the program and the user. Once a data file is opened, other File menu selections become available, for example, a Print command and a Close file command. After a valid data file has been opened, the program activates the other menu choices so that the user can begin analysis and manipulation of the data. Upon opening a data file, a blank interactive stripchart window 558 in FIG. 19 is displayed on the computer monitor screen. Using the Display features described below, the user can request the program to display the input data of the newly-opened file in the Strip Chart window. FIG. 19 is an example of selected data from a newly opened file. Once the user has progressed through an analysis of the data, two other main interactive windows become available—a Data Explorer window 560 and a Voltage Plane window 562. These items are discussed below with reference to FIG. 39.

The Tools selection in the Main Menubar 400 is the primary selection for manipulating and analyzing the data. The Tools selection is discussed below with reference to FIGS. 20–30. The Display selection allows the user to alter display parameters and is discussed below with reference to FIGS. 31–37. The View selection provides access to the other interactive windows and is discussed below with reference to FIGS. 38 and 39. The remaining selections of "Zoom", "Window", and "Help" provide information similar to conventional Zoom, Window, and Help selections.

Figure 20:
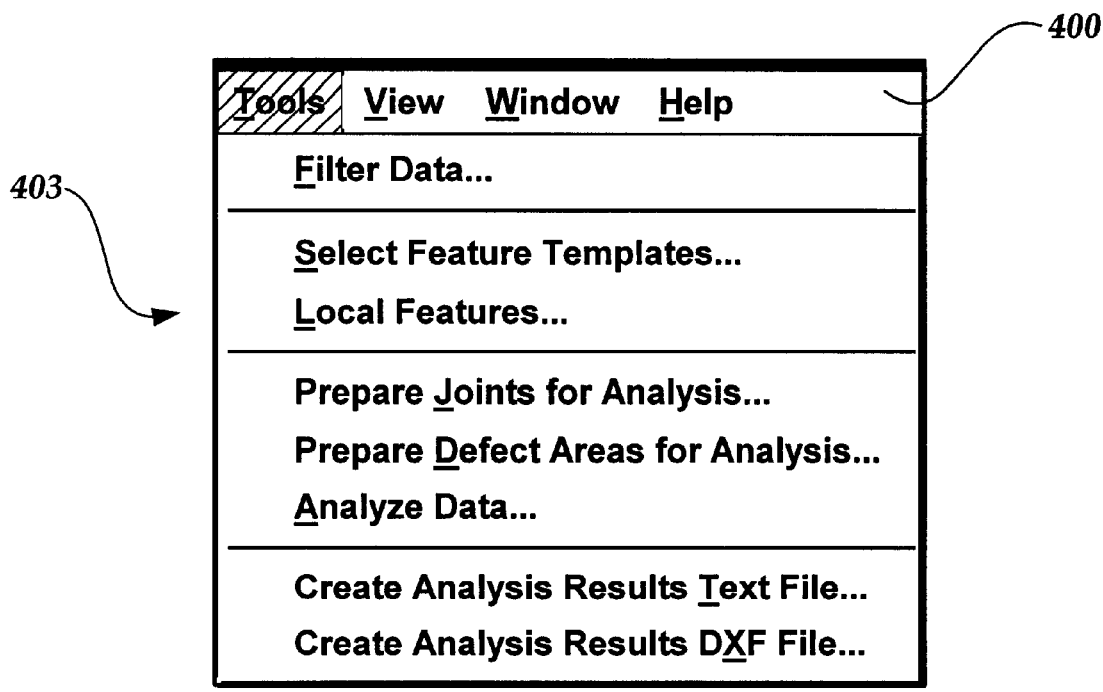

When "Tools" is selected, a drop-down menu 403 of further selections is provided, such as the one illustrated in FIG. 20. The Tools menu is basically a listing of analysis steps, including "Filter Data", "Select Feature Templates", "Locate Features", "Prepare Joints for Analysis", "Prepare Defect Areas for Analysis", "Analyze Data", "Create Analysis Results Text File", "Create Analysis Results DXF File". Because there is an order to the analysis, the selections under Tools are preferably available only after the user has progressed through the proceeding steps. Therefore, some later steps are grayed out (unavailable) until the preceding steps have been completed. For example, when a data file is first opened, the only Tools selection available is the Filter Data selection. Once the data is filtered, both the Filter Data and the Select Feature Templates selections are available. Preferably, completed steps have a checkmark displayed next to them on the Tools drop-down menu. It is possible to go back and redo a previous step if so desired (though, doing so will invalidate the results of the subsequent steps that have been done).

Figure 21:
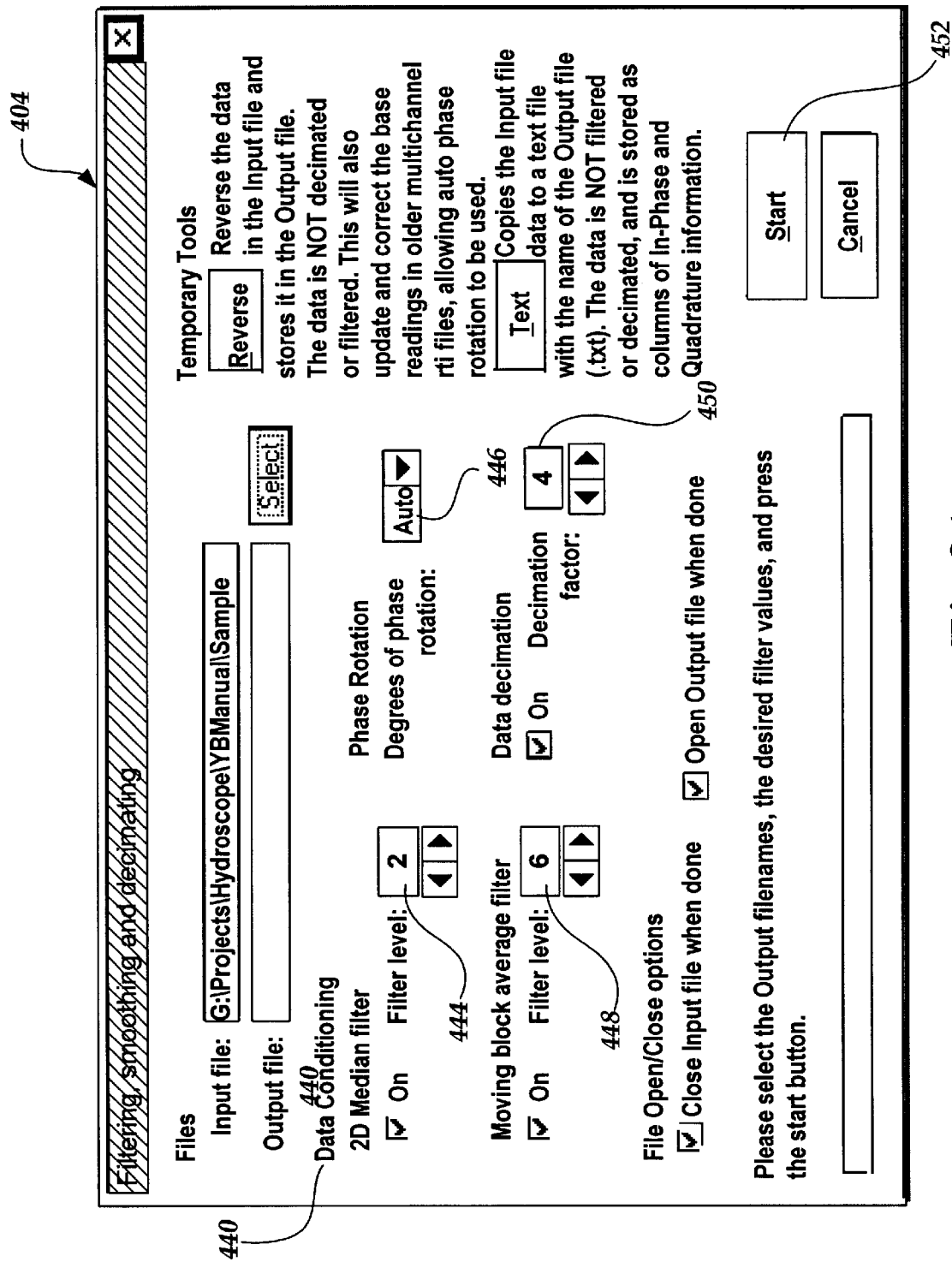

Upon selection of Tool-Filter Data, an interactive display window 404, such as the one illustrated in FIG. 21 titled "Filtering, Smoothing, and Decimating" appears. In one area of the display window, various Data Conditioning options 440 are presented for modification by the user. In the illustration of FIG. 21, the user can activate a median filter and modify its level using an entry box 444, select degrees of phase rotation using a selection 446, activate and select a level for a moving block average filter using an entry box 448, and activate and select a decimation factor at a data decimation entry box 450. The values identified in the Data Conditioning area 440 are used as inputs in the method described above in reference to the filtering, decimating, and smoothing steps of the Prepare Data block 62 shown in FIG. 7. Selection of a Start button 452 initiates the filtering, smoothing, and decimating of the input data according the method shown and described in reference to block 62 in FIG. 7.

Referring back to FIG. 20, upon selection of Tools-Select Feature Templates, an interactive display window appears such as the one illustrated in FIG. 22. A Templates Used box 460 is provided. When a file name is shown in box 460, a list of its individual templates for that file is provided in a listbox 462. These templates are then used an inputs to block 64 of FIG. 7 and particularly block 110 of FIG. 9. By activating a Browse button 466, the program searches the appropriate files and allows the user to select a template file. The template is then listed in a selection area 470 with its file name displayed in block 461. The user can select entries from the available templates selection box 470 and add them to a templates used listbox 462 by highlighting the entry and then clicking on an Add button 468. A preview area 474 allows the user to view the template shape and other characteristics. After clicking the Add button 468, the template name appears in the templates used listbox 462 where all the templates to be used in the files are listed. Three buttons are available in area 464 to Delete, Rename, and add New templates to the templates used listbox.

Figure 23:
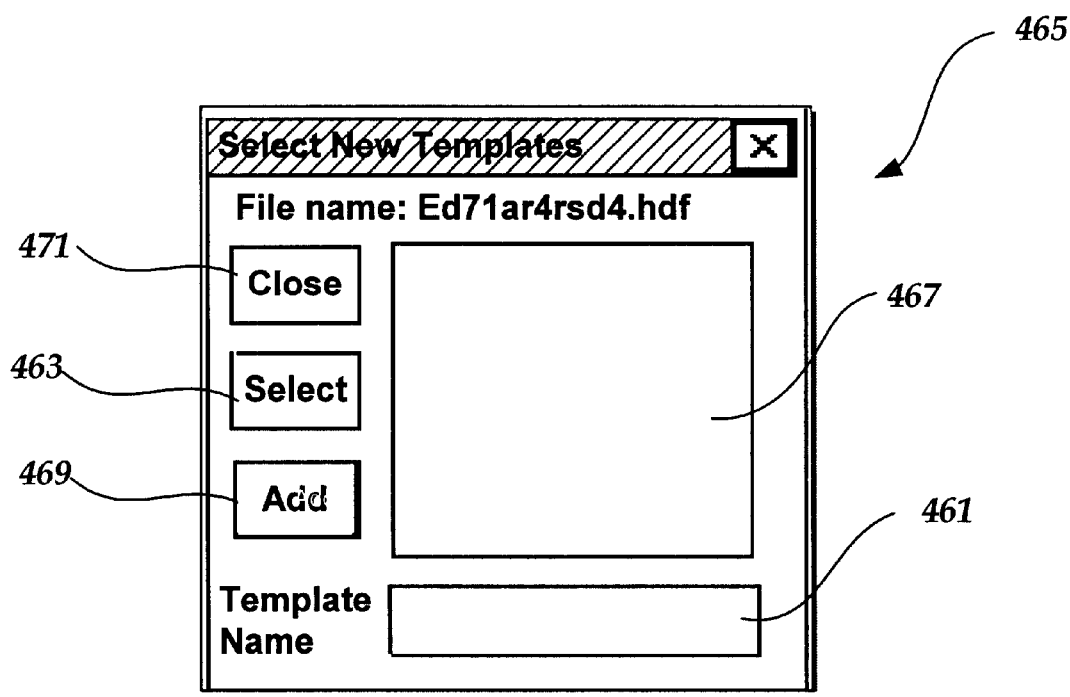

If the New button is selected, a display screen 465, such as the one shown in FIG. 23, appears. The user enters a name in an entry box 461. The user then clicks on a Select button 463 that changes the mouse cursor control to a copy mode. In the copy mode, the mouse may be used to select and copy information directly from the strip chart window 558 and place it in a view window 467. Since all data points in the stripchart include basic information as to their location and values, the copied portion contains sufficient information for use as a feature template. Clicking an Add button 469 results in the template name being transferred to the template list in the templates used listbox 462 in FIG. 22. A Close button 471 may be clicked to exit the Select New Templates display and return to the screen of FIG. 22.

Referring back to FIG. 22, when the user is satisfied with the selected feature templates, clicking on an OK button 472 causes the program to store the templates displayed in the templates used listbox 462 for later use in method step 64 of FIG. 7.

Figure 24:
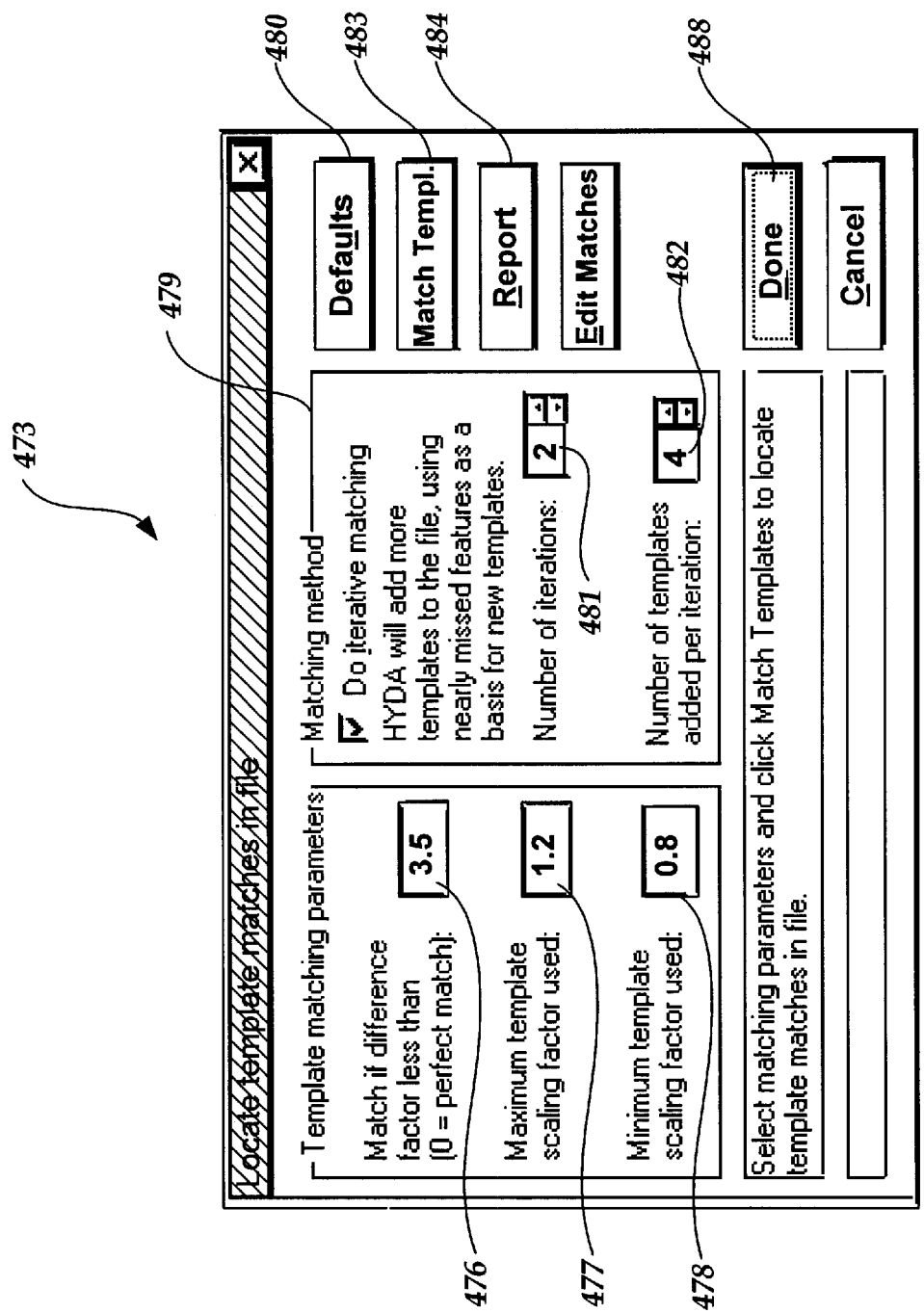

Referring back to FIG. 20, once the tasks of Filter Data and Select Feature Templates have been completed, the user selects Tools-Locate Features. An interactive display window 473, such as the one shown in FIG. 24, is provided. This window allows the user to pre-define various template matching parameters. A Match value can be set at an entry box 476, as well as maximum and minimum scaling factors at entry boxes 477 and 478. These values are provided to define the Threshold_Amount, and scaling limits, respectively, discussed above with regard step 64 in FIG. 7.

Referring back to FIG. 24, a matching method area 479 is provided that allows the user to activate iterative template matching and to pre-define the number of iterations and the number of templates added per iteration. Should the user elect, a defaults button 480 can be selected to allow the program to use default entries. If the Matching method box is checked, the values of Number of iterations 481 and Number of templates added per iteration 482 will be used to define the same in the subsequent performance of the template matching method steps.

Figure 25:
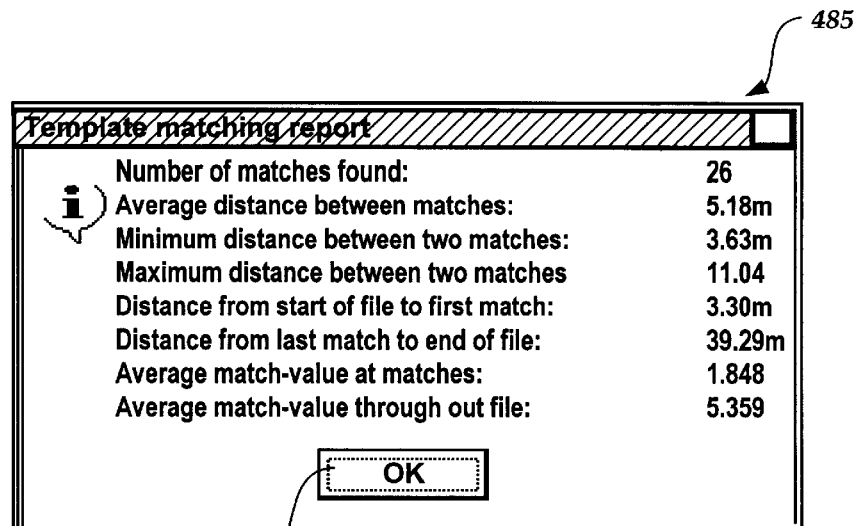

Once the user is satisfied with the template matching parameters and matching method iterations, the user clicks on a Match Template button 483 and the program locates template matches in the file as described above with reference to the methods of FIGS. 9 and 10. Once template matching is complete, control returns to the display window 473 where the user can click on a Report button 484 to review the results of the template matching. FIG. 25 illustrates an example template matching report 485 that lists various results of the matching routine calculated by the method. Shown is a listing of the number of matches found, the average distance between matches, the minimum and maximum distance between two matches, the distance from the start of file to the first match, the distance from the last match to the end of file, the average match value at matches, and the average match value throughout the file. Clicking on an OK button 486 returns the user to the prior display window 473. Clicking on a Done button 488 in a display window 473 ends the template matching step.

Figure 26:
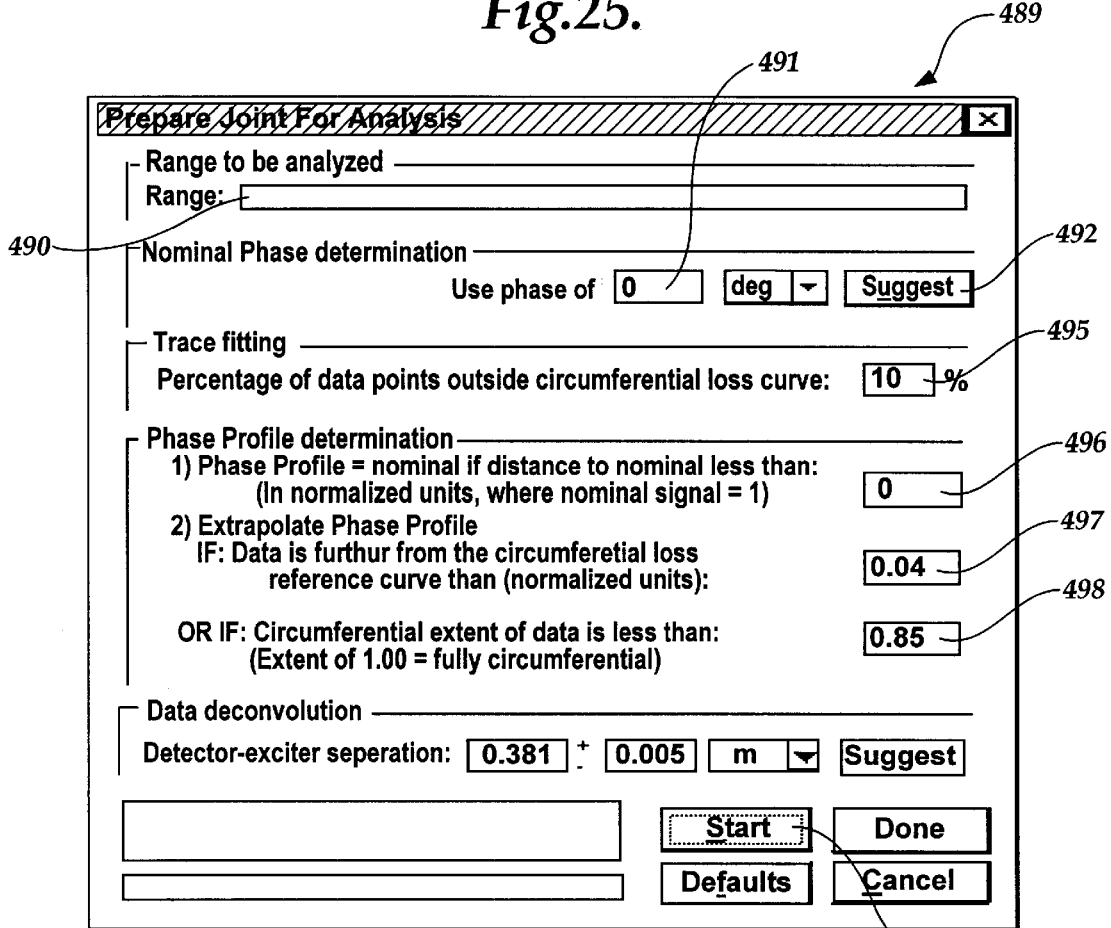

Continuing in the analysis, the user next selects Tools-Prepare Joints for Analysis from the tools menu 403. An interactive display window 489 such as the one shown in FIG. 26 is provided in which the user can alter parameters used in parsing the data into pipe lengths and in determining nominal and Phase Profile values. The range of pipe length prepared is shown in an entry box 490. Later, re-evaluation of nominal signal may cause one or more of the pipe lengths to be re-prepared. The user may enter a nominal phase determination using an entry box 491. The numerical amount shown in the entry box 491 is the value that will define the nominal phase value $P_{NOM}$ used in the analysis at block 52 of FIG. 7.

Figure 27:
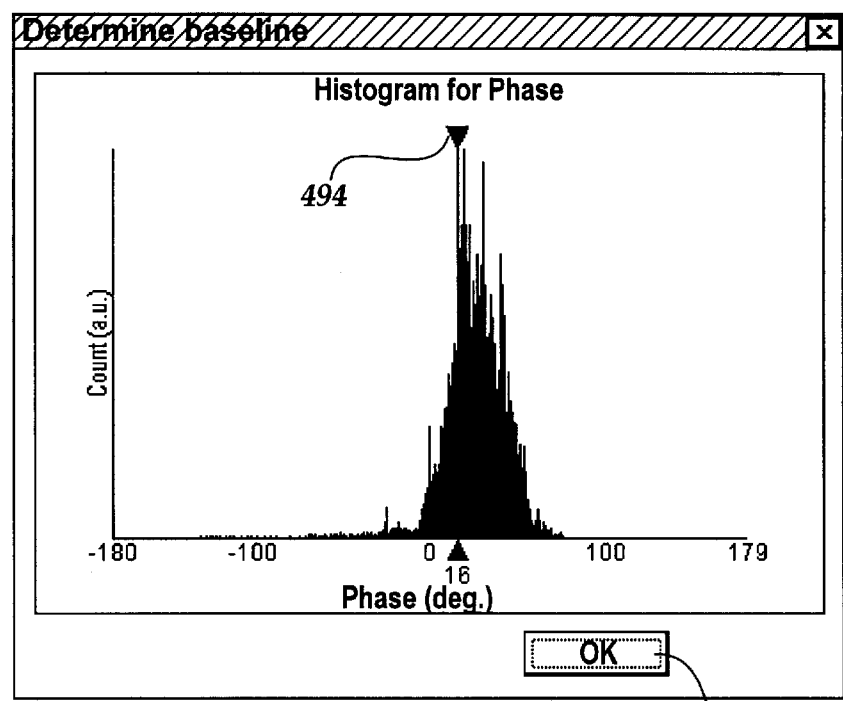
Figure 30:
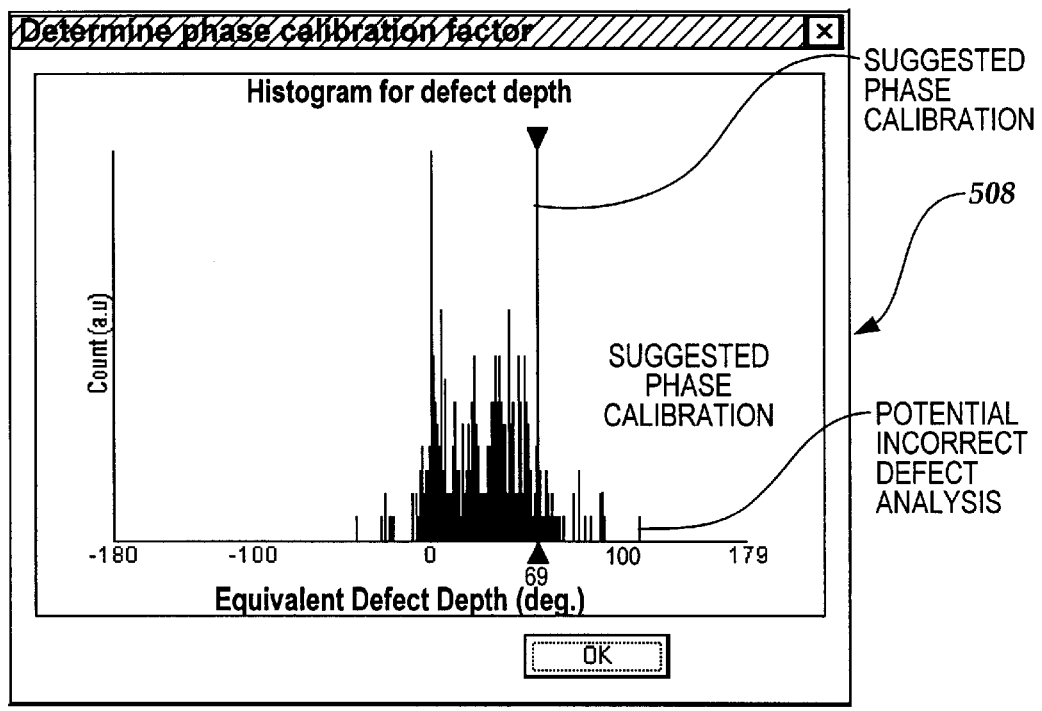

Clicking on a Suggest button 492 will result in a phase histogram display 493 such as the one shown in FIG. 27. The program creates the histogram by counting the number of data points at each represented phase value in the selected data range and displaying a plot of the count verses phase value. An indication bar 494 is provided in the histogram at the point for which a default percentage of phase values will be less than nominal. The phase value of the indication bar 494 is calculated using the method described above with reference to block 160 shown in FIG. 11. Upon clicking an OK button 496, the user is returned to the Prepare Joint For Analysis display 489 of FIG. 26, with the phase value of the indication bar 494 being inserted into the entry box 491. An alternative means of selecting the nominal phase is to define a data point by an index or location and to then use its phase value.

Referring to FIG. 26, a Trace Fitting entry box 495 is available for the operator to enter a percentage of data points to lie outside the circumferential Reference Curve in the method step of block 174 of FIG. 11. A Phase Profile entry box 496 is available to allow the user to adjust the NOMINAL_THRESHOLD margin discussed previously and shown in FIG. 12. An Extrapolation Phase Profile entry box 497 allows user-entry of a particular REFERENCE_CURVE_THRESHOLD margin (shown in FIG. 12). An Extent entry box 498 allows user-entry of a particular EXTENT_THRESHOLD (also shown in FIG. 12).

Once the user is satisfied with the parameters to be used in preparing the joints for analysis, he or she clicks on a Start button 500. This causes the program to proceed through the selected data range, parsing the data into pipe lengths, determining the nominal values, and determining the Phase Profile of the pipe length data points. The values shown in the entry boxes 490, 491, 495, 496, 497, 498 are used in this analysis as described above.

The logic of FIG. 7 indicates that a selected data file is first parsed into pipe-lengths and then a complete analysis is performed on a joint-by-joint basis. As implemented in the described computer program, the logic instead proceeds by accomplishing a single task at each pipe length before moving to the next task. Either arrangement is acceptable. In the embodiment of a computer program, however, it is easier for the user to sequence through a limited number of analysis steps as opposed to sequencing through a potentially very long list of pipe lengths. However, means for the user to modify the analysis of individual pipe lengths should be supported. In a preferred embodiment, such means is supported by the Data-Explorer window.

Figure 28:
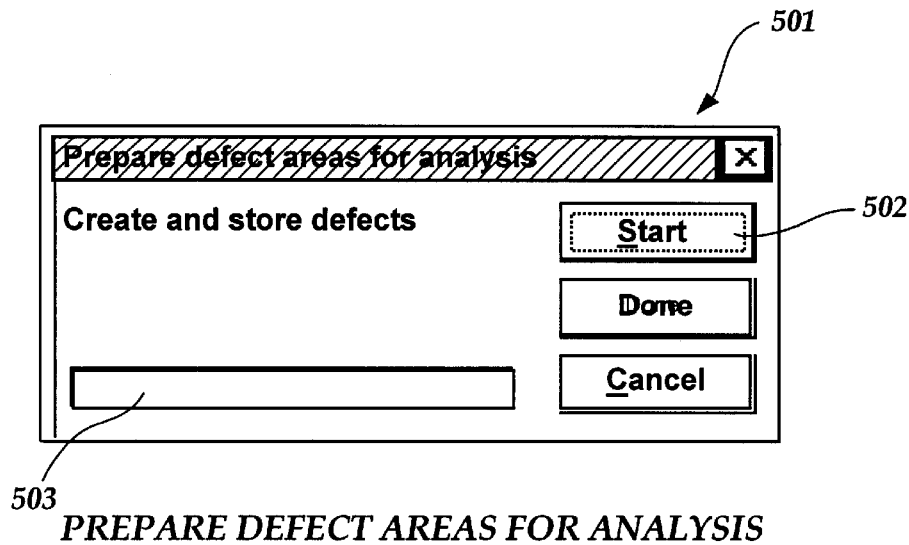

Continuing on in the analysis, the user next selects Tools-Prepare Defect Areas for Analysis and a display window 501 is provided such as the one illustrated in FIG. 28. The user is required only to initiate the start button 502 and the program will locate potential defects and determine the total EQPS at each defect using a method such as that described with regard to block 70 shown in FIG. 7. The status bar 503 indicates the progress of this step as it is being completed.

Having completed preparing the defect areas, the user next selects Analyze Data from the Tools menu. This causes a display window 504 to appear, such as the one shown in FIG. 29. The operator can select a calibration phase and percentage defect depth at entry box 505 or 506, respectively, thereby defining the linear relationship between EQPS and a defect depth. Alternatively, the user may click on a Suggest button 507, and the program will calculate a calibration value using the defect EQIS calibration method discussed above with regard to step 72 shown in FIG. 7. Clicking on Suggest 507 additionally causes a histogram 508 to be displayed such as the one shown in FIG. 30. The histogram is calculated by counting the number of Total E(QPS values at the same phase value and plotting the numbers counted versus degrees of phase and indicating the suggested EQPS value to use for calibration.

Figure 29:
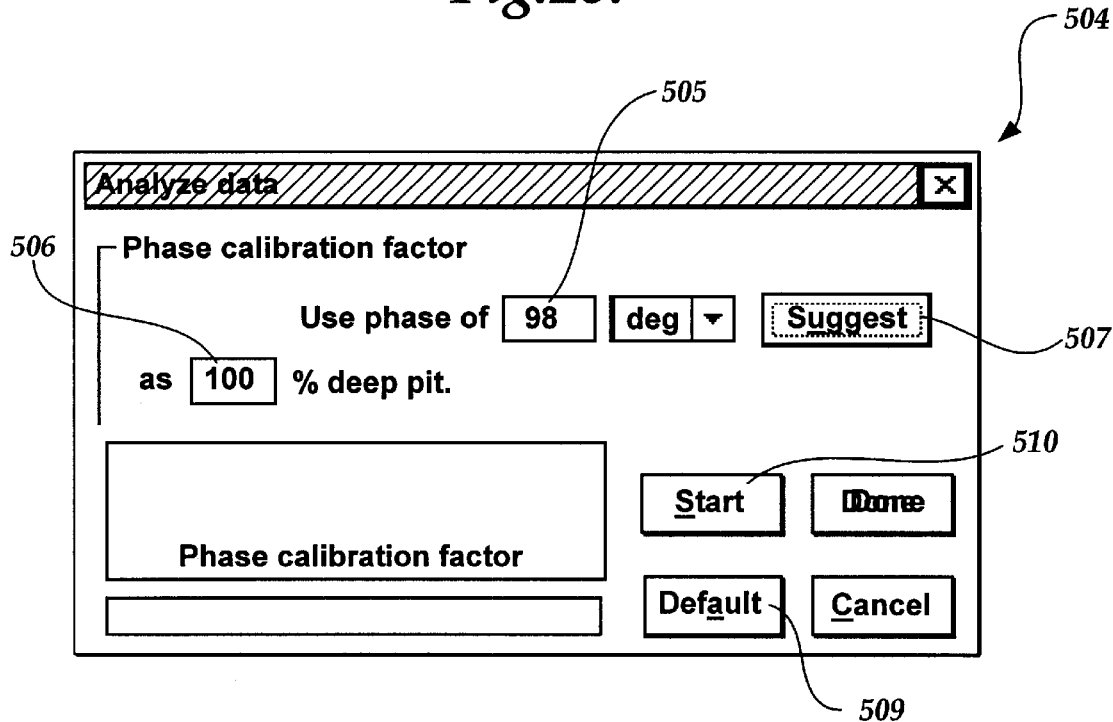

Similarly, in window 504 of FIG. 29, the user can click on a default button 509 and the program will select and use default calibration information. To initiate the analysis of the data, the user clicks on a Start button 5 10. Since all of the required parameters and input values are now available, the program can analyze the defects according to the methods described in step 74 shown in FIG. 7. Afterwards and referring back to FIG. 20, the operator may select the tasks of downloading the data result into a text file via Tools-Create Analysis Results Text File. The operator may also choose to download data results into a Drawing exchange Format (DXF) file via selection of Tools-Create Analysis Results DXF File. This is particularly useful in downloading GIS information (if sufficient amounts have been entered and analyzed as described below).

Once the analysis is complete, the selected data file has been analyzed in accordance with the present invention method and is now ready to be reviewed and manipulated by the operator at the display monitor. A useful feature of this program's user interface is that it allows the user to display certain aspects of the analysis, alter one or more of the various analysis parameters, and redo the analysis using the altered parameters. In this way, the operator can "play" with the data analysis and results.

Figure 31:
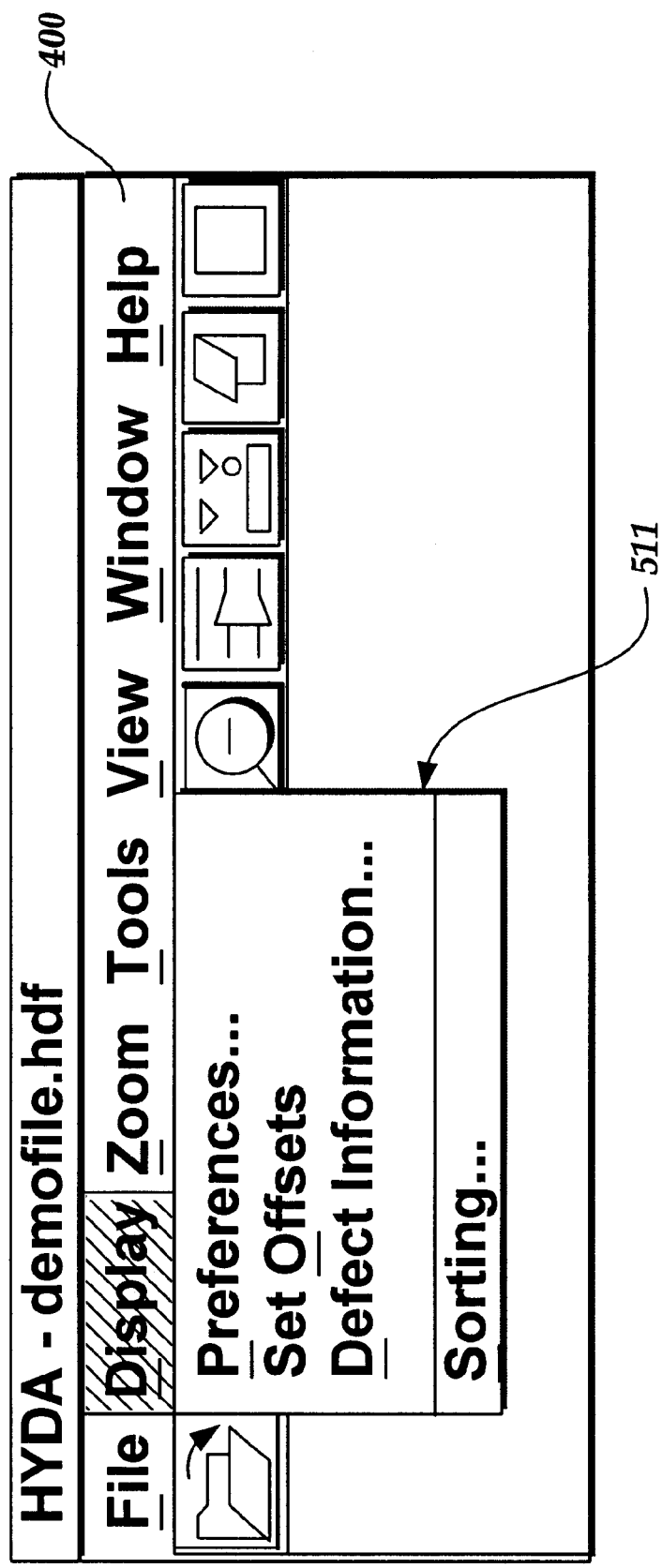

Referring to FIG. 31, when "Display" is clicked on, a pull-down menu 511 appears to provide the user with an opportunity to customize various display features. Shown in FIG. 31 are the selections of Preferences, Set Offsets, and Defect Information. Once an analysis has been performed using the Tools selection, a Sorting selection is made available under the Display selection as well.

Figure 32:
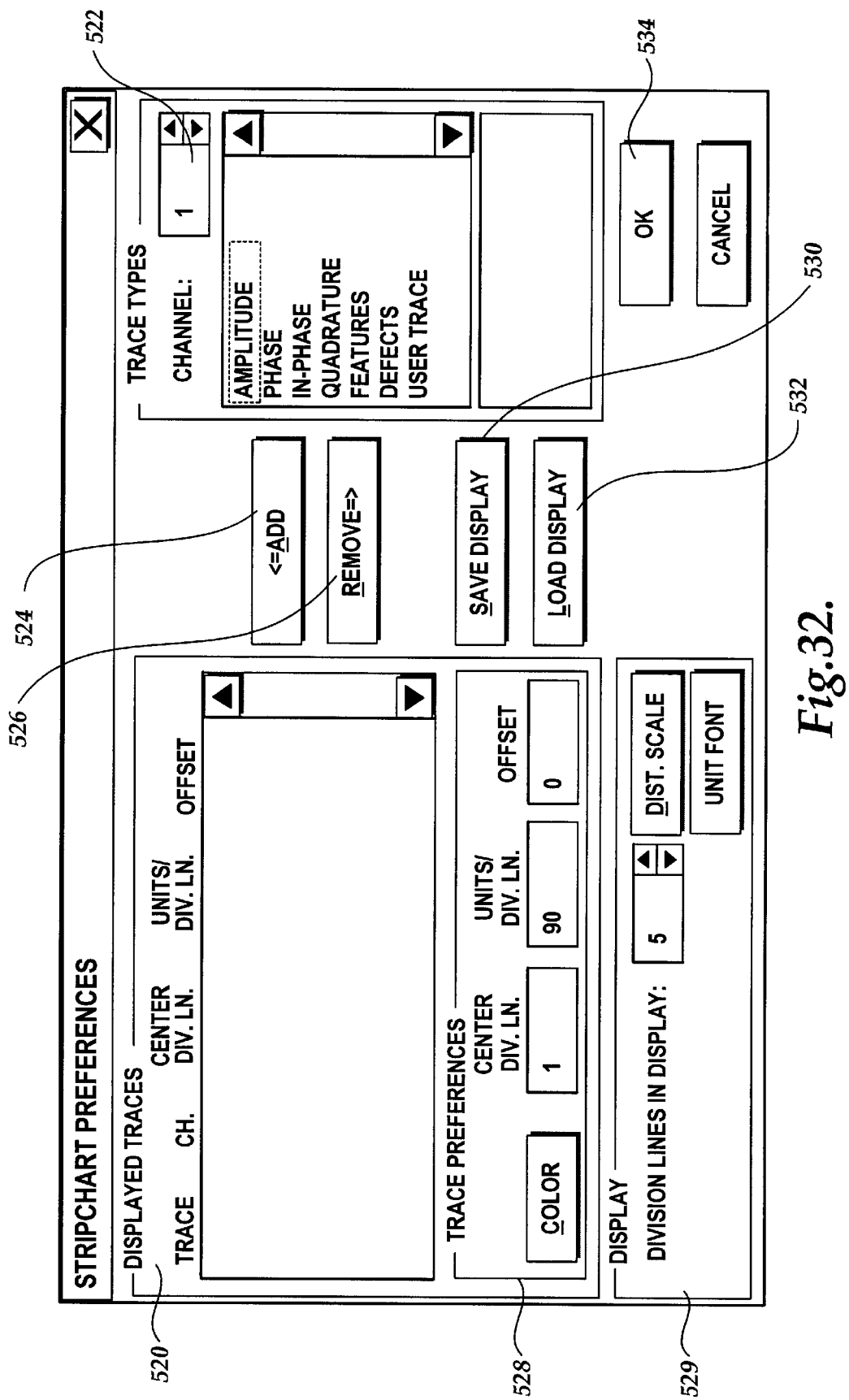

Initial selection of Display-Preferences results in a relatively blank interactive display window, such as the one illustrated it, FIG. 32. Through this window the user can alter various display parameters for the stripchart. The Preferences window changes depending on whether a stripchart is the active window or Data Explorer is the active window (described below with reference to the View selection).

Referring to FIG. 32, on the left hand side is an area 520 titled Displayed Traces which will list the traces displayed on its corresponding stripchart. It is empty in FIG. 32 because no traces have yet been selected. On the right hand side is an area 522, titled Trace Types, that lists the types of items that may be chosen for display on the stripchart. The user may also select from various data channels should more than one be available. Add and Remove buttons 524, 526 are available for adding or removing traces to or from the Displayed Traces list. Each listed display trace has a corresponding set of preferences at an area 528 made available when a trace is highlighted. A Display area 529 allows the operator to alter the display of division lines (i.e., the horizontal dashed lines in the strip chart display).

Figure 33:
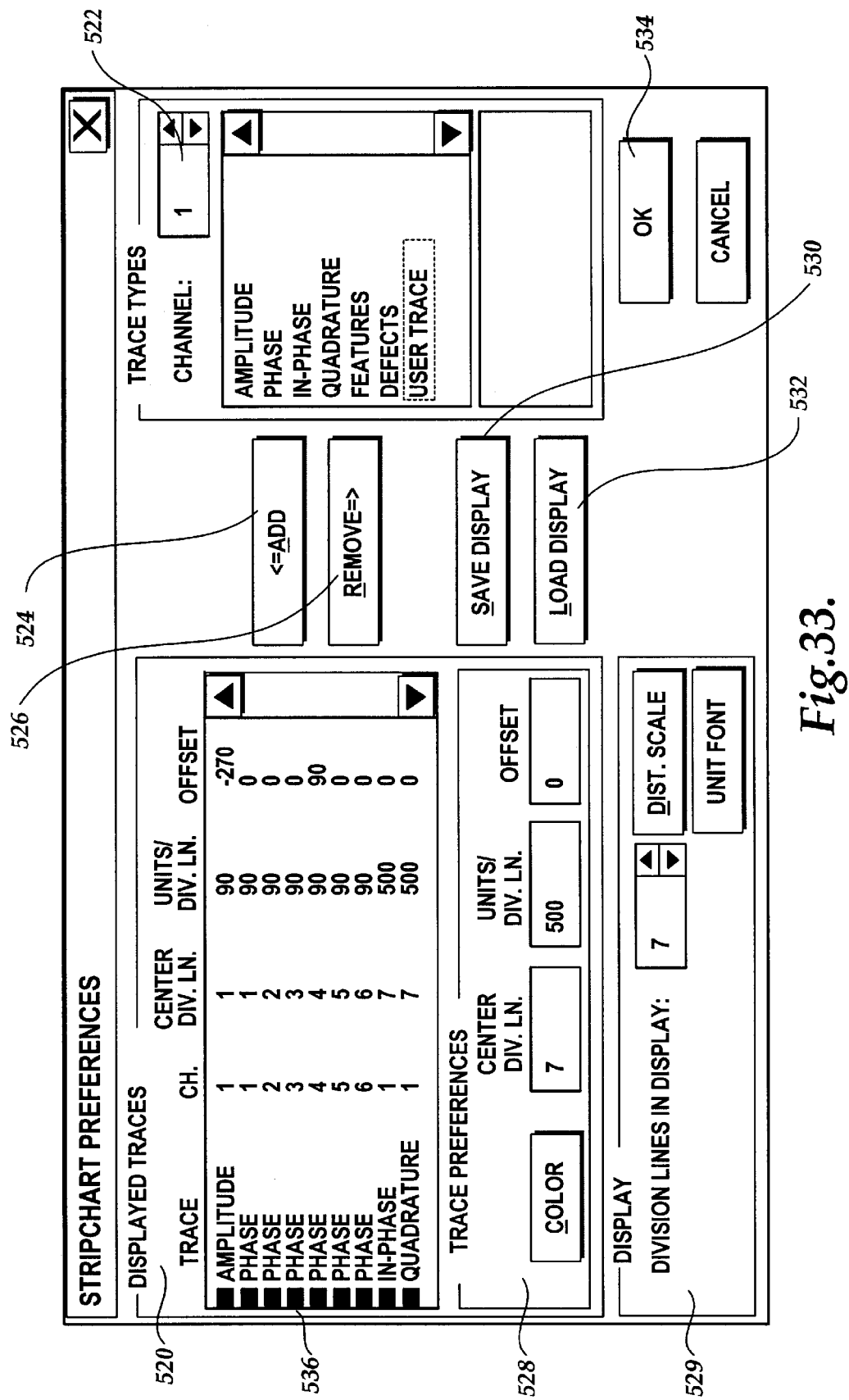

Once the operator has selected the strip chart preferences, he or she may save the display parameters by clicking a Save Display button 530. Conversely, the operator can load a particular stripchart display trace file by clicking on a Load Display button 532. Once the operator has modified the strip chart preferences as desired, the operator selects an OK button 534 and the changes are incorporated into the corresponding display. FIG. 33 is a sample Stripchart Preferences window showing traces of Amplitude, Phase, In-phase, and Quadrature from various channels. Each trace has a color identification box 536 illustrating the color that the trace will have on the stripchart display 558 of FIG. 39.

Figure 34:
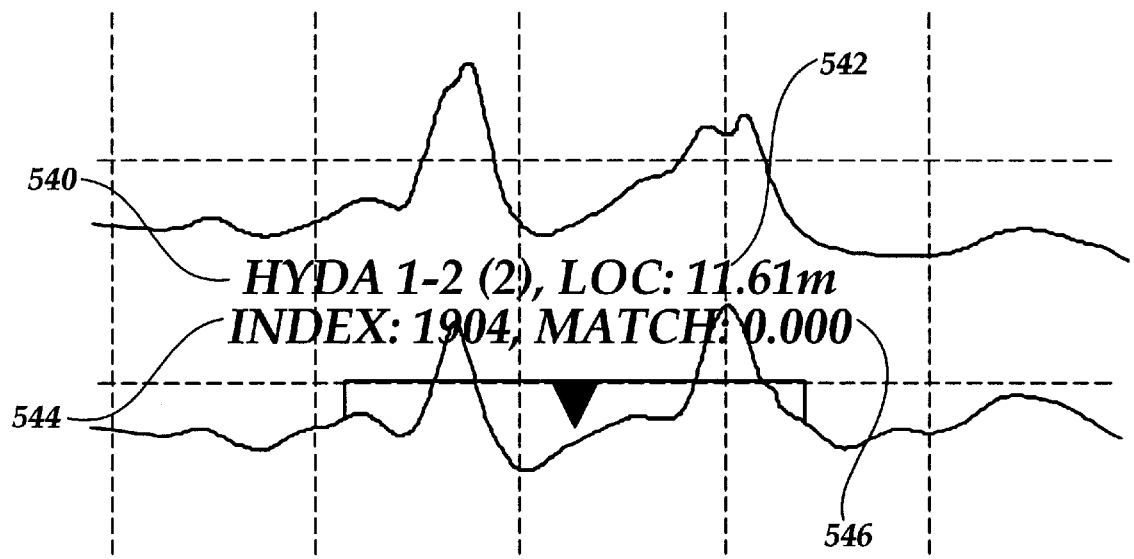
Figure 35:
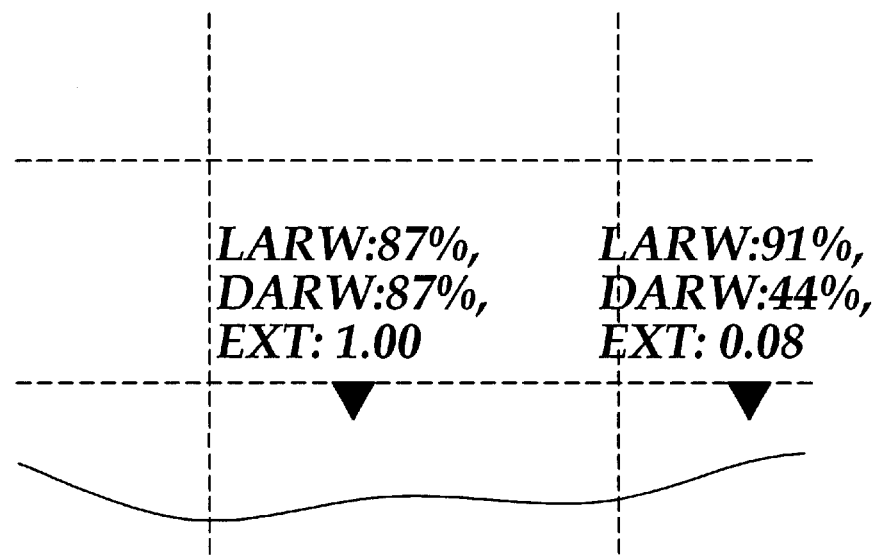

Using the Stripchart Preferences window, the user can further cause a text block and graphical indicator to appear on the stripchart at a match feature or pipe defect location under certain circumstances. FIG. 34 illustrates such a display for a feature match. A template name 540 is shown that was used to make the feature match. A location 542 in meters is shown relative to the start of the data file. An index 544 is shown that is the number assigned to that piece of data. A match 546 is shown corresponding to its calculated Match_Difference_Factor. In FIG. 35, two Defect Text areas are shown as they appear on the stripchart at their respective defect locations. The above-calculated terms of LARW, DARW, and Extent are provided for each Defect Text. See above for description and calculation of these items.

Figure 36:
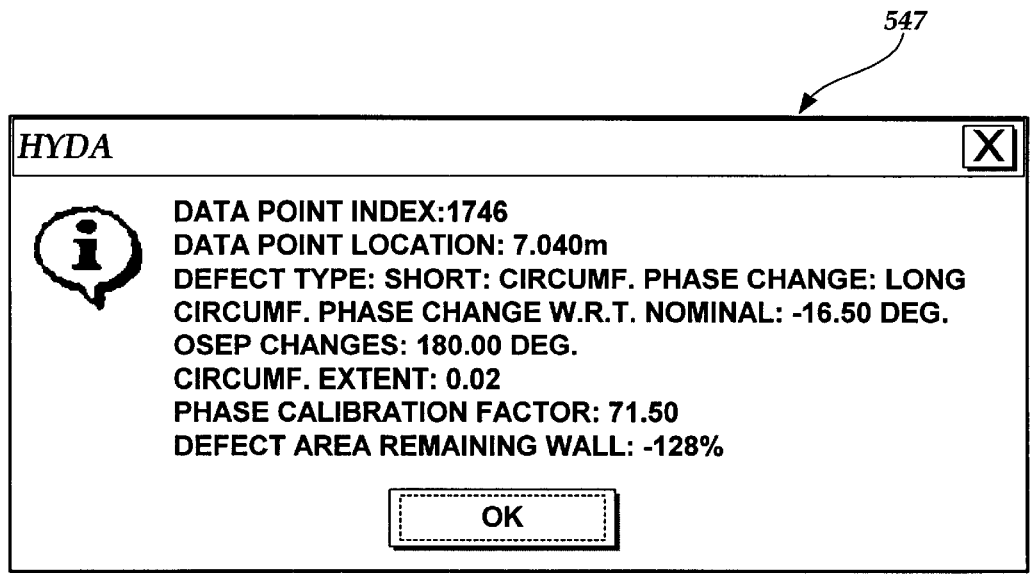

Selection of Display-Defect Information on the Display Menu 571 in FIG. 31 results in a defect summary display 547 such as the one shown II FIG. 36. The summary includes the data point index; the data point location the defect type; the defect circumferential phase change with respect to nominal; the one-sided EQPS phase change (i.e., $EQPS_{NON-CIRC}$); the circumferential extent; the phase calibration factor used; and the defect area remaining wall percentage.

Referring back to FIG. 31, a Display-Sorting selection is made available once the analysis steps of the Tools menu have been completed. Selection of Display-Sorting results in the display of a Sort/Filter Results window such as the one shown in FIG. 37. The majority of the features available in this window are for determining the order in which results of the analysis are shown, and limiting the number of results displayed in the Data-Explorer window.

Figure 38:
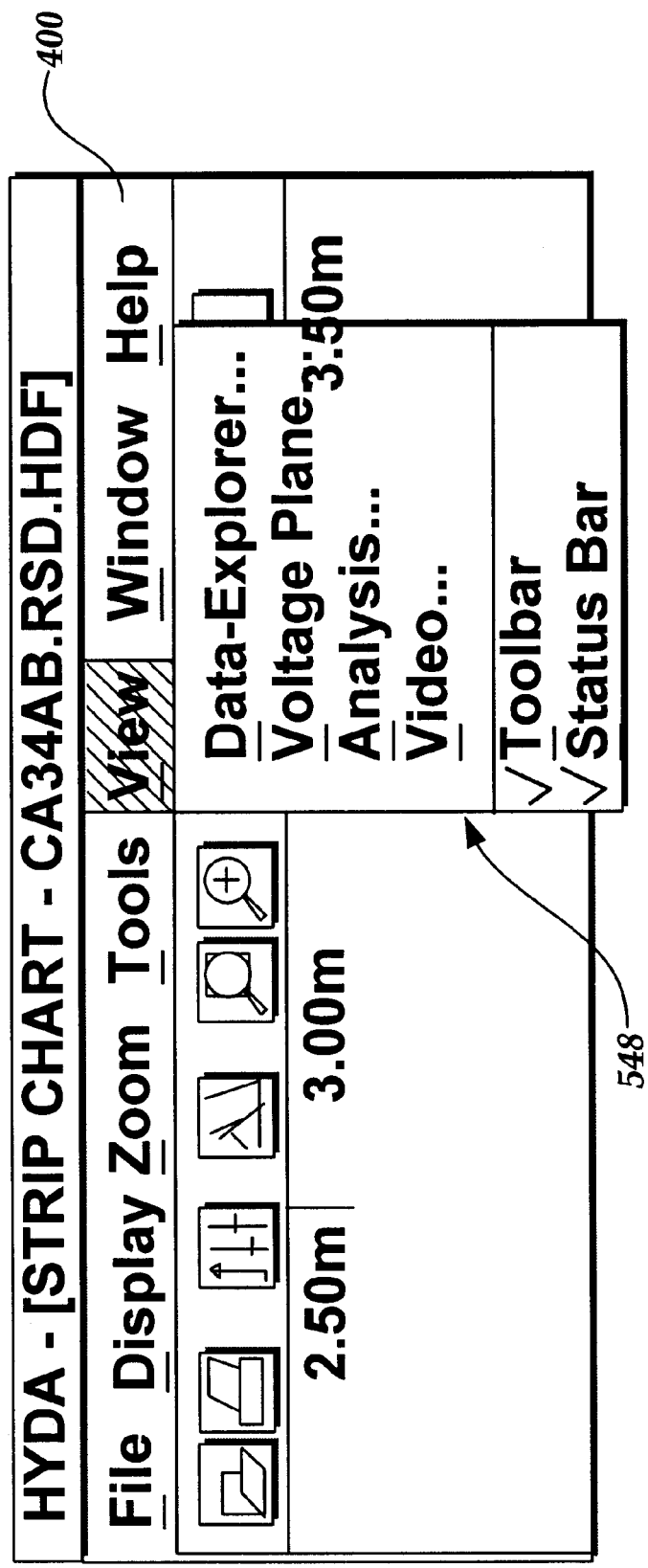

FIG. 38 illustrates the pull-down menu 548 obtained from selecting the View option in the Main Menubar 400. By selecting View-Data-Explorer, an active spreadsheet window 560 is displayed such as the one shown in the lower left hand corner of FIG. 39. The Data-Explorer window 560 is capable of handling huge amounts of data. This window may be organized in various ways so that the data and the analysis results are easily managed. By selecting View-Voltage Plane, a voltage plane display 562 is provided such as the one shown in FIG. 39 in the upper right hand corner. The voltage plane window displays whatever relevant data is shown in the stripchart window 558. The stripchart display 558 is located in the upper left hand corner. Further, by selecting View-Analysis, an Analysis display box 564 is shown in the lower right hand corner of FIG. 39. Using the four windows shown in FIG. 39, the operator can view various aspects of the data and the analysis results.

Figure 40:
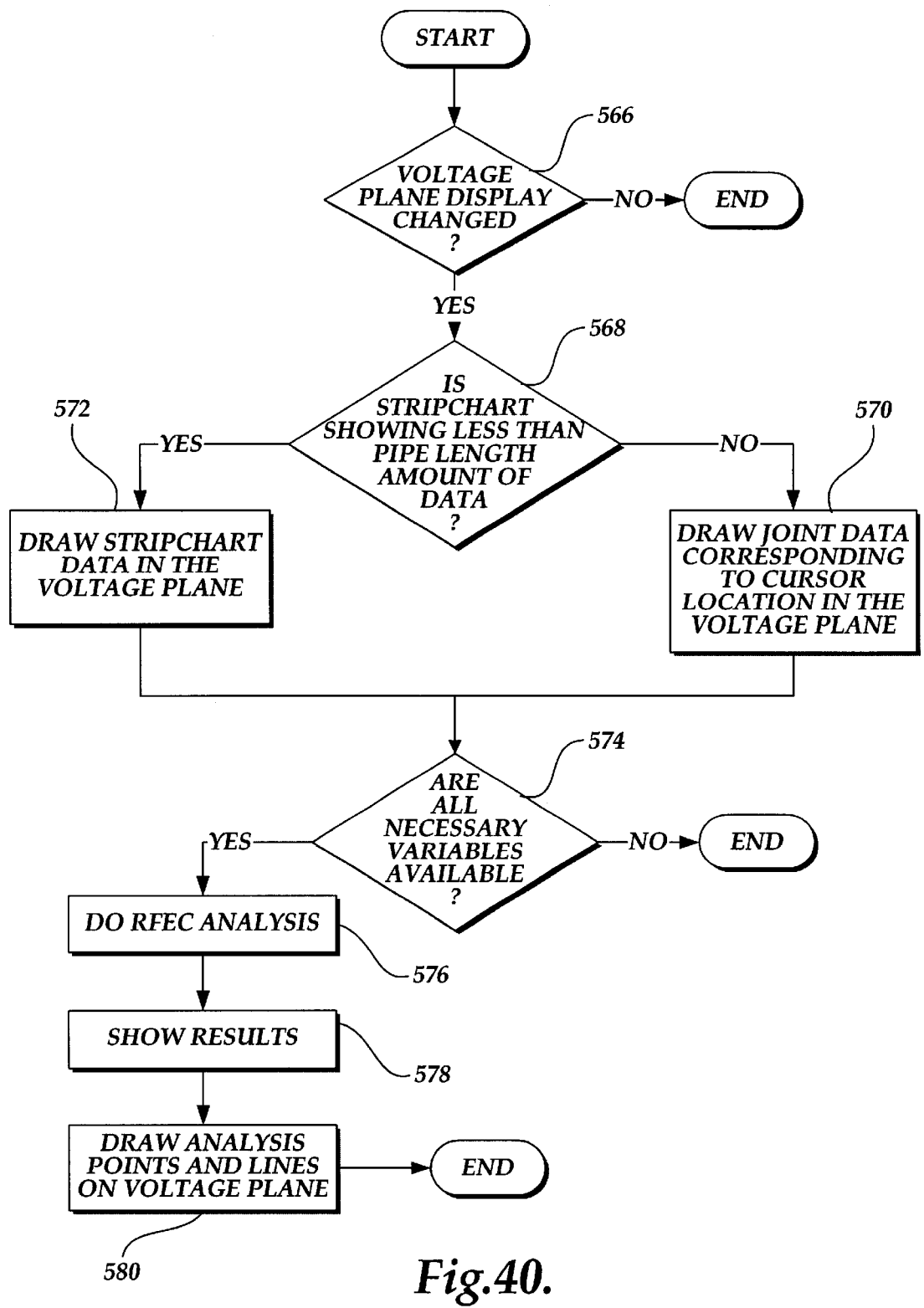
Figure 42:
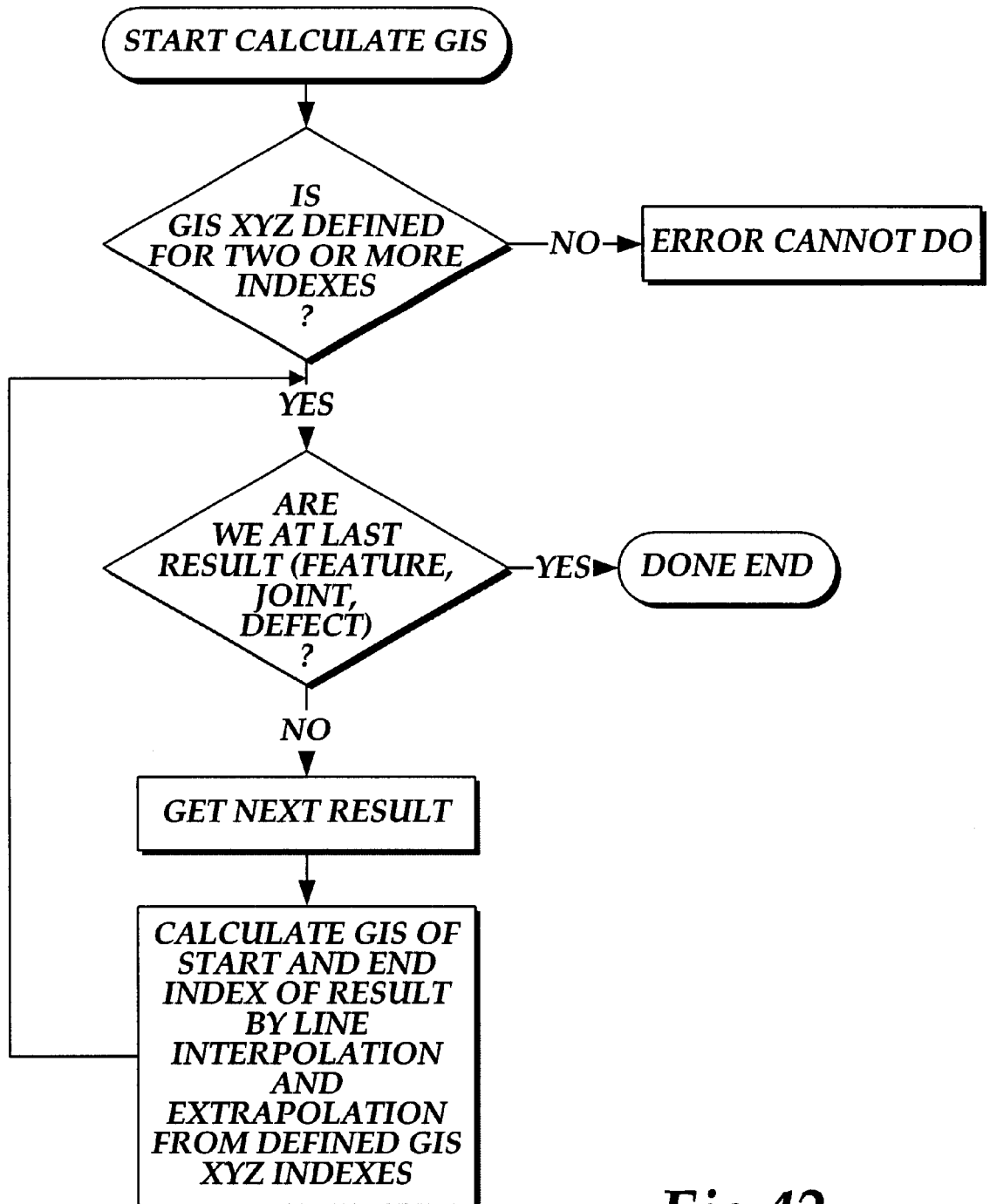
Figure 43:
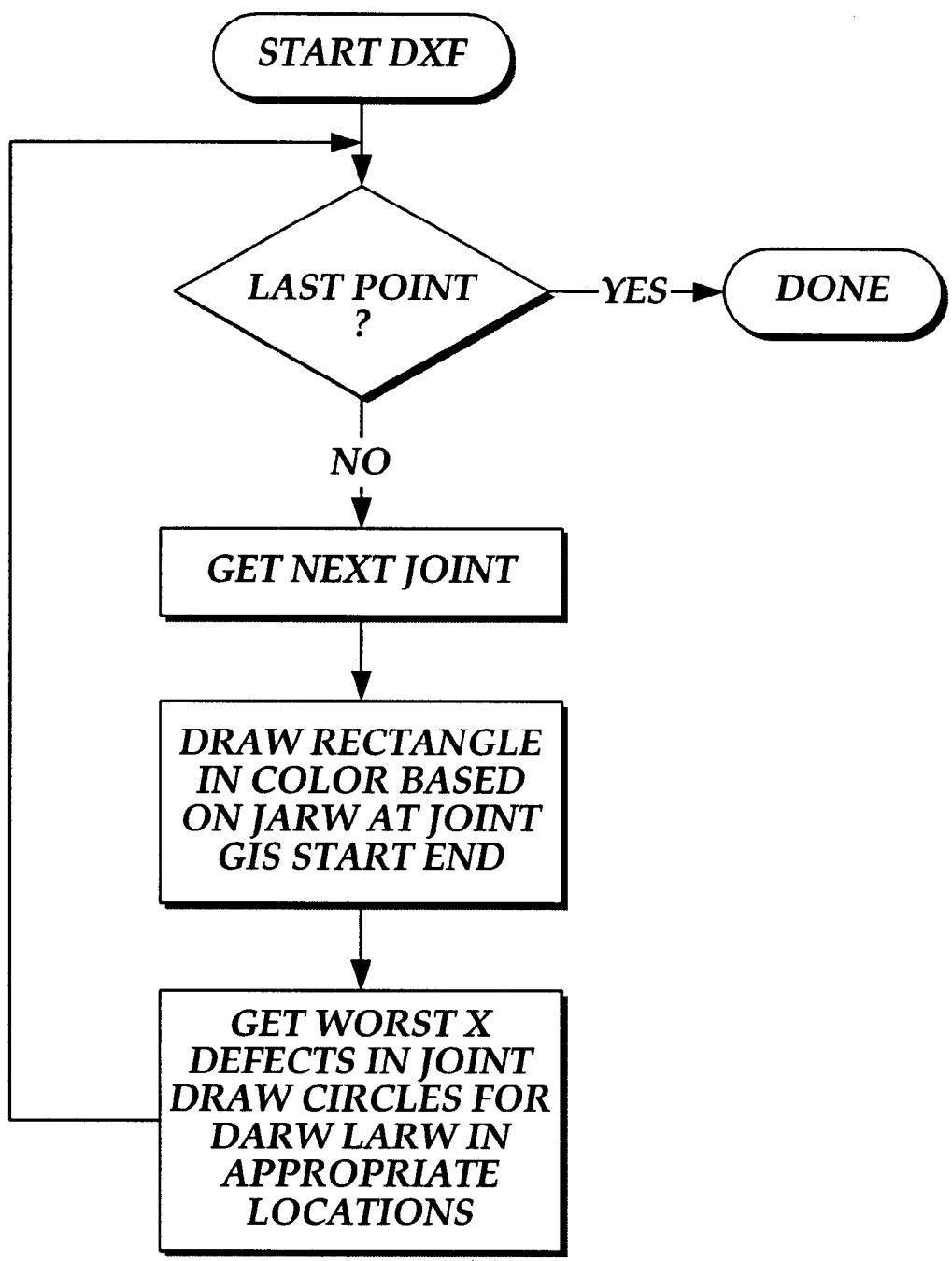

Of particular interest is a feature provided regarding the voltage plane window 562. Referring to FIG. 40, when the cursor moves to a new entry in the Data-Explorer window, the voltage plane window will change to display the feature at the new cursor location. Likewise, when the cursor moves to a new feature in the stripchart window, the Data-Explorer window also moves to display that same data as does the voltage plane as well.

When the view in the voltage plane display is changed at a block 566, inquiry is made at a decision block 568 as to whether the data in the stripchart window from the new location represents a distance of less than a single pipe length amount of data. If so, the program draws all of the data corresponding to the cursor location in the voltage plane at a block 572. If not, the program draws only the joint data corresponding to the cursor location in the voltage plane, at a block 570. Inquiry is then made at a decision block 574 as to whether all necessary variables are available for the data shown in the voltage plane. The necessary variables are those determined by performing the method steps 66, 68, 70, and 72 described above. If not, the voltage plane display continues as is.

If so, the RFT analysis is performed at a block 576 in accordance with the method of step 74. These results are displayed at a block 578 in the voltage plane window 562. In addition, the program includes a display in the voltage plane of the nominal signal, the Phase Profile point, a line connecting the nominal signal and the Phase Profile point, the maximum defect trace data point, and a line connecting the maximum defect trace data point with the Phase Profile point. This display gives a very clear indication of the circumferential and pitting components of a particular defect. This is useful for an operator in quickly determining whether the analysis at that location was reasonable or askew. With this graphical display of the two-step analysis, even a non- or semi-skilled operator can quickly determine whether the results of the automated analysis can be trusted.

Figure 39:
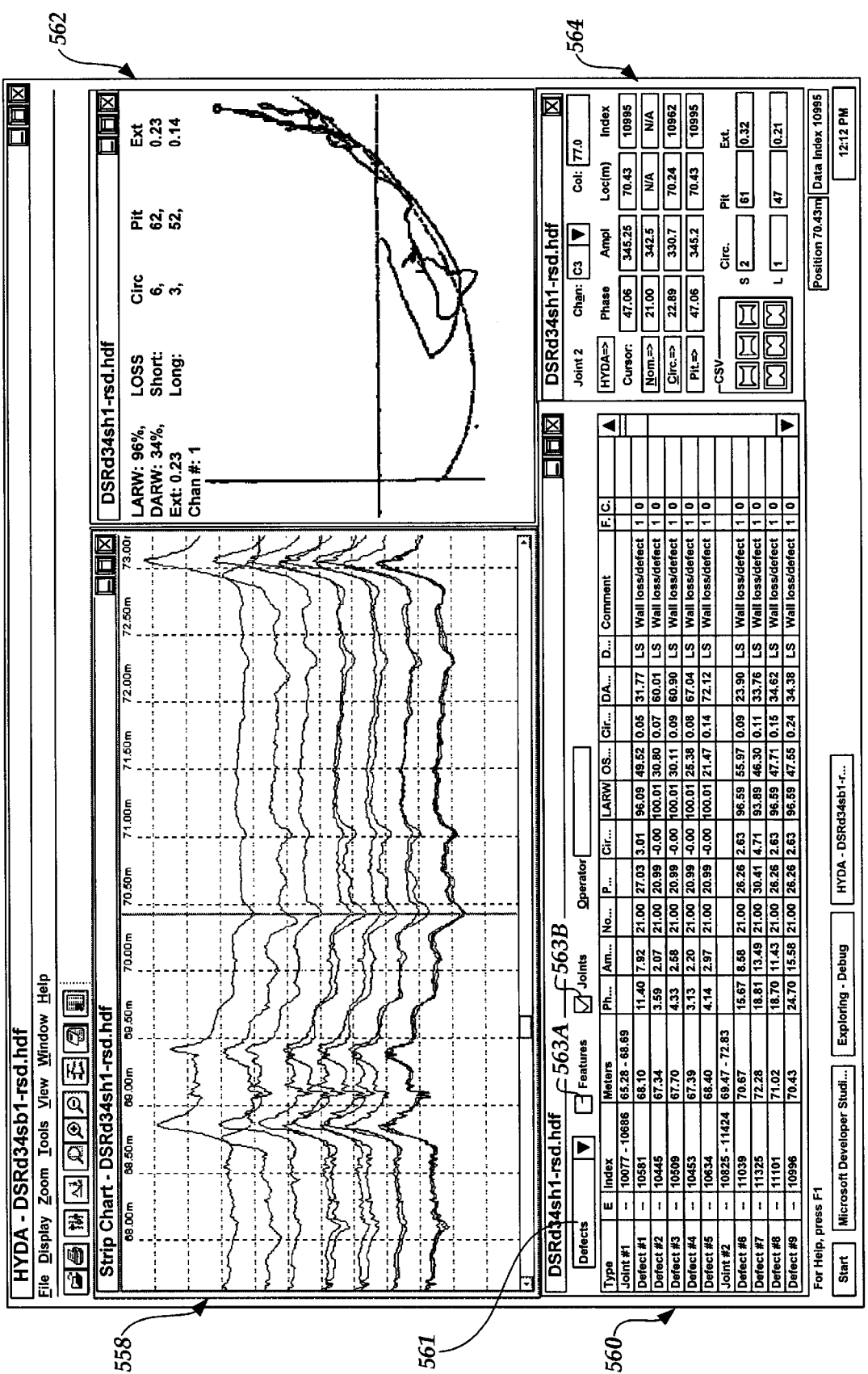

Also, of particular interest is a feature provided when the Data-Explorer window is the active window (560 in FIG. 39). The data displayed in the Data Explorer window is filtered based upon user preferences. The user specifies the primary type of data viewed by selecting his or her viewing preference using an option list 561. The user select to view features, defects or joints. Based on the user selection 561, the user may additionally view none, one or both of the remaining alternatives by means of checkboxes 563A and 563B. In FIG. 39, the user has elected to display defects 561 and joints 563B. In the preferred embodiment illustrated in FIG. 39, the user can further customize the display in the Data Explorer window by specifying which columns are to be displayed for a given category. Preferably a user interface, such as the one illustrated in FIG. 41 is provided for the user to determine which columns are to be displayed.

Figure 41:
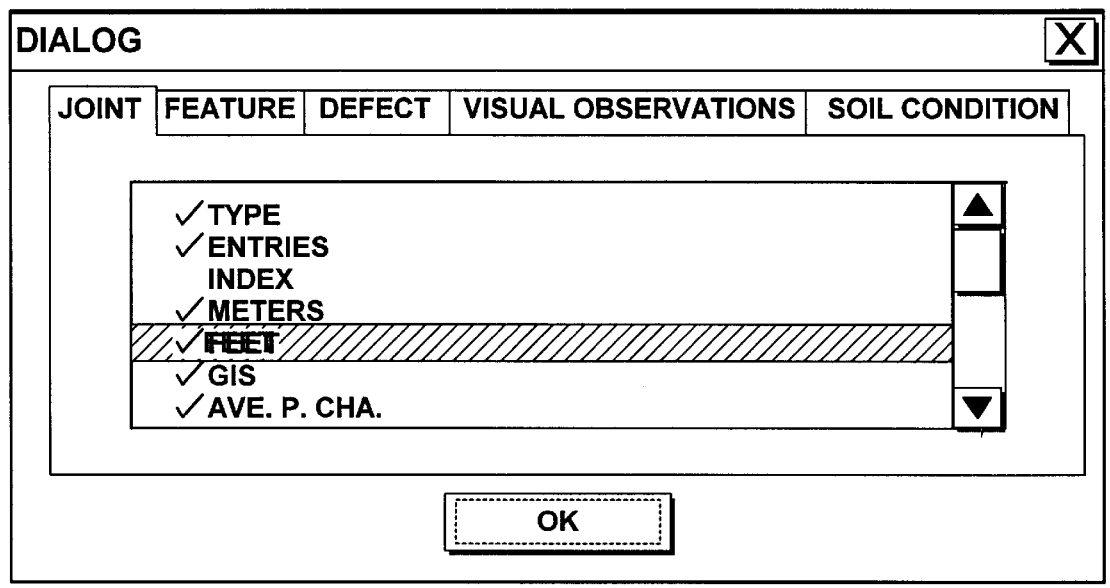

As shown in FIG. 41, for a given category, the user may choose whether or not to display the available items for the specified category. The following items are common to all categories: type; entries; index; meters; feet; Geographic Information System (GIS); date; time and operator. Type is the category for which the data is listed (e.g., feature). The Entries selection allows for changes to be made to the data while still allowing the original data to be viewed. Index refers to the index given to the data point. Meters is the measurement in meters from the start of the run to where the data is located. Feet is the measurement in feet from the start of the run to where the data is located. GIS is a geographic coordinate (X, Y, Z) of the data. Date refers to the date that the data was gathered. Time is the time that the results were calculated. Operator is the name of the operator that entered the result, or a reference to the fact that the result was automatically generated by the program. If more than one category is displayed, the common data is only displayed once.

In addition to the common data described above, there is specific data for each category. The specific data was calculated during the analysis of the data described above in reference to FIG. 7. If the operator elects to display joint data, the operator may display any or all of the following additional joint data: average phase change, joint average remaining wall, error joint average remaining wall; calibration factor; nominal phase; and amplitude offset. Average phase change is the joint average change from nominal phase. It is used in conjunction with the calibration factor to calculate the joint average remaining wall (JARW); JARW is the average remaining wall thickness of the joint based on an analysis of the average phase in the joint. JARW is usually expressed as a percentage of nominal wall. Error joint average remaining wall (Err. JARW) is the absolute error for JARW expressed as a percentage of nominal. Calibration factor is a phase value in degrees representing phase change for a through wall fully circumferential hole. Nominal phase (Nom. Phase) is the phase signal from a nominal piece of pipe, which is used for reference for the analysis. Amplitude offset (Amp. Offset) is the offset made to the amplitude to determine the nominal signal used for the analysis of the joint.

The specific items related to features include: comment; match value and flag. Comment is the first word in the name of the template that matched the feature. Match value indicates the accuracy of the data match to the template. Flag is an area for operator defined data.

The following options can be displayed for the defect category: phase change; amplitude change; nominal phase; phase profile; circumferential phase change; error circumferential phase change; local average remaining wall; error local average remaining wall; one sided equivalent phase change; error one sided equivalent phase change; circumferential extent; defect area remaining wall; error defect area remaining wall; defect area description; comment; and flag. Phase change is the change in the phase from nominal signal caused by a defect area, feature, or other observed item. Amplitude change is the change in the amplitude from nominal signal caused by a defect area, feature, or other observed item. Nominal phase is the phase signal from a nominal piece of pipe, which is used for a reference for the analysis. Phase profile is the phase signal the defect area would cause if only general circumferential metal loss is considered (i.e., no one-sided metal loss). Circumferential phase change is the change caused by general circumferential metal loss (i.e., ignoring one-sided metal loss). Prior circumferential phase change is the absolute phase error for circumferential phase change. Local average remaining wall (LARW) is the remaining wall thickness in a defect area after accounting for the circumferential loss component. LARW is usually expressed as a percentage of nominal wall. Error local average remaining wall is the absolute error for LARW. One sided equivalent phase change is the phase change a one sided defect (i.e., pit) would cause if it was extended around the entire circumference (i.e., the phase change a circumferential defect of equivalent depth would cause. Error one sided equivalent phase change is the absolute error for a one sided equivalent phase change. Defect area remaining wall (DARW) is the minimum remaining wall thickness in a defect area as determined by combining the general circumferential loss with the pitting loss. DARW is usually reported as a percentage of nominal with a circumferential extent between 0 and 1.00, where 1.00 covers the entire circumference, 0.50 covers half, etc. Error circumferential extent is the absolute error for circumferential extent. Error defect area remaining wall is the absolute error for DARW. Defect area description is a short description for a defect, wall loss, and/or pitting.

Figure 47:
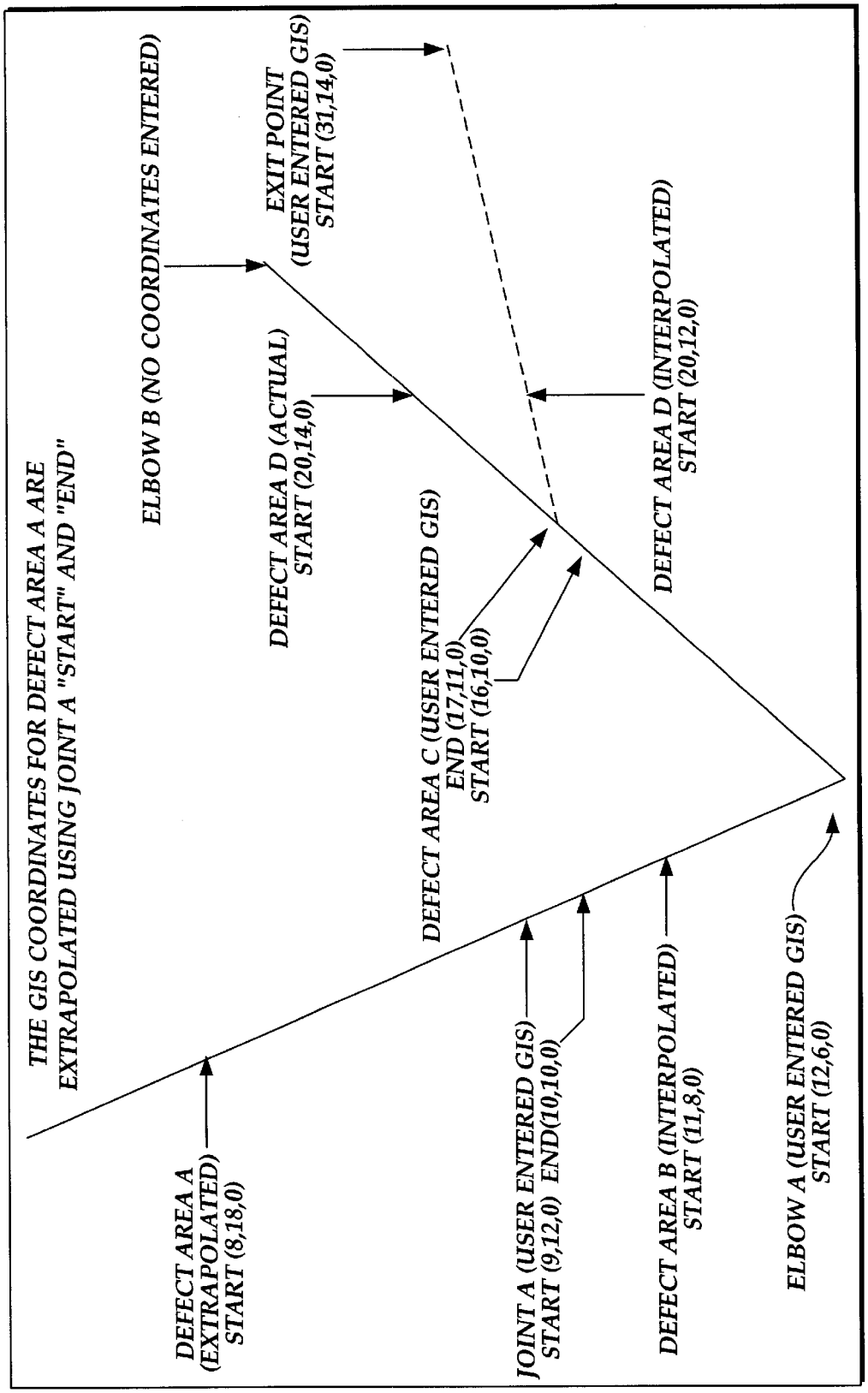

By selecting an item in the data explorer a popup menu, is displayed that allows the operator to select GIS points. In a preferred embodiment, a user interface allows the user to define start or end GIS X, Y, and Z coordinate of the selected item in the data explorer window, anchoring that particular point in the data to that GIS coordinate. Alternatively, the user can enter the GIS coordinates in the data explorer window. Once two or more GIS anchoring points have been defined the user can elect to calculate the GIS start and end coordinates of any item in the data explorer by using a Calculate GIS option FIG. 47 illustrates the results of calculating additional GIS points once some GIS points have been defined.

Once the GIS coordinates of all the results of the analysis have been defined, the results can be exported in a graphical drawing format, such as a Drawing eXchange Format (DXF) file, which can be imported into any number of commercially available drawing programs and databases, such as "AutoCad." This graphical display of the results of the analysis formed in accordance with the present invention, makes it possible for municipal engineers to combine the results of an RFT evaluation of a water line with their drawing database of the line. The DXF drawing is also a useful and intuitive way of summarizing the condition of a line.

The DXF file is created by using the Tools—Create Analysis Results DXF File menu item (FIG. 20). The DXF file is created as described in FIGS. 42 and 43, where the start and the end GIS location of a joint a rectangle is displayed in a color representing the joint average remaining wall (JARW) value. See FIG. 4B Likewise, at each defect reported, two circles are drawn at the defect GIS coordinate, the outer one colored to indicate the local average remaining wall (LARW), and the inner one the defect remaining wall (DARW). Features not analyzed are shown using a different color, e.g., gray and using a different shape, e.g., rectangle. Preferably, a legend defining the colors and shapes is also displayed.

As will be appreciated from the above, the present invention is a powerful tool for analyzing a massive amount of RFT raw data. This greatly reduces the amount of paper plots required for subsequent manual examination. The invention uses some of the thought processes of a skilled technician experienced in the RFT technique and also adds the unique aspects described above. The present invention as embodied in a computer program accomplishes this while greatly reducing the analysis time. In addition, the method and its software implementation reduces subjectivity in the analysis and improves its resulting accuracy.

While the preferred embodiment of the invention has been illustrated and described, it will be appreciated that various changes can be made therein without departing from the spirit and scope of the invention. For example, the method and program may be used for analysis of other ferrous pipes (e.g., small bore pipes) in addition to use with the typically large pipes found in water, sewage, gas, and oil pipes. In fact, the method may be used on virtually any RFT data sets taken in industrial piping.

What is claimed is:

1. A method for determining pipeline defects using remote field technology data obtained from an inspection of a pipeline, the data including a plurality of data points, a processor and memory being available for manipulating the data, the method comprising the computer-implemented steps of:

(a) using a plurality of data points each having a phase signal and an amplitude signal;

(b) analyzing the data to determine signals indicative of pipeline defects, including determining which portions of the data represent circumferential wall loss defects and which portions of the data represents non-circumferential wall loss defects, and combining the circumferential and non-circumferential wall data to determine a total wall loss for the defect; and (c) quantifying the defects using the circumferential wall loss and the non-circumferential wall loss values.

2. The method according to claim 1, further comprising preparing the data prior to analyzing it, the preparing including at least one of filtering, smoothing, and decimating the data.

3. A method for determining pipeline defects using remote field technology data obtained from an inspection of a pipeline, the data including a plurality of data points having phase and amplitude signals, a processor and memory being available for manipulating the data, the method comprising the computer-implemented steps of:

(a) analyzing the data to determine signals indicative of pipeline defects, including determining which portions of the data represent circumferential wall loss defects and which portions of the data represents non-circumferential wall loss defects, and combining the circumferential and non-circumferential wall data to determine a total wall loss for the defect;

(b) quantifying the defects using the circumferential wall loss and the non-circumferential wall loss values; and (c) preparing the data prior to analyzing it, the preparing including at least one of filtering, smoothing, and decimating the data, wherein preparing the data includes filtering the data to determine a median element, the filtering including
  (i) defining a fixed data set size for the filtering;
  (ii) applying the data set size sequentially to the data by
    (1) determining for each data point in the data set a total distance, the total distance being the sum of the distances between that point and all other data points in that data set; and
    (2) identifying the data point in the set having the smallest total distance; and
  (iii) using the data point having the smallest total distance as the median element for that data set.

4. A method for determining pipeline defects using remote field technology data obtained from an inspection of a pipeline, the data including a plurality of data points having phase and amplitude signals, a processor and memory being available for manipulating the data, the method comprising the computer-implemented steps of:

(a) analyzing the data to determine signals indicative of pipeline defects, including determining which portions of the data represent circumferential wall loss defects and which portions of the data represents non-circumferential wall loss defects, and combining the circumferential and non-circumferential wall data to determine a total wall loss for the defect;

(b) quantifying the defects using the circumferential wall loss and the non-circumferential wall loss values; and (c) preparing the data prior to analyzing it, the preparing including at least one of filtering, smoothing, and decimating the data, wherein preparing the data includes smoothing the data using a moving block average filter.

5. The method according to claim 1, wherein the data is initially parsed into smaller data portions, the analyzing of data being conducted on the smaller data portions.

6. The method according to claim 5, wherein the smaller data portions are individual pipe lengths.

7. A method for determining pipeline defects using remote field technology data obtained from an inspection of a pipeline, the data including a plurality of data points having phase and amplitude signals, a processor and memory being available for manipulating the data, the method comprising the computer-implemented steps of:

(a) analyzing the data to determine signals indicative of pipeline defects, including determining which portions of the data represent circumferential wall loss defects and which portions of the data represents non-circumferential wall loss defects, and combining the circumferential and non-circumferential wall data to determine a total wall loss for the defect;

(b) quantifying the defects using the circumferential wall loss and the non-circumferential wall loss values; and (c) identifying signals indicative of non-analyzable features in the data and ignoring such signals when analyzing the data for defects, the non-analyzable features including at least one of a bell-and-spigot pipe connection, a tee, an elbow, and a valve.

8. The method according to claim 7, wherein the data is parsed into smaller data portions delineated by the non-analyzable features, the analyzing of data being conducted on the smaller data portions.

9. The method according to claim 8, wherein the smaller data portions are individual pipe lengths.

10. A method for determining pipeline defects using remote field technology data obtained from an inspection of a pipeline, the data including a plurality of data points having phase and amplitude signals, a processor and memory being available for manipulating the data, the method comprising the computer-implemented steps of:

(a) analyzing the data to determine signals indicative of pipeline defects, including determining which portions of the data represent circumferential wall loss defects and which portions of the data represents non-circumferential wall loss defects, and combining the circumferential and non-circumferential wall data to determine a total wall loss for the defect;

(b) quantifying the defects using the circumferential wall loss and the non-circumferential wall loss values; and (c) identifying signals indicative of non-analyzable features in the data, the identifying including comparing at least one template representative of a non-analyzable feature with the pipe data.

11. The method according to claim 10, wherein the at least one template is stored in memory.

12. The method according to claim 11, wherein the memory includes multiple templates selectable by an operator for use in comparing with the data.

13. The method according to claim 10, wherein the at least one template is modified by at least one of adjusting, scaling, and shifting the template values to correspond to the pipe data.

14. The method according to claim 10, wherein an operator defines a portion of the data as a template for use in comparing with the data.

15. The method according to claim 10, wherein the identifying of non-analyzable features includes selecting a template, sequencing through the data to locate portions that are similar to the template, and if a similar trace is found, creating a new template to match the data and rechecking the data using the new template; the similarity of the trace being determined by a predefined logic.

16. The method according to claim 15, wherein the template is selected from memory and the new template replaces the selected template in memory.

17. The method according to claim 15, wherein sequencing through the data includes calculating the sum of the squared difference between the template and the data set at each data point.

18. The method according to claim 17, wherein the predefined logic includes a characterization of how well the data matched the template, the characterization including a worst match, the new template being defined using the data having the worst match.

19. A method for determining pipeline defects using remote field technology data obtained from an inspection of a pipeline, the data including a plurality of data points having phase and amplitude signals, a processor and memory being available for manipulating the data, the method comprising the computer-implemented steps of:

(a) analyzing the data to determine signals indicative of pipeline defects, including determining which portions of the data represent circumferential wall loss defects and which portions of the data represents non-circumferential wall loss defects, and combining the circumferential and non-circumferential wall data to determine a total wall loss for the defect; and (b) quantifying the defects using the circumferential wall loss and the non-circumferential wall loss values;

wherein analyzing the data includes (i) defining a nominal signal and defining a Reference Curve, the Reference Curve being a collection of theoretical phase and amplitude values for decreasing uniform circumferential wall thickness for the pipe;

(ii) determining which data points are positioned near the Reference Curve based on the nominal signal, the data point phase and amplitude signals, and a predefined logic;

(iii) locating defects in the pipe as a function of the data point phase signals; and (iv) determining for each defect which portions of the data represent circumferential wall loss and which portions represent non-circumferential wall loss using the determinations of which data points are positioned near the Reference Curve.

20. The method according to claim 19, wherein (a) defining a nominal signal includes defining a nominal phase ($P_{NOM}$); and (b) determining which data points are positioned near the Reference Curve includes defining a Phase Profile for the data;

(c) determining circumferential wall loss and non-circumferential wall loss is based on the Phase Profile; and (d) quantifying defects includes calculating for each defect a total equivalent-phase-shift (EQPS) as a combination of a circumferential equivalent-phase-shift ($EQPS_{CIRC}$) and a non-circumferential equivalent-phase-shift ($EQPS_{NON-CIRC}$); $EQPS_{CIRC}$ and $EQPS_{NON-CIRC}$ each being a function of $P_{NOM}$ and Phase Profile.

21. The method according to claim 20, wherein $P_{NOM}$ is determined by sorting the phase data into ascending order, removing a percentage of the smallest phase data values, and setting $P_{NOM}$ equal to the smallest remaining phase data value.

22. The method according to claim 20, wherein the predefined logic includes setting the Phase Profile for a data point equal to the data point phase signal for those data points near $P_{NOM}$ and those data points within a predetermined Reference_Curve_Threshold Margin and Extent_Threshold.

23. The method according to claim 20, wherein the predefined logic includes defining an intersection point having a given phase for groups of data points that are not near the Reference Curve, and setting the Phase Profile for those data points equal to the intersection point phase.

24. The method according to claim 23, wherein the intersection point is the crossing location on the Reference Curve of a line representative of the group of data points that are not near the Reference Curve, the line being determined using at least one of a least squares fit and a linear interpolation of the consecutive data points for that group of data points.

25. The method according to claim 20, wherein (a) quantifying defects includes identifying the maximum phase signals;

(b) $EQPS_{CIRC}$ is a function of the difference between $P_{NOM}$ and the Phase Profile value for each maximum defect data point;

(c) for those data points having a Phase Profile value at the maximum defect data point equal to the maximum defect phase signal, $EQPS_{NON-CIRC}$ is set to zero; and (d) for the remaining maximum defect data points, $EQPS_{NON-CIRC}$ is set equal to an RFT Phase Lag Angle $\phi$.

26. The method according to claim 19, wherein locating defects includes locating local maximum phase signals within a group of data points.

27. The method according to claim 26, wherein those data points having a maximum phase signal less than a predefined minimum amount are disregarded.

28. The method according to claim 26, wherein those consecutive data points having a maximum phase signal within a predefined minimum distance to another maximum actual phase of larger value are disregarded.

29. The method according to claim 1, wherein quantifying pipe defects includes calibrating the inspection data to correspond dimensionally with the pipeline.

30. A method for determining pipeline defects using remote field technology data obtained from an inspection of a pipeline, the data including a plurality of data points having phase and amplitude signals, a processor and memory being available for manipulating the data, the method comprising the computer-implemented steps of:

(a) analyzing the data to determine signals indicative of pipeline defects, including determining which portions of the data represent circumferential wall loss defects and which portions of the data represents non-circumferential wall loss defects, and combining the circumferential and non-circumferential wall data to determine a total wall loss for the defect; and (b) quantifying the defects using the circumferential wall loss and the non-circumferential wall loss values; wherein quantifying pipe defects includes calibrating the inspection data to correspond dimensionally with the pipeline; and wherein quantifying pipe defects includes calibrating the data by obtaining information from a representative pipe having no defects, the calibrating including (i) determining a nominal data signal for the representative pipe;

(ii) placing a defect in the representative pipe and determining the signal change resulting from the defect; and (iii) using the nominal data signal and the signal change to calibrate the pipeline data.

31. The method according to claim 30, wherein calibrating the data includes defining a calibration amount that results in a selected percentage of the data being a 100 percentage through-wall loss.

32. A method for determining pipeline defects using remote field technology data obtained from an inspection of a pipeline, the data including a plurality of data points having phase and amplitude signals, a processor and memory being available for manipulating the data, the method comprising the computer-implemented steps of:

(a) analyzing the data to determine signals indicative of pipeline defects, including determining which portions of the data represent circumferential wall loss defects and which portions of the data represents non-circumferential wall loss defects, and combining the circumferential and non-circumferential wall data to determine a total wall loss for the defect; and (b) quantifying the defects using the circumferential wall loss and the non-circumferential wall loss values; wherein quantifying pipe defects includes calibrating the inspection data to correspond dimensionally with the pipeline; and wherein quantifying pipe defects includes calibrating the data including (i) exposing a portion of the pipeline having no defects;

(ii) determining nominal phase and amplitude values directly from the exposed portion of the pipe having no defects; and (iii) determining phase and amplitude values for a location outside of the exposed pipeline in free air; wherein the nominal and free air phase and amplitude values are used to calibrate the data.

33. The method according to claim 1, wherein quantifying pipe defects includes calculating at least one of an average remaining wall thickness amount per pipe (JARW), an average circumferential remaining wall thickness amount per defect (LARW), and an average total remaining wall thickness amount per defect (DARW).

34. The method according to claim 19, wherein quantifying pipe defects includes calculating at least one of an average remaining wall thickness amount per pipe (JARW), an average circumferential remaining wall thickness amount per defect (LARW), and an average total remaining wall thickness amount per defect (DARW).

35. The method according to claim 20, wherein quantifying pipe defects includes calculating at least one of an average remaining wall thickness amount per pipe (JARW), an average circumferential remaining wall thickness amount per defect (LARW), and an average total remaining wall thickness amount per defect (DARW).

36. The method according to claim 35, wherein the average remaining wall thickness amount is a function of an average equivalent-phase-shift amount ($EQPS_{CAL}$) and $EQPS_{CAL}$.

37. The method according to claim 35, wherein the average circumferential remaining wall thickness amount is a function of $EQPS_{CIRC}$ and $EQPS_{CAL}$.

38. The method according to claim 35, wherein the average remaining wall thickness amount is a function of $EQPS_{CIRC}$ and $EQPS_{CAL}$.

39. A method for determining pipeline defects using remote field technology data obtained from an inspection of a pipeline, the data including a plurality of data points having phase and amplitude signals, a processor and memory being available for manipulating the data, the method comprising the computer-implemented steps of:

(a) parsing the data into smaller portions representative of individual pipe lengths;

(b) analyzing the data to determine signals indicative of pipeline defects, including determining which portions of the data represent circumferential wall loss defects and which portions of the data represents non-circumferential wall loss defects, and combining the circumferential and non-circumferential wall data to determine a total wall loss for the defect; the analyzing including (i) defining a nominal signal and defining a Reference Curve, the Reference Curve being a collection of theoretical phase and amplitude values for decreasing uniform circumferential wall thickness for the pipe;

(ii) determining which data points are positioned near the Reference Curve based on the nominal signal, the data point phase and amplitude signals, and a predefined logic;

(iii) locating defects in the pipe as a function of the data point phase signals; and (iv) determining for each defect which portions of the data represent circumferential wall loss and which portions represent non-circumferential wall loss using the determinations of which data points are positioned near the Reference Curve; and (c) quantifying the defects using the circumferential wall loss and the non-circumferential wall loss values, the quantifying including calibrating the data to correspond dimensionally with the pipeline.

40. The method according to claim 39, wherein (a) defining a nominal signal includes defining a nominal phase ($P_{NOM}$); and (b) determining which data points are positioned near the Reference Curve includes defining a Phase Profile for the data;

(c) determining circumferential wall loss and non-circumferential wall loss is based on the Phase Profile; and (d) quantifying defects includes calculating for each defect a total equivalent-phase-shift (EQPS) as a combination of a circumferential equivalent-phase-shift ($EQPS_{CIRC}$) and a non-circumferential equivalent-phase-shift ($EQPS_{NON-CIRC}$); $EQPS_{CIRC}$ and $EQPS_{NON-CIRC}$ each being a function of $P_{NOM}$ and Phase Profile.

41. The method according to claim 40, wherein quantifying pipe defects includes calculating at least one of an average remaining wall thickness amount per pipe (JARW), an average circumferential remaining wall thickness amount per defect (LARW), and an average total remaining wall thickness amount per defect (DARW).

42. A method of determining changes in wall thickness of a pipeline using measured remote field data including a plurality of data points having phase and amplitude signals, the method comprising:

(a) defining a nominal signal and defining a Reference Curve, the Reference Curve being a collection of theoretical phase and amplitude values for decreasing uniform circumferential wall thickness for the pipeline; and (b) determining which measured data points are positioned near the Reference Curve based on the nominal signal and a predefined logic; wherein for those data points located near the Reference Curve, circumferential changes in wall thickness are determined according to the difference between the data point phase value and the nominal phase value; and (c) determining which measured data points are not positioned near the Reference Curve including identifying an intersection phase signal for those data points; wherein for those data points not located near the Reference Curve, non-circumferential changes in wall thickness are determined according to the difference between the data point phase value and the intersection phase signal.

43. A method of determining non-circumferential changes in wall thickness of a pipeline using measured remote field data including a plurality of data points having phase and amplitude signals, the method comprising:

(a) defining a Reference Curve for the pipeline, the Reference Curve being a collection of theoretical phase and amplitude values for decreasing uniform circumferential wall thickness for the pipeline; and (b) determining which measured data points are representative of non-circumferential changes in wall thickness by determining which measured data points are not positioned near the Reference Curve based on a predefined logic;

wherein for those data points not located near the Reference Curve, (i) assigning an intersection phase value representative of a nominal circumferential phase amount for those data points; and (ii) defining non-circumferential changes in wall thickness according to the difference between the measured data point phase values and the intersection phase signal.

* * * * *

UNITED STATES PATENT AND TRADEMARK OFFICE
CERTIFICATE OF CORRECTION

PATENT NO.  : 6,359,434 B1
DATED       : March 19, 2002
INVENTOR(S) : J. Winslow et al.

It is certified that error appears in the above-identified patent and that said Letters Patent is hereby corrected as shown below:

<u>Title page,</u>
Item [73], Assignee, "Cananda" should read -- Canada --
Item [74], *Attorney, Agent, or Firm*, "O'Conner" should read -- O'Connor --
Item [56], References Cited, OTHER PUBLICATIONS, "David Mackintosh" reference, "19994," should read -- 1994, --;
"Staples, L.B., reference, "Undergroud" should read -- Underground --

<u>Column 1,</u>
Line 13, "data. (also" should read -- data (also --
Line 37, "pipes, Such" should read -- pipes. Such --

Figure 3:
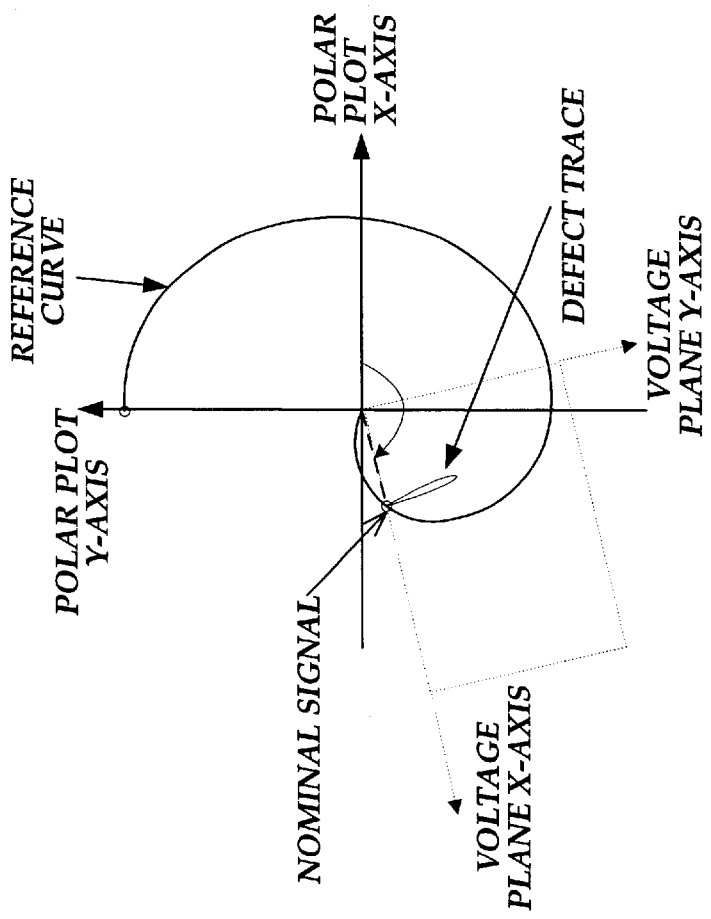
FIG. 3 is a voltage plane plot of the data of FIG. 2.

<u>Column 2,</u>
Lines 5-6, "Remote Field Eddy Current Analysis in Small-Bore Ferromagnetic Tubes," should read -- *Remote Field Eddy Current Analysis in Small-Bore Ferromagnetic Tubes,* --
Line 46, "FIG. 3 that" should read -- FIG. 3, that --

<u>Column 3,</u>
Lines 10-11, "Remote Field Eddy Current for Examination of Ferromagnetic Tubes," should read -- *Remote Field Eddy Current for Examination of Ferromagnetic Tubes,* --
Line 26, "The analyst must choose" should not begin a new paragraph
Line 28, "judge tile" should read -- judge the --
Line 30, "tile selection" should read -- the selection --
Line 32, "resulting, wall loss" should read -- resulting wall loss --
Line 61, "(sinice" should read -- (since --

<u>Column 4,</u>
Line 12, "intensive, Locating" should read -- intensive. Locating --
Line 29, "PFT" should read -- RFT --
Line 38, "length is," should read -- lengths, --
Line 52, "wherein" should read -- wherein: --

<u>Column 5,</u>
Line 31, "invention," should read -- invention; --
Line 47, "templates matches" should read --template matches --

UNITED STATES PATENT AND TRADEMARK OFFICE
CERTIFICATE OF CORRECTION

PATENT NO. : 6,359,434 B1
DATED : March 19, 2002
INVENTOR(S) : J. Winslow et al.

It is certified that error appears in the above-identified patent and that said Letters Patent is hereby corrected as shown below:

Column 6,
Lines 4 and 7, "strip chart" should read -- stripchart --
Line 38, "Following, is" should read -- Following is --

Column 7,
Line 7, "block 62, The" should read -- block 62. The --
Line 16, "location, if" should read -- location. If --
Line 18, "Tile logic" should read -- The logic --
Lines 27-28, after "one-sided" delete "non circum-ferential"
Line 29, "a pitting defect" should read -- a non-circumferential pitting defect --
Line 30, "signal, and" should read -- signal and --
Line 37, "tile tasks" should read -- the tasks --
Line 52, "oil" should read -- on --

Column 8,
Line 22, "oil" should read -- on --
Line 64, "III" should read -- in --

Column 9,
Line 32, "selected as" should read -- is selected as --
Line 36, "integer size it" should read -- integer size n --
Line 47, "preferable" should read -- preferably --

Column 10,
Line 3, "$(x_i-x_j)^2+(y_i-y_j)=D_{ij}^2$" should read -- "$(x_i-x_j)^2+(y_i-y_j)^2=D_{ij}^2$" --
Line 9, "relative each" should read -- relative to each --
Line 11, delete "TABLE 2" and the barred line
Line 18, before the line beginning
"Applied
  $FDS_k$"
insert -- TABLE 2 -- and the barred line
Line 66, "issued" should read -- is issued --

Column 11,
Line 3, "elbow," should read -- elbows, --
Line 6, "tile operator" should read -- the operator --
Line 42, "lie or she" should read -- he or she --

UNITED STATES PATENT AND TRADEMARK OFFICE
CERTIFICATE OF CORRECTION

PATENT NO.   : 6,359,434 B1
DATED        : March 19, 2002
INVENTOR(S)  : J. Winslow et al.

It is certified that error appears in the above-identified patent and that said Letters Patent is hereby corrected as shown below:

Column 12,
Line 29, "tile same" should read -- the same --
Line 31, "Tile difference" should read -- The difference --
Line 34, "tile maximum" should read -- the maximum --

Column 13,
Line 13, "provided, however," should read -- provided; however, --
Line 43, "Amount changed." should read -- Amount should be changed. --
Line 48, "none-analyzable" should read -- non-analyzable --

Column 14,
Line 30, "Valnies" should read -- Values --
Line 59, "tile voltage" should read -- the voltage --

Column 15,
Line 3, "(A). Which" should read -- (A), which --
Line 29, "However" should read -- However, --
Line 39, "having of both" should read -- having both --
Line 45, "The phase prefile" should read -- The Phase Profile --
Line 64, "done for at any point" should read -- done at any point --

Column 16,
Line 2, "$\Phi$ skin depths" should read -- $\varphi$ skin depths --
Line 3, "$\Phi$ radians" should read -- $\varphi$ radians --
Line 4, "factor of e$\Phi$" should read -- factor of e$\varphi$ --
Line 5, (1 radians" should read -- (1 radian --
Line 10, "$e^{\Phi} \angle ^{\Phi_o}$." should read -- $e^{\varphi} \angle ^{\varphi_o}$. --

Column 17,
Line 6, "Reference Curve." should read -- Reference Curve and nominal signal. --
Line 8, "Curve and nominal signal is" should read -- Curve is --
Line 51, "$L_{LSfFIT}$" should read -- $L_{LSFIT}$ --
Line 65, "and to?" should read -- and B --
Line 66, "from, the origin B, the" should read -- from the origin to the --

Column 18,
Line 3, "tile logic" should read -- the logic --
Line 9, "tile Reference" should read -- the Reference --
Line 11, "determine the" should read -- determine if the --
Line 29, "defect ." should read -- defect. --

UNITED STATES PATENT AND TRADEMARK OFFICE
CERTIFICATE OF CORRECTION

PATENT NO. : 6,359,434 B1
DATED : March 19, 2002
INVENTOR(S) : J. Winslow et al.

Page 4 of 6

It is certified that error appears in the above-identified patent and that said Letters Patent is hereby corrected as shown below:

Column 19,
Line 37, "FIG. 44 and 45" should read -- FIGS. 44 and 45, --
Line 62, "result are" should read -- results are --

Column 20,
Line 3, "the f(n)" should read -- then f(n) --
Line 55, "Curve.)" should read -- Curve). --
Line 58, "(1,0) The" should read -- (1,0). The --
Line 66, "pittinig-only" should read -- pitting-only --

Column 21,
Line 17, "Lag $\phi$ angle" should read -- Lag $\varphi$ angle --
Line 18, "to solve for $\phi$" should read -- to solve for $\varphi$ --
Line 19, "0=f($\phi$)" should read -- 0=f($\varphi$) --
Line 25, "Phase Lag $\phi$" should read -- Phase Lag $\varphi$ --
Line 28, "function of $\phi$" should read -- function of $\varphi$ --
Line 30, "q=($e^{\phi}$(sin $\phi$·cot $\alpha$-cos$\phi$)+$^{-1}$)" should read -- q=($e^{\varphi}$(sin $\varphi$·cot $\alpha$-cos$\varphi$)+1)$^{-1}$ --
Line 53, "In preferred embodiment," should read -- In the preferred embodiment, --
Line 60, "material properties as the" should read -- material properties to the --

Column 22,
Line 9, "defect This" should read -- defect. This --

Column 23,
Line 12, "Term DARW" should read -- The term DARW --
Line 33, "estimate". By" should read -- estimate" by --
Line 34, "phase are" should read -- phase is --
Line 35, "and those" should read -- and that those --
Line 37, "both $\alpha$a" should read -- both $\Delta$a --
Line 54, "method is" should read -- method are --

Column 25
Line 8, "proceeding steps." should read -- preceding steps. --
Line 16, "(though, doing" should read -- (though doing --
Line 62, "strip chart" should read -- stripchart --

UNITED STATES PATENT AND TRADEMARK OFFICE
CERTIFICATE OF CORRECTION

PATENT NO.       : 6,359,434 B1
DATED            : March 19, 2002
INVENTOR(S)      : J. Winslow et al.

It is certified that error appears in the above-identified patent and that said Letters Patent is hereby corrected as shown below:

Column 27,
Line 31, "pipe-lengths" should read -- pipe lengths --
Line 60, "EQIS" should read --EQPS--
Line 65, "E(QPS" should read -- EQPS --

Column 28,
Line 11, "Drawing exchange" should read -- Drawing eXchange --
Line 34, "it, FIG. 32." should read -- in FIG. 32. --

Column 29,
Line 16, "shown II FIG." should read -- shown in FIG. --
Line 17, "data point location, the" should read -- data point location; the --
Line 55, "same data as" should read -- same data, as --

Column 30,
Line 24, "The user select" should read -- The user selects --
Line 33, "FIG. 41 is" should read -- FIG. 41, is --

Column 31,
Line 32, "Prior" should read -- Error --
Line 55, "data explorer a popup menu," should read -- data explorer, a popup menu --
Line 65, "GIS option FIG." should read -- GIS option. FIG. --

Figure 4:
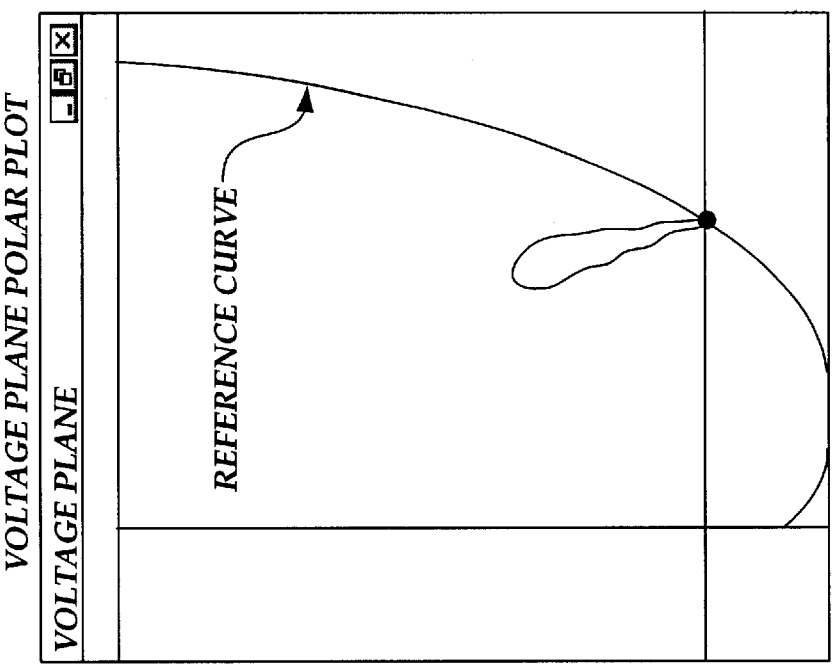
FIG. 4 is an ADEPT computer-plotted voltage plane display of example phase and amplitude data.
Figure 46:
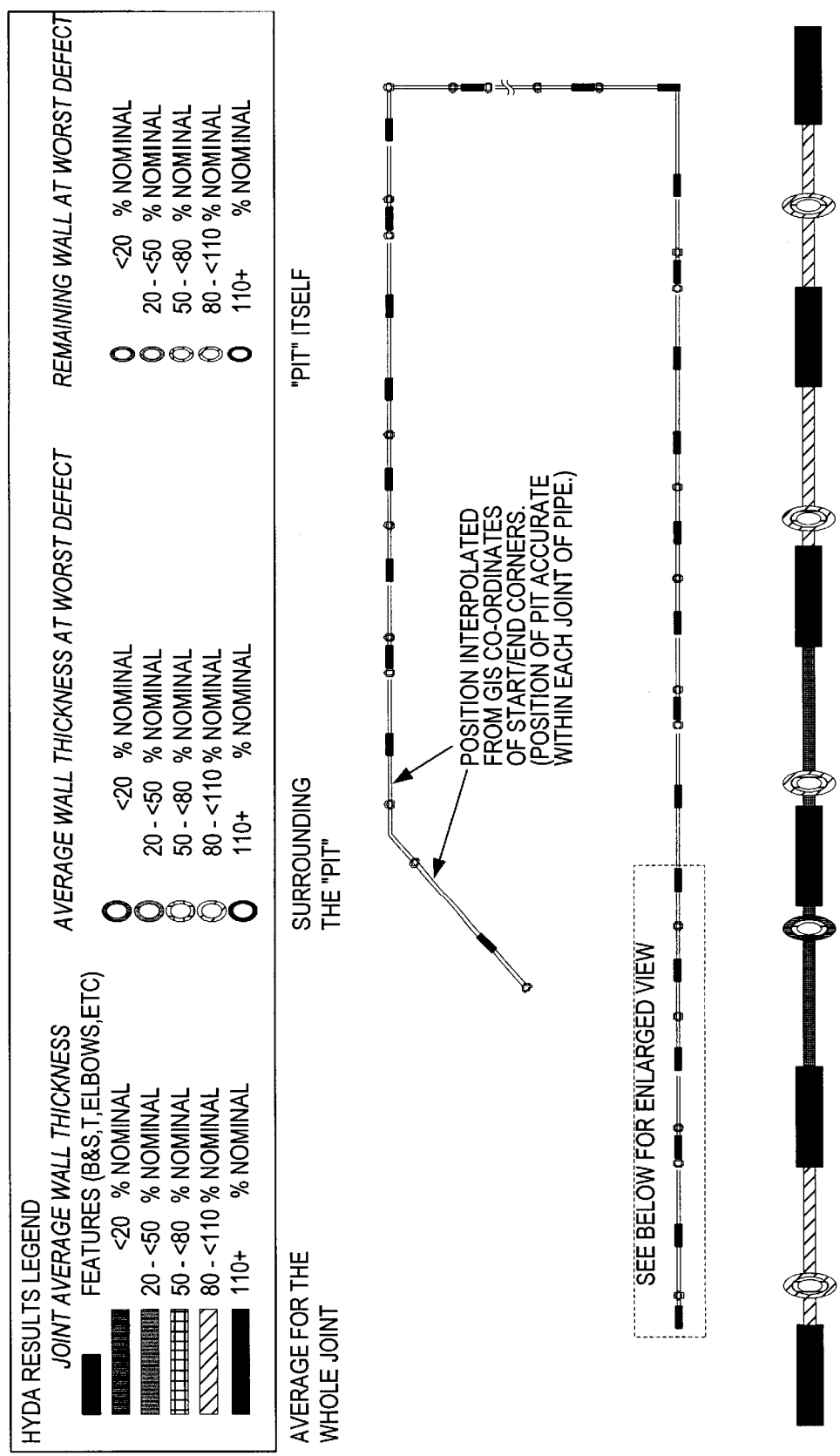

Column 32,
Line 14, "where the" should read -- where at the --
Line 17, "FIG. 4B Likewise" should read -- FIG. 46. Likewise --
Line 23, "e.g., gray" should read -- e.g., gray, --
Line 58, "represents" should read -- represent --

Column 33,
Line 10, 41 and 66, "represents" should read -- represent --

Column 34,
Line 25, "represents" should read -- represent --

Column 35,
Line 8, "represents" should read -- represent --
Line 33, after "($P_{NOM}$); " delete "and"

UNITED STATES PATENT AND TRADEMARK OFFICE
CERTIFICATE OF CORRECTION

PATENT NO. : 6,359,434 B1
DATED : March 19, 2002
INVENTOR(S) : J. Winslow et al.

It is certified that error appears in the above-identified patent and that said Letters Patent is hereby corrected as shown below:

Column 36,
Line 39, "represents" should read -- represent --

Column 37,
Lines 4 and 61, "represents" should read -- represent --

Column 38,
Line 21, after "($P_{NOM}$); " delete "and"
Line 50, delete "and"

Signed and Sealed this

Seventeenth Day of August, 2004

JON W. DUDAS
*Acting Director of the United States Patent and Trademark Office*